United States Patent
Manel et al.

(10) Patent No.: US 10,010,607 B2
(45) Date of Patent: Jul. 3, 2018

(54) METHOD FOR PREPARING VIRAL PARTICLES WITH CYCLIC DINUCLEOTIDE AND USE OF SAID PARTICLES FOR INDUCING IMMUNE RESPONSE

(71) Applicants: INSTITUT CURIE, Paris (FR); INSERM (INSTITUT NATIONAL DE LA SANTE ET DE LA RECHERCHE MEDICALE), Paris (FR)

(72) Inventors: Nicolas Manel, Paris (FR); Matteo Gentili, Paris (FR); Satoh Takeshi, Tokyo (JP); Jan Rehwinkel, Oxford (GB); Anne Bridgeman, Wallingford (GB); Tamara Davenne, Oxford (GB); Jonathan Maelfait, Oxford (GB)

(73) Assignees: INSTITUT CURIE, Paris (FR); INSERM (INSTITUT NATIONAL DE LA SANTE ET DE LA RECHERCHE MEDICALE), Paris (FR)

(*) Notice: Subject to any disclaimer, the term of this patent is extended or adjusted under 35 U.S.C. 154(b) by 72 days.

(21) Appl. No.: 14/855,744

(22) Filed: Sep. 16, 2015

(65) Prior Publication Data
US 2016/0074507 A1    Mar. 17, 2016

Related U.S. Application Data

(60) Provisional application No. 62/051,016, filed on Sep. 16, 2014.

(51) Int. Cl.
*A61K 39/39* (2006.01)
*A61K 39/00* (2006.01)
*C12N 7/00* (2006.01)

(52) U.S. Cl.
CPC .......... *A61K 39/39* (2013.01); *A61K 39/0011* (2013.01); *C12N 7/00* (2013.01);
(Continued)

(58) Field of Classification Search
None
See application file for complete search history.

(56) References Cited

U.S. PATENT DOCUMENTS 4,889,803 A    12/1989    Revel et al.
5,047,335 A    9/1991    Paulson
(Continued)

FOREIGN PATENT DOCUMENTS

WO    WO 2005/087238    9/2005
WO    WO 2007/054279    5/2007
(Continued)

OTHER PUBLICATIONS

Yi et al. Single Nucleotide Polymorphisms of Human STING Can Affect Innate Immune Response to Cyclic Dinucliotides. PLoS One, 2013, 8(10): e77846; 1-16.*
(Continued)

*Primary Examiner* — Janet L Andres
*Assistant Examiner* — Stuart W Snyder
(74) *Attorney, Agent, or Firm* — Saliwanchik, Lloyd & Eisenschenk

(57) ABSTRACT

The present invention relates to methods for preparing virus-like particles comprising immunogenic cyclic dinucleotides.

21 Claims, 41 Drawing Sheets
(37 of 41 Drawing Sheet(s) Filed in Color)

(52) U.S. Cl.
CPC ........... *A61K 2039/5258* (2013.01); *A61K 2039/55555* (2013.01); *A61K 2039/55561* (2013.01); *C12N 2740/16023* (2013.01)

(56) References Cited

U.S. PATENT DOCUMENTS

| | | |
|---|---|---|
| 5,500,161 A | 3/1996 | Andrianov et al. |
| 2016/0068560 A1 | 3/2016 | Patel et al. |

FOREIGN PATENT DOCUMENTS

| | | |
|---|---|---|
| WO | WO 2011/138251 | 11/2011 |
| WO | WO 2013/185052 | 12/2013 |
| WO | WO 2014/068001 | 5/2014 |
| WO | WO 2014/099824 | 6/2014 |
| WO | WO 2014/128568 | 8/2014 |
| WO | WO 2014/179335 | 11/2014 |

OTHER PUBLICATIONS

Yang et al. HIV-1 Virus-Like Particles Produced by Stably Transfected *Drosophila* S2 Cells: a Desirable Vaccine Component. J. Virol. 2012; 86(14): 7662-7676.*

Keller et al. Cutting Edge: Limited Specialization of Dendritic Cell Subsets for MHC Class II-Associated Presentation of Viral Particles. J. Immunol. 2010; 26-29.*

Davies, B. et al. "Coordinated regulation of accessory genetic elements produces cyclic di-nucleotides for *Vibrio cholerae* virulence" *Cell*, Apr. 23, 2012, pp. 358-370, vol. 149, No. 2, and Supplemental Figures pp. 1-7.

Ablasser, A. et al., "cGAS produces a 2'-5'-linked cyclic dinucleotide second messenger that activates STING," *Nature*, Jun. 20, 2013, pp. 380-385, vol. 498.

Burdette, D.L. et al., "STING is a direct innate immune sensor of cyclic di-GMP," *Nature*, Oct. 27, 2011, pp. 515-519, vol. 478.

Chen, Q. et al., "Plant-derived virus-line particles as vaccines," *Human Vaccines & Immunotherapeutics*, 2013, pp. 26-49, vol. 9, No. 1.

Chesebro, B. et al., "Characterization of Monoclonal Antibodies Reactive with Murine Leukemia Viruses: Uses in Analysis of Strains of Friend MCF and Friend Ecotropic Murine Leukemia Virus," *Virology*, 1983, pp. 134-148, vol. 127.

Corrigan, R.M. et al., "Cyclic di-AMP: another second messenger enters the fray," *Nature Reviews Microbiology*, Aug. 2013, pp. 513-524, vol. 11.

Diner, E.J. et al., "The Innate Immune DNA Sensor cGAS Produces a Noncanonical Cyclic Dinucleotide that Activates Human STING," *Cell Reports*, May 30, 2013, pp. 1355-1361, vol. 3.

Fukata, Y. et al., "Local palmitoylation cycles define activity-regulated postsynaptic subdomains," *J. Cell Biol.*, 2013, pp. 145-161, vol. 202, No. 1.

Grgacic, E.V.L. et al., "Virus-like particles: Passport to immune recognition," *Methods*, 2006, pp. 60-65, vol. 40.

Jin, L. et al., "MPYS Is Required for IFN Response Factor 3 Activation and Type I IFN Production in the Response of Cultured Phagocytes to Bacterial Second Messengers Cyclic-di-AMP and Cyclic-di-GMP," *J Immunol*, 2011, pp. 2595-2601, vol. 187.

Kushnir, N. et al., "Virus-like particles as a highly efficient vaccine platform: Diversity of targets and production systems and advances in clinical development," *Vaccine*, 2012, pp. 58-83, vol. 31.

Lahaye, X. et al., "The Capsids of HIV-1 and HIV-2 Determine Immune Detection of the Viral cDNA by the Innate Sensor cGAS in Dendritic Cells," *Immunity*, Dec. 12, 2013, pp. 1132-1142, vol. 39.

Li, J. et al., "Exosomes mediate the cell-to-cell transmission of IFN-α-induced antiviral activity," *Nature Immunology*, Aug. 2013, pp. 793-805, vol. 14, No. 8.

Liu, F. et al., "Use of baculovirus expression system for generation of virus-like particles: Successes and challenges," *Protein Expression and Purification*, 2013, pp. 104-116, vol. 90.

Massie, J.P. et al., "Quantification of high-specificity cyclic diguanylate signaling," *PNAS*, Jul. 31, 2012, pp. 12746-12751, vol. 109, No. 31.

Naviaux, R. K. et al., "The pCL Vector System: Rapid Production of Helper-Free, High-Titer, Recombinant Retroviruses," *Journal of Virology*, Aug. 1996, pp. 5701-5705, vol. 70, No. 8.

Phillips, N.C. et al., "Enhanced antibody response to liposome-associated protein antigens: preferential stimulation of IgG2a/b production," *Vaccine*, 1992, pp. 151-158, vol. 10, No. 3.

Rehwinkel, J. et al., "SAMHD1-dependent retroviral control and escape in mice," *The EMBO Journal*, 2013, pp. 2454-2462, vol. 32, No. 18.

Rehwinkel, J. et al., "RIG-I Detects Viral Genomic RNA during Negative-Strand RNA Virus Infection," *Cell*, Feb. 5, 2010, pp. 397-408, vol. 140.

Scotti, N. et al., "Virus-like particles produced in plants as potential vaccines," *Expert Review of Vaccines*, Feb. 2013, pp. 211-224, vol. 12, Issue 2.

Sokolenko, S. et al., "Co-expression vs. co-infection using baculovirus expression vectors in insect cell culture: Benefits and drawbacks," *Biotechnology Advances*, 2012, pp. 766-781, vol. 30.

Subach, O.M. et al., "An Enhanced Monomeric Blue Fluorescent Protein with the High Chemical Stability of the Chromophore," *PLoS ONE*, Dec. 18, 2011, e28674, pp. 1-9, vol. 6, No. 12.

Sun, L. et al., "Cyclic GMP-AMP Synthase Is a Cytosolic DNA Sensor That Activates the Type I Interferon Pathway," *Science*, Feb. 15, 2013, pp. 786-791, vol. 339.

Unkeless, J.C. et al., "Structure and Function of Human and Murine Receptors for IgG," *Ann. Rev. Immunol.*, 1988, pp. 251-281, vol. 6.

Vincente, T. et al., "Large-scale production and purification of VLP-based vaccines," *Journal of Invertebrate Pathology*, 2011, pp. S42-S48, vol. 107.

Woodward, J.J. et al., "c-di-AMP Secreted by Intracellular *Listeria monocytogenes* Activates a Host Type I Interferon Response," *Science*, Jun. 25, 2010, pp. 1703-1705, vol. 328.

Wu, J. et al., "Cyclic GMP-AMP Is an Endogenous Second Messenger in Innate Immune Signaling by Cytosolic DNA," *Science*, Feb. 15, 2013, pp. 826-830, vol. 339.

Wu, X. et al., "Molecular evolutionary and structural analysis of the cytosolic DNA sensor cGAS and STING," *Nucleic Acids Research*, Jun. 12, 2014, pp. 8243-8257, vol. 42, No. 13.

Zeltins, A., "Construction and Characterization of Virus-Like Particles: A Review," *Mol Biotechnol*, 2013, pp. 92-107, vol. 53.

Zimmermann, P. et al., "Characterization of Syntenin, a Syndecan-binding PDZ Protein, as a Component of Cell Adhesion Sites and Microfilaments," *Molecular Biology of the Cell*, Feb. 2001, pp. 339-350, vol. 13.

Satoh, T. et al., "Gene Transduction in Human Monocyte-Derived Dendritic Cells Using Lentiviral Vectors," *Methods Mol Biol*, 2013, pp. 401-409, vol. 960.

Uzé, G. et al., "Domains of Interaction between Alpha Interferon and its Receptor Components," *J Mol Biol*, 1994, pp. 245-257, vol. 243.

Allison, A.C. "The mode of action of immunological adjuvants" *Developments in Biological Standardization*, 1998, pp. 3-11, vol. 92, abstract only.

Bridgeman, A. et al. "Viruses transfer the antiviral second messenger cGAMP between cells" *Science*, Sep. 11, 2015, pp. 1228-1232, vol. 349, No. 6253.

Gentili, M. et al. "Transmission of innate immune signaling by packaging of cGAMP in viral particles" *Science*, Sep. 11, 2015, pp. 1232-1236, vol. 349, No. 6253.

* cited by examiner

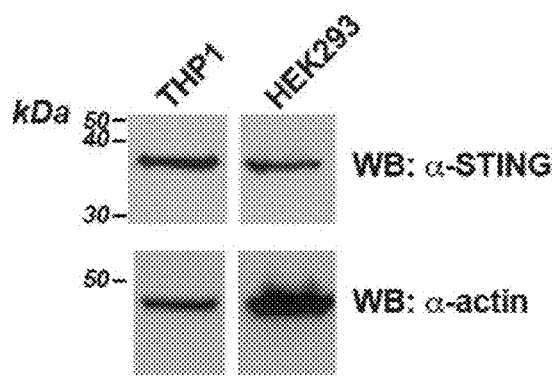
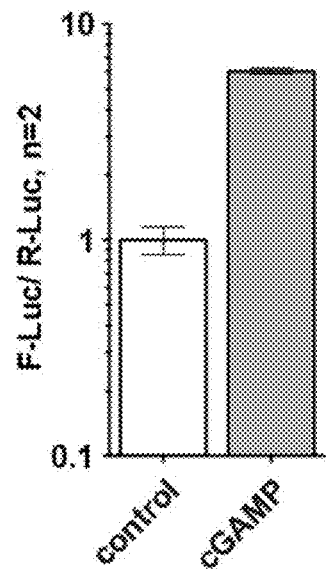
FIGURE 2A
FIGURE 2B
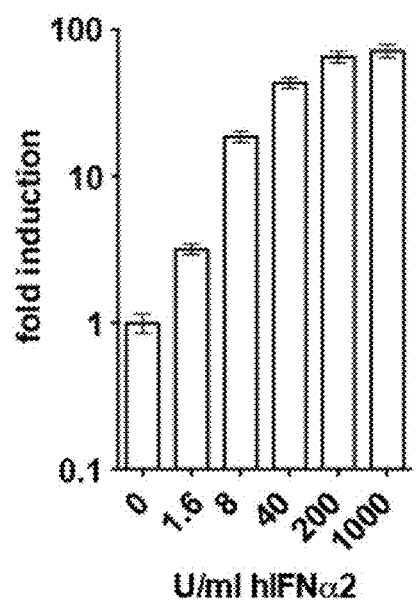
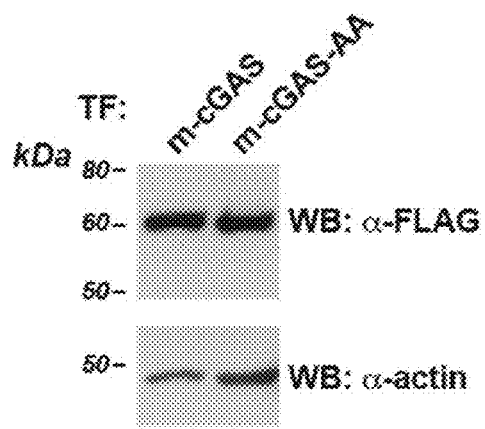
FIGURE 2C
FIGURE 2D

FIGURE 3E

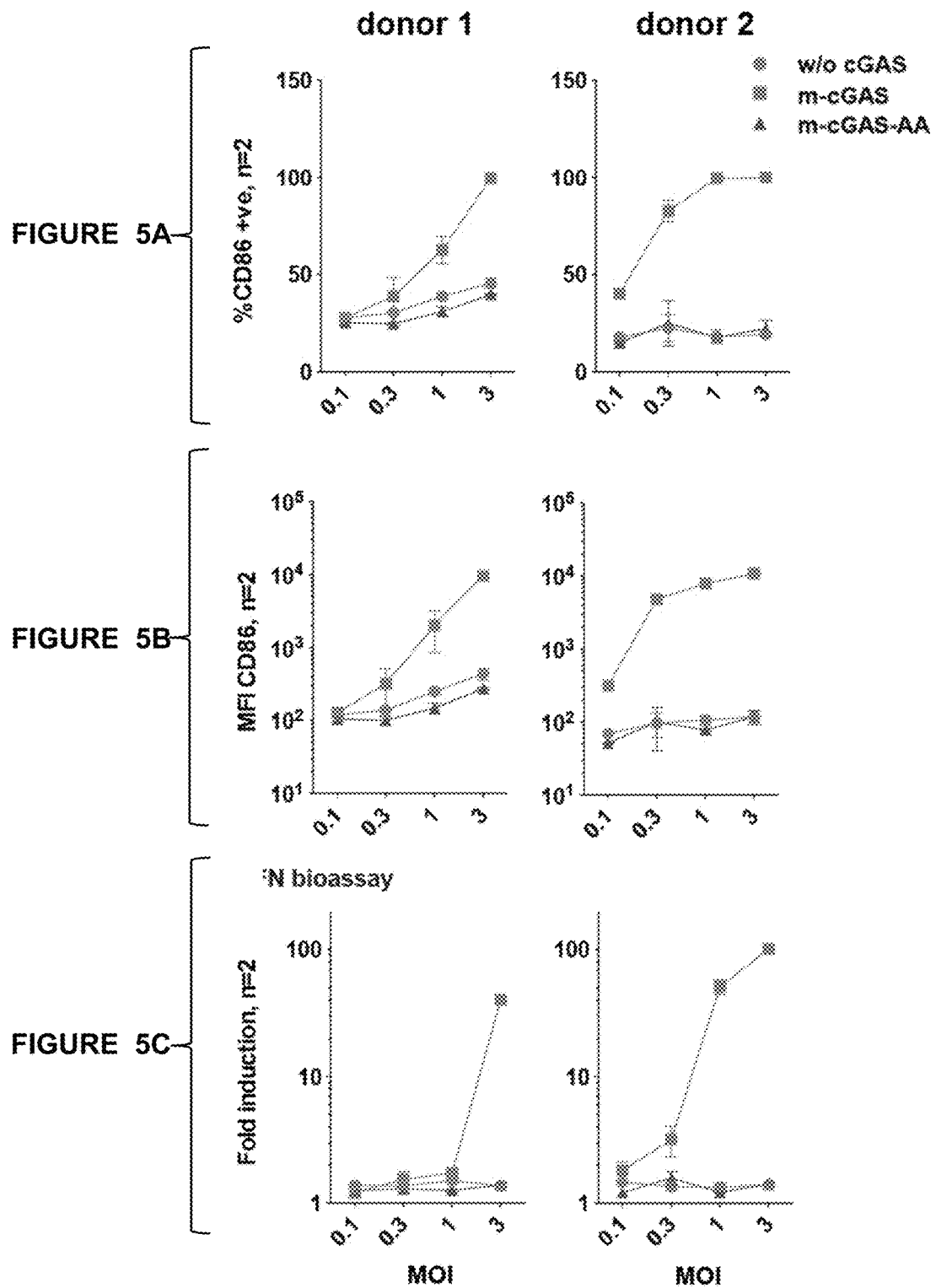

| 1- | dose 1 | Ova-cGAMP-VLP | |
| 2- | dose 1/3 | Ova-cGAMP-VLP | |
| 3- | dose 1/9 | Ova-cGAMP-VLP | |
| 4- | dose 1 | cGAMP-VLP | |
| 5- | 20μg | Ova protein | +10μg cGAMP |
| 6- | 20μg | Ova protein | +40μg CpG |
| 7- | | PBS | | ary of the Invention (cont.)

METHOD FOR PREPARING VIRAL PARTICLES WITH CYCLIC DINUCLEOTIDE AND USE OF SAID PARTICLES FOR INDUCING IMMUNE RESPONSE

CROSS-REFERENCE TO RELATED APPLICATION

This application claims the benefit of U.S. Provisional Application Ser. No. 62/051,016, filed Sep. 16, 2014, the disclosure of which is hereby incorporated by reference in its entirety, including all figures, tables and amino acid or nucleic acid sequences.

The Sequence Listing for this application is labeled "Seq-List.txt" which was created on Sep. 14, 2015 and is 9 KB. The entire content of the sequence listing is incorporated herein by reference in its entirety.

FIELD OF THE INVENTION

The present invention relates to the field of medicine, in particular of vaccine.

BACKGROUND OF THE INVENTION

Cyclic dinucleotides have recently been described as potent cytosolic adjuvants of the immune system. They induce an antiviral innate immune response such as against HIV (Human Immunodeficiency Virus) and HSV (Herpes simplex virus), and also against cancer (WO2005/087238; WO2007/054279; WO2013/185052). Cyclic dinucleotides were previously identified in bacteria and known to be immunostimulatory.

This field has recently gained a lot of attention following the identification that a cyclic dinucleotide, cGAMP (2'-3'-cyclic GMP-AMP), also exists in vertebrates and can be endogenously synthetized by the enzyme cGAS upon recognition of cytosolic DNA.

Cyclic GMP-AMP synthase (cGAS) is a cytosolic DNA sensor that signals by catalyzing the synthesis of a second messenger, cGAMP. cGAS binds double-stranded DNA in a sequence non-specific manner and this induces a conformational change in its enzymatic site allowing for cyclic GMP-AMP (cGAMP) synthesis ((Wu et al., 2012, Science, 339, 826-830; Sun et al., 2012, Science, 339, 786-791; WO2014/099824; Ablasser et al., 2013, Nature, 498, 380-384). Metazoan cGAMP bears both a canonical 3'-5' and an unusual 2'-5' phosphodiester bond. cGAMP binds and activates stimulator of interferon genes (STING). STING plays a central role in cytosolic DNA sensing by relaying a signal from upstream DNA sensors to activate transcription factors such as IRF3, which in turn drive IFN gene transcription. Interferons (IFN) play pivotal roles in the immune response to virus infection. IFN expression is induced by signaling pathways activated by sensors of virus presence, including cytosolic DNA sensors.

However, cyclic dinucleotides do not efficiently cross the plasma membranes of cells and have a limited potency when used without vectors. Current vectors mainly consist of lipid-based complexes such as lipofectamine, which have limited use in vivo due to their toxicity.

Therefore, there is a strong need for a vectorization means of cyclic dinucleotides, especially the promising cGAMP.

SUMMARY OF THE INVENTION

The present invention provides a new vectorization of cyclic dinucleotides, especially cGAMP, using enveloped virus-like particles. Indeed, cyclic dinucleotides, especially cGAMP, can be packaged into enveloped virus-like particles (VLPs) or virions and induce an innate immune response, in particular an interferon response, upon infection of cells. More particularly, in order to be able to vectorize cyclic dinucleotides, especially cGAMP, the VLPs need to be enveloped so as to optimize the delivery of cyclic dinucleotides, especially cGAMP, by fusion of VLP with the target cells.

The present invention relates to a virus-like particle comprising a lipoprotein envelope including a viral fusogenic glycoprotein, wherein said virus-like particle contains cyclic dinucleotides packaged into said virus-like particle. Preferably, the virus-like particle further comprises a capsid from retroviridae.

Preferably, the viral fusogenic glycoprotein is a glycoprotein from retroviridae (including lentivirus and retrovirus), herpesviridae, poxviridae, hepadnaviridae, flaviviridae, togaviridae, coronaviridae, hepatitis D virus, orthomyxoviridae, paramyxoviridae, filoviridae, rhabdoviridae, bunyaviridae, or orthopoxiviridae (e.g., variola), preferably from orthomyxovirus, retroviruses, or rhabdovirus. In particular, the viral fusogenic glycoprotein can be a glycoprotein from HIV (Human Immunodeficiency Virus), including HIV-1 and HIV-2; influenza, including Influenza A (e.g., subtypes H5N1 and H1N1) and Influenza B; thogotovirus; or VSV (Vesicular Stomatitis Virus).

Preferably, the retroviral capsid is from retroviridae, preferably lentivirus and retrovirus. More preferably, the retroviral capsid is from HIV or MLV (Murine Leukemia Virus).

Preferably, the cyclic dinucleotides are selected from the group consisting of cyclic di-adenosine monophosphate (c-di-AMP), cyclic di-guanosine monophosphate (c-di-GMP), and cyclic guanosine monophosphate-adenosine monophosphate (cGAMP). More preferably, the cyclic dinucleotides are cGAMP (2'-3'-cyclic GMP-AMP) or cGAMP (3'-3'-cyclic GMP-AMP).

Optionally, the virus-like particle of the invention may further comprise an antigen or any other protein or nucleic acid of interest.

The present invention relates to the virus-like particle as disclosed herein as a drug, especially a vaccine, or a vaccine adjuvant. It also relates to a pharmaceutical, vaccine or veterinary composition comprising a virus-like particle as disclosed herein, a pharmaceutically acceptable carrier and optionally an antigen or a therapeutic active agent.

The present invention further relates to a method for inducing or enhancing an immune response in a subject comprising administrating a virus-like particle as disclosed herein or a composition as disclosed herein. It also relates to a method for preventing or treating an infectious disease, in particular a viral infection, or a cancer in a subject comprising administrating a virus-like particle as disclosed herein or a composition as disclosed herein. It relates to a virus-like particle or a composition as disclosed herein for use for preventing or treating an infectious disease, in particular a viral infection, or a cancer in a subject. It relates to the use of a virus-like particle or a composition as disclosed herein for the manufacture of a medicament or vaccine for preventing or treating an infectious disease, in particular a viral infection, or a cancer in a subject.

In another aspect, the present invention relates to an expression vector or a combination of expression vectors, comprising a sequence encoding a cyclic dinucleotide synthase and either a sequence encoding a viral fusogenic glycoprotein or a sequence encoding retroviridae capsid protein, or both. Preferably, the expression vector comprises a sequence encoding a cyclic dinucleotide synthase and both a sequence encoding a viral fusogenic glycoprotein and a sequence encoding retroviridae capsid protein.

Preferably, the cyclic dinucleotide synthase is selected from the group consisting of the diadenylate cyclase, diguanylate cyclase and the cyclic GMP-AMP synthase. More preferably, it is cGAS (Cyclic GMP-AMP synthase).

Optionally, the expression vector may further comprise a sequence encoding an antigen or any other protein or nucleic acid of interest, in particular a therapeutic active agent.

Preferably, the expression vector is a plasmid, a baculovirus vector or a viral vector. More preferably, the viral vector is selected from the group consisting of an adenoviral vector, an adeno-associated virus-based vector, and a lentiviral vector.

The present invention further relates to the expression vector or combination thereof as disclosed herein as a drug, especially a vaccine, or a vaccine adjuvant. It also relates to a pharmaceutical, vaccine or veterinary composition comprising an expression vector or combination thereof as disclosed herein and a pharmaceutically acceptable carrier.

The present invention also relates to a method for inducing or enhancing an immune response in a subject, comprising administering an expression vector or combination thereof as disclosed herein or a composition pharmaceutical, vaccine or veterinary composition comprising such vectors. It relates to a method for preventing or treating an infectious disease or a cancer in a subject, comprising administering an expression vector or combination thereof as disclosed herein or a composition pharmaceutical, vaccine or veterinary composition comprising such vectors. It relates to an expression vector or combination thereof as disclosed herein or a composition pharmaceutical, vaccine or veterinary composition comprising such vectors for use for preventing or treating an infectious disease, in particular a viral infection, or a cancer in a subject. It relates to the use of an expression vector or combination thereof as disclosed herein or a composition pharmaceutical, vaccine or veterinary composition comprising such vectors for the manufacture of a medicament or vaccine for preventing or treating an infectious disease, in particular a viral infection, or a cancer in a subject.

Another aspect of the present invention is a recombinant eukaryotic host cell comprising a sequence encoding a cyclic dinucleotide synthase and a sequence encoding a viral fusogenic glycoprotein or a sequence encoding retroviridae capsid protein or both.

Preferably, the cyclic dinucleotide synthase is selected from the group consisting of the diadenylate cyclase, diguanylate cyclase and the cyclic GMP-AMP synthase. More preferably, it is cGAS (Cyclic GMP-AMP synthase).

Preferably, the recombinant eukaryotic host cell comprises a sequence encoding a cyclic dinucleotide synthase and both a sequence encoding a viral fusogenic glycoprotein and a sequence encoding retroviridae capsid protein.

Optionally, the recombinant eukaryotic host cell may further comprise a sequence encoding an antigen or any other protein or nucleic acid of interest.

In a first aspect, one or several sequences selected from the sequence encoding the cyclic dinucleotide synthase, the viral fusogenic glycoprotein and the sequence encoding retroviridae capsid protein are episomal. Alternatively, one or several sequence selected from the sequence encoding the cyclic dinucleotide synthase, the viral fusogenic glycoprotein and the sequence encoding retroviridae capsid protein are integrated into the host cell chromosome.

The present invention also relates to the recombinant eukaryotic host cell as disclosed herein as a drug or a vaccine adjuvant. It relates to a method for inducing or enhancing an immune response in a subject comprising administering a recombinant eukaryotic host cell as disclosed herein. It also relates to a method for preventing or treating an infectious disease or a cancer in a subject comprising administering a recombinant eukaryotic host cell as disclosed herein.

The present invention further relates to a method for preparing a virus-like particle comprising cyclic dinucleotides packaged into said virus-like particle, wherein the method comprises:

co-expression of a cyclic dinucleotide synthase and a viral fusogenic glycoprotein in a eukaryotic cell in conditions allowing the synthesis of cyclic dinucleotides and the viral fusogenic glycoprotein in said cell; and recovering of the virus-like particles produced by said cell.

Preferably, the cyclic dinucleotide synthase is selected from the group consisting of the diadenylate cyclase, diguanylate cyclase and the cyclic GMP-AMP synthase. More preferably, it is cGAS (Cyclic GMP-AMP synthase).

Preferably, said cell further expresses a capsid from retroviridae.

Preferably, the viral fusogenic glycoprotein is a glycoprotein from retroviridae (including lentivirus and retrovirus), herpesviridae, poxviridae, hepadnaviridae, flaviviridae, togaviridae, coronaviridae, hepatitis D virus, orthomyxoviridae, paramyxoviridae, rhabdoviridae, bunyaviridae, filoviridae, and orthopoxiviridae (e.g., variola), preferably from orthomyxovirus, retroviruses, and rhabdovirus. More particularly, the viral fusogenic glycoprotein can be a glycoprotein from HIV (Human Immunodeficiency Virus), including HIV-1 and HIV-2; influenza including Influenza A (e.g., subtypes H5N1 and H1N1) and Influenza B; thogotovirus; and VSV (Vesicular Stomatitis Virus).

Preferably, the retroviral capsid is from retroviridae, preferably lentivirus and retrovirus, preferably from HIV or MLV (Murine Leukemia Virus).

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

Figure 1A:
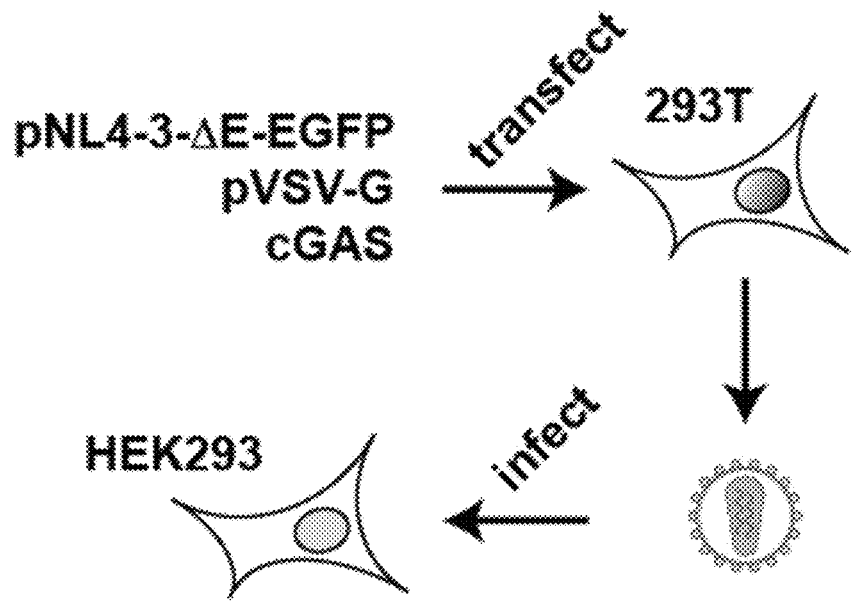
FIGS. 1A-1F. HIV-1-GFP produced in cGAS-reconstituted 293T cells induces IFN in infected cells. (A) Schematic of the experimental setup. (B) HEK293 cells were transfected with the IFNβ promoter reporter (p125-F-Luc) and pRL-TK as a control. After 6-8 hours, cells were infected (MOI=1) with HIV-1-GFP from producer cells expressing cGAS as indicated or were left uninfected. F-Luc activity was analyzed after 24 hours and normalized to R-Luc. m-cGAS-AA is a catalytically inactive mutant. (C) HIV-1-GFP infected cells were washed after 24 hours and after an additional 48 hours, IFN in the supernatant was analyzed by bioassay (left) and cells were collected for FACS analysis. The percentage of GFP positive cells is shown (right). Wedges represent MOIs of 10, 5, 2, 1, 0.5 and 0.1. (D) RNA was extracted from cells infected as in (C) (MOI=1). The indicated mRNAs were quantified relative to 18S rRNA by RT Q-PCR. (E) BMDMs of the indicated genotypes were infected with HIV-1-GFP (MOI=5) or Sendai virus (SeV, wedges represent MOIs of 1, 0.5 and 0.1). Supernatant was tested after 24 hours for mIFNα by ELISA.

n.d., not detectable. (F) BMDMs were infected as in (E) and the indicated mRNAs were quantified relative to GAPDH mRNA by RT Q-PCR. Black wedges represent MOIs of 5 and 1 and grey wedges MOIs of 1, 0.5 and 0.1. Bars show the average of two (B,D,E) or four (C,F) replicates and error bars represent the range (B,D,E) or standard deviation (C,F).

FIGS. 2A-2F. HEK293 cells express STING and induce IFN in response to cGAMP. (A) Cell extracts from THP1 and HEK293 cells were tested by Western blot for STING expression. An irrelevant intervening lane was spliced out during preparation of the figure. (B) $2 \times 10^5$ HEK293 cells were transiently transfected with the IFNβ promoter reporter (p125-F-Luc) and with pRL-TK as a control. After 24 hours, cells were transfected with 2 μg 2'-3'-cGAMP or with lipofectamine only (control). Luciferase activity was analyzed after 24 additional hours and F-Luc activity is shown normalized to R-Luc. Bars show the average of two replicates and error bars represent the range.

IFN bioassay. (C) HEK293 cells were transduced with pGreenFire-ISRE using lentiviral delivery. Clones were obtained by serial dilution and, based on the responses to IFN, clone 3C11 was selected. 25,000 3C11 cells were seeded in 96-well plates and recombinant human IFNα2 was added. After 24 hours, cells were lysed and firefly luciferase activity was measured. Background bioluminescence in untreated cells was set to 1. Bars show the average of two replicates and error bars represent the range.

Wild-type and mutant cGAS are expressed equally in virus producer cells. (D) 293T virus producer cells were lysed 72 hours after transfection and cGAS protein levels were determined by Western blot using a monoclonal antibody recognizing the FLAG-tag.

Adenovirus-GFP (Ad-GFP) produced in cGAS-reconstituted cells does not trigger IFN in freshly infected target cells. (E) Ad-GFP was produced in HEK293 cells. Some virus producer cells were co-transfected with cGAS expression constructs. Virus stocks were then used to infect fresh HEK293 cells. Wedges represent 0.01 and 0.001 μl inoculum. IFN production by Ad-GFP infected cells was tested by bioassay. Recombinant IFNα at the indicated doses was used to demonstrate the responsiveness of the bioassay. Bars show the average of two replicates and error bars represent the range. (F) Infection was monitored by FACS.

FIGS. 3A-3F. IFN induction triggered by HIV-1-GFP from cGAS expressing cells is independent of viral nucleic acids. (A) Virus stocks were treated or not with DNase I and then used to infect cells as in FIG. 1 (MOI=1). As controls, medium and m-cGAS plasmid were incubated with DNase I and then added to cells or transfected, respectively. (B) HIV-1-GFP was collected from producer cells transfected as indicated (supernatant, SUP). HIV-1-GFP was pelleted from an aliquot by centrifugation and resuspended in fresh medium (pelleted, PEL). Cells were then infected (MOI=1). (C) Cells were infected (MOI=1) in the presence of nevirapine (Nev) or raltegravir (Ral). The percentage of infected cells was determined by FACS (right). (D) Cells were infected with 100, 50 or 5 μl (wedges) supernatant from cells producing HIV-1-GFP or virus-like particles (VLPs). (E) HIV-1-GFP was pseudotyped with VSV-G or THOV-G and supernatants (VSV-G: 1 and 0.1 μl; THOV-G: 100 and 10 μl) from producer cells were used to infect cells. (F) HIV-1-GFP was produced in cells reconstituted with m-cGAS that were also treated with 20 μM GW4869 or 60 μM Ac-DEVD-CHO or were left untreated (control). Fresh cells were infected with 10, 1 or 0.1 μl (wedges) supernatant. In all panels, cells were infected for 24 hours, washed and after an additional 48 hours, IFN in the supernatant was analyzed by bioassay. Bars show the average of two (B,C,D,E), three (F) or four (A) replicates and error bars represent the range (B,C,D,E) or standard deviation (A,F).

FIGS. 4A-4D. Small molecule extracts from HIV-1-GFP from cGAS-reconstituted producer cells induce IFN. (A) Schematic of the experimental setup. (B) Extracts from viruses produced in the absence of cGAS (first set of bars) or in the presence of wild-type or mutant cGAS (second and third sets of bars) were added to digitonin permeabilized THP1 cells. IFN in THP1 supernatants was assessed by bioassay. Gray wedges represent a 1:2 dilution series starting with extract from $10^7$ infectious units. As controls, synthetic cGAMP was either directly added to THP1 cells (last set of bars) or was spiked into medium and then included in the extraction procedure (fourth set of bars). Black wedges represent a 1:3 dilution series starting with 50 ng cGAMP. (C) Extract from $10^7$ infectious units HIV-1-GFP produced in the presence of cGAS was incubated with or without SVPDE for 1 hour and then added to digitonin permeabilized THP1 cells. IFN in THP1 supernatants was assessed by bioassay. Wedges represent a 1:3 dilution series. (D) HIV-1-GFP produced in the absence or presence of cGAS or in biotin-cGAMP transfected cells was probed by dot blot for biotin (left). The stripped membrane was then re-probed for p24 (right). Wedges represent a 1:10 dilution series starting with $2 \times 10^6$ infectious units.

FIGS. 5A-5C. Infection of dendritic cells with HIV-1-GFP from cGAS-reconstituted producer cells induces CD86 expression and IFN secretion. Human dendritic cells derived from monocytes from two donors were infected with HIV-1-GFP at the indicated MOIs. After 48 hours, CD86 expression was analyzed by FACS. (A) The percentage of CD86+ cells is shown. (B) The CD86 median fluorescence intensity is shown. (C) Supernatant was tested in the IFN bioassay. (A-C) Average data from duplicate infections for each donor are shown; error bars represent the range. Note that these effects were observed in the absence of Vpx.

FIGS. 6A-6E. cGAS lentiviral vector activates dendritic cells. (A) BFP and CD86 expression after infection of monocytes with a lentivirus coding BFP-2A or BFP-2A-cGAS, in presence or absence of Vpx. (B) CD86 expression as in (A) with titrated virus without Vpx and statistical analysis on top dose (paired t test; n=4; *p<0.001). (C) IP-10 production as in (A) with titrated virus without Vpx and statistical analysis on top dose (paired t test; n=4; p<0.01 on log-transformed data). (D) BFP and CD86 expression after infection of monocytes with a lentivirus coding BFP-2A or BFP-2A-cGAS, or with VLPs produced in presence of a non-lentiviral plasmid encoding for cGAS (PSTCD-cGAS). (E) CD86 expression and IP-10 production as in (D) (n=5, paired t test for CD86 expression analysis, paired t test on log-transformed data for IP-10; *p<0.001, p<0.01, ns=non-significant).

FIGS. 7A-7D. cGAS lentiviral vectors activate monocyte and fully differentiated dendritic cells. (A) CD14 and DC-SIGN expression 96 h after transduction of monocytes with a BFP coding vector and a cGAS coding vector in absence of Vpx followed by differentiation in DCs with GM-CSF and IL-4 (n=2). (B) BFP and CD86 expression 48 h post infection of established monocyte-derived dendritic cells with a BFP-2A lentivirus and a BFP-2A-cGAS lentivirus. (C) CD86 expression as in (B) (n=3). (D) Immunoblotting of Gag, cGAS and actin in the producer cells and in the pelleted supernatant used in FIG. 6D.

FIGS. 8A-8E. HIV particles transfer an innate signal initiated by cGAS. (A) BFP and CD86 expression after infection of monocytes with a lentivirus produced with the BFP-2A-cGAS vector, Gag/Pol and VSV-G. Cells were infected with complete supernatant or the retentate and filtrate after filtration with a 10 kDa cutoff. A representative experiment out of four is shown. (B) CD86 expression and IP-10 production in dose response infections of monocytes with differentially fractionated supernatants containing VLPs produced from 293FT expressing wild-type cGAS or an inactive cGAS mutant lacking the DNA Binding Domain (ΔDBD). The volume of each fraction used for infection and the corresponding concentration factor compared to the initial supernatant are indicated (n=3; mean and SEM plotted). (C) Immunoblotting of Gag and cGAS in the fractions obtained by differential centrifugations of the complete supernatant as in (B) (representative of three experiments). (D) Immunoblotting of the exosome markers syntenin-1, CD63, CD81 and CD9 in the fractions obtained by differential centrifugations of the complete supernatant as in (B) (representative of three experiments). (E) CD86 expression analysis of the experiment in (A) (n=4; paired t test; **p<0.01, ns=non-significant).

Figure 9A:
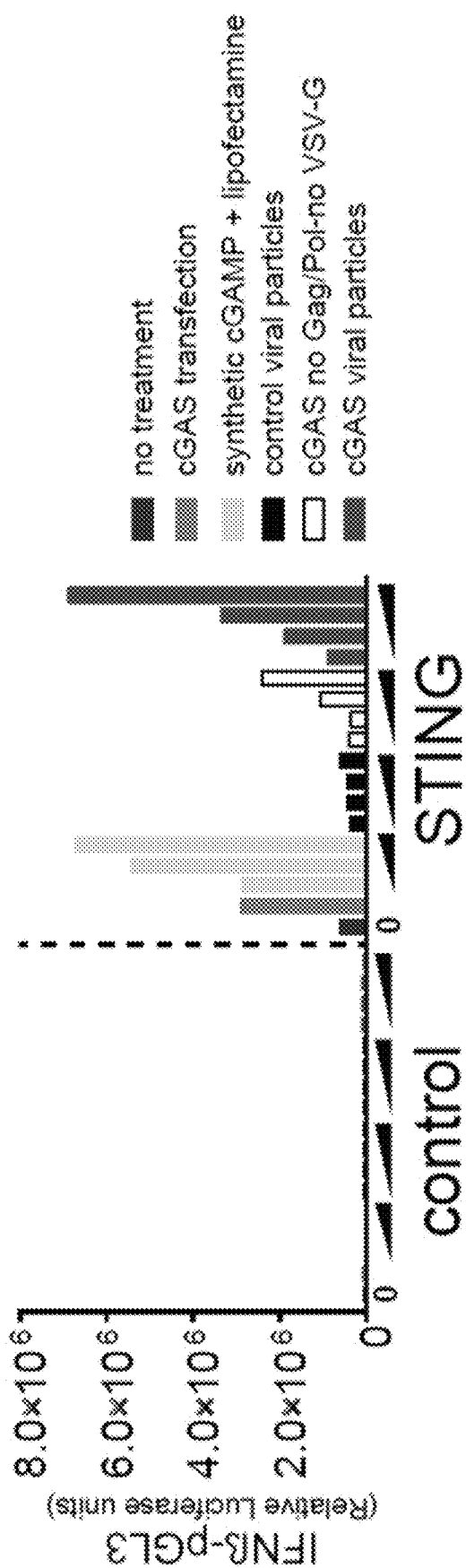
Figure 9B:
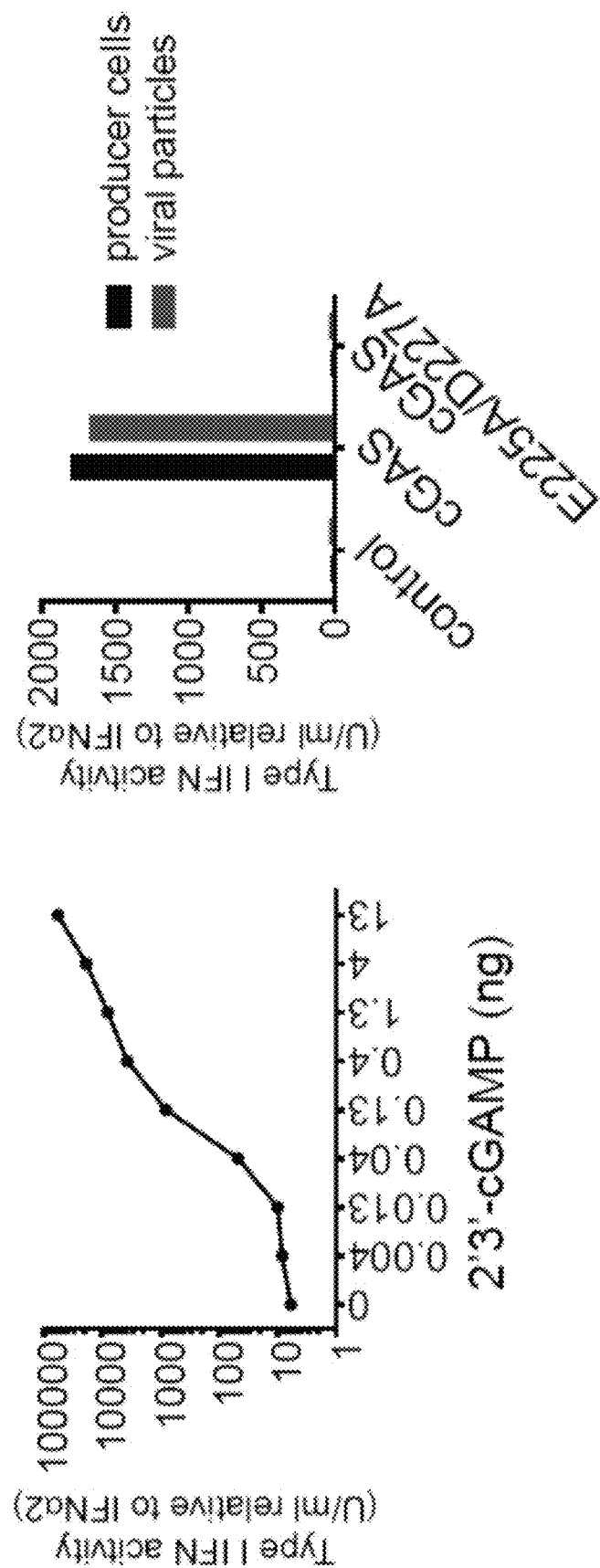
Figure 9C:
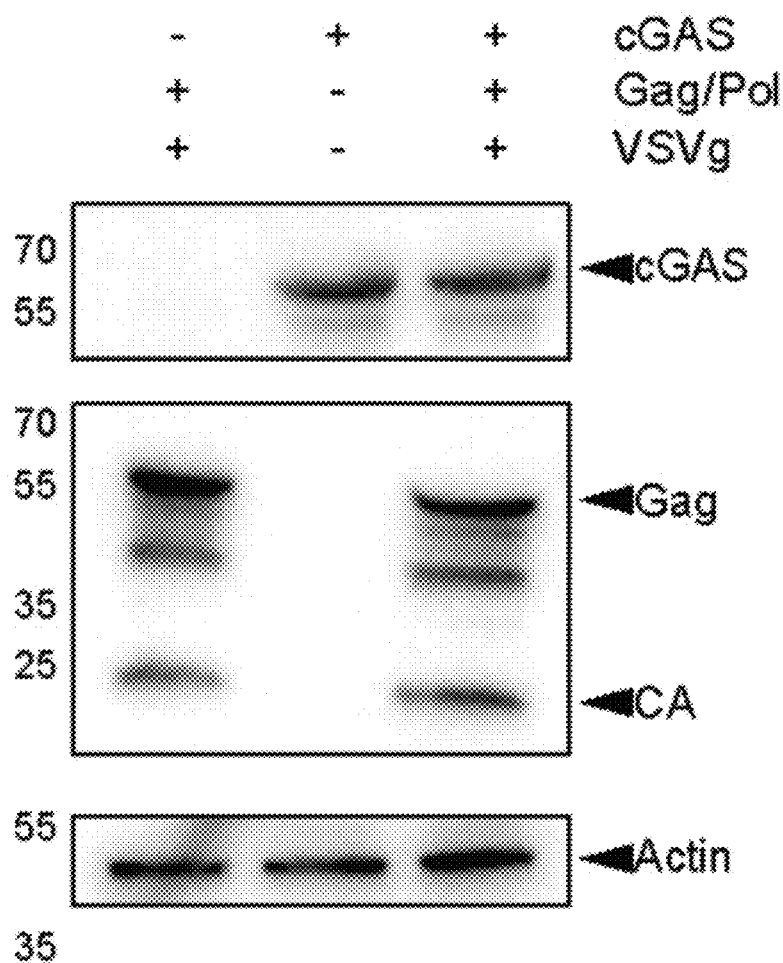

FIGS. 9A-9C. Viral particles package and transfer cGAMP. (A) 293FT cells transfected with a Luciferase reporter plasmid under control of the IFNβ promoter with or without a STING coding plasmid. The cells were either stimulated with titrated amounts of supernatants from cells producing viral particles in presence (cGAS viral particles) or absence (control viral particles) of murine cGAS and supernatants from cells expressing murine cGAS (cGAS no Gag/Pol no VSV-G), stimulated with synthetic cGAMP using lipofectamine or transfected with a plasmid coding for cGAS (cGAS transfection). One representative experiment out of three independent experiments is shown. (B) Type I IFN activity measured after exposure of permeabilized PMA-differentiated THP-1 cells to synthetic 2'-3'-cGAMP (left panel) or to the benzonase-resistant extracts coming from 293FT transfected cells and pelleted viral particles. 293FT cells were transfected with a lentiviral packaging plasmid in presence of cGAS or of the catalytically inactive mutant E225A/D227A (right panel). One representative experiment out of three independent experiments is shown. (C) Immunoblotting of Gag, cGAS and actin in the VLP producer cells used in (A).

FIGS. 10A-10F. cGAMP transfer by viral particles is a conserved property of retroviruses. (A) BFP and CD86 expression in DCs after exposure of monocytes to cell-free supernatants of cells transfected with combinations of plasmids expressing Gag/Pol and VSV-G together with plasmids coding cGAS, cGAS E225A/D227A or control. (B) Analysis of CD86 expression and IP-10 production as in (A) (n=6; paired t test for CD86 expression, paired t test on log transformed data for IP-10 production, **p<0.0001, *p<0.001, **p<0.01, *0.01<p<0.05). (C) Immunoblotting of Gag, VSV-G, cGAS and actin in the producer cells and in the pelleted cell-free supernatants. (D) CD86 expression and IP-10 production in DCs after infection of monocytes with lentiviral particles pseudotyped with Influenza H1N1 (left panel) or H5N1 (right panel) envelope proteins and produced in presence or absence of murine cGAS (n=4; analysis as in (B)). (E) CD86 expression and IP-10 production in DCs after infection of monocytes with gammaretroviral particles produced with MLV 10A1 Gag/Pol and pseudotyped with VSV-G in presence or absence of cGAS (n=4; analysis as in (B)). (F) CD86 expression and IP-10 production in DCs after infection in presence of AZT of monocytes with CCR5-tropic HIV-1 viral particles produced in presence or absence of murine cGAS (n=4; analysis as in (B)).

FIGS. 11A-11E. Lentiviral mediated cGAMP transfer is mediated by various fusogenic envelope glycoproteins (A) CD86 expression and IP-10 production in DCs after infection of monocytes with titrated doses of lentiviral particles pseudotyped with Influenza (left panel) or H5Na (right panel) envelope proteins and produced in absence or presence of cGAS (n=4). (B) CD86 expression and IP-10 production in DCs after infection of monocytes with titrated doses of gammaretroviral particles produced with MLV 10A1 Gag/Pol and pseudotyped with VSV-G in presence or absence of cGAS (n=4). (C) CD86 expression and IP-10 production in DCs after infection of monocytes in presence of AZT with CCR5-tropic HIV-1 viral particles produced in presence or absence of cGAS. (D) Immunoblotting of MLV Gag, VSV-G, cGAS and actin in producer cells and pelleted supernatant. (E) Immunoblotting of HIV-1 Gag, VSV-G, cGAS and actin in producer cells and pelleted supernatant.

Figure 12:
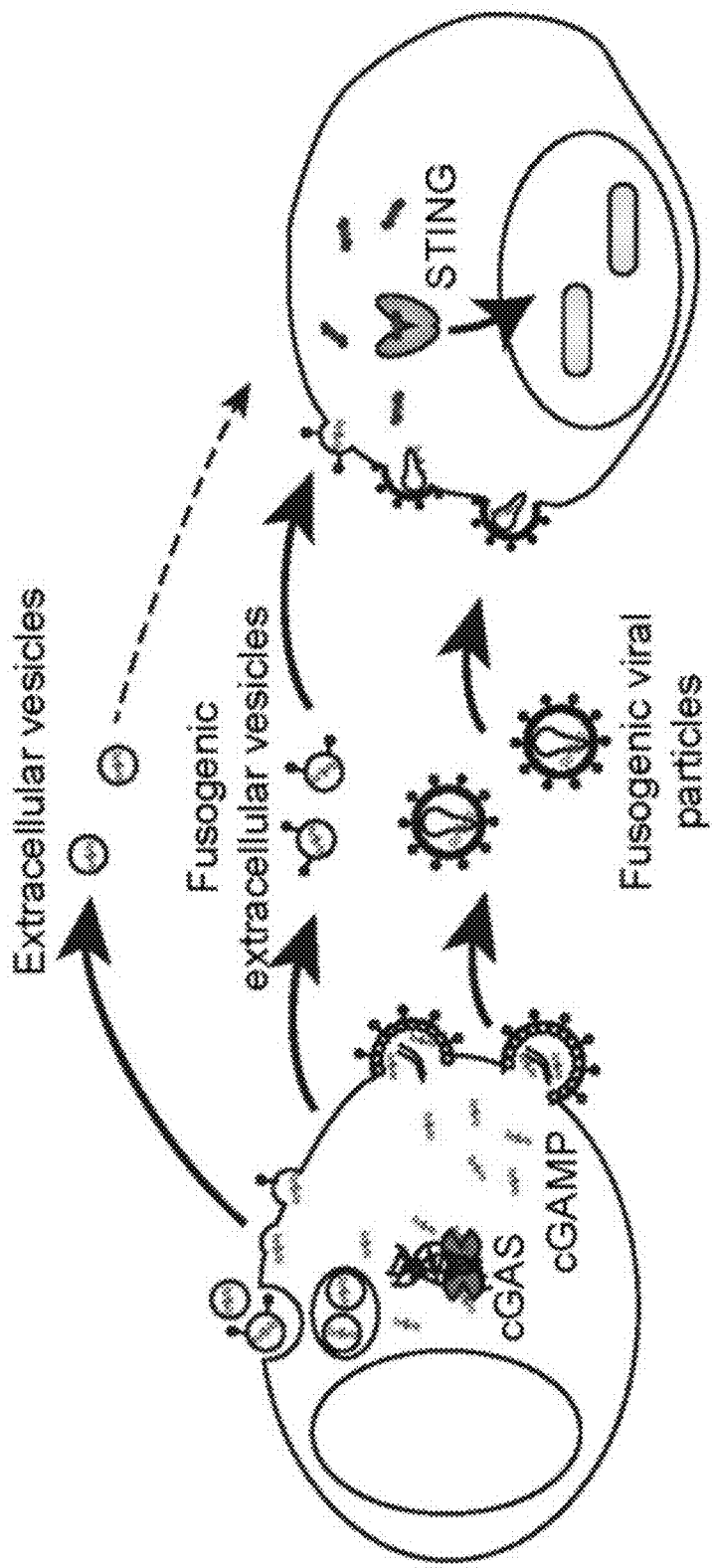

FIG. 12. Model for the viral-mediated transfer of cGAMP between cells. In virus-producing cells, cGAS produces cGAMP. cGAMP is packaged into extracellular vesicles and viral particles. Viral particles can efficiently fuse with cellular membranes and deliver cGAMP to the cytosol of target cells. cGAMP in turn activates STING and induces an innate immune response. Extracellular vesicles can also package cGAMP, but the efficiency of target cell activation is less than fusogenic viral particles.

Figure 13A:
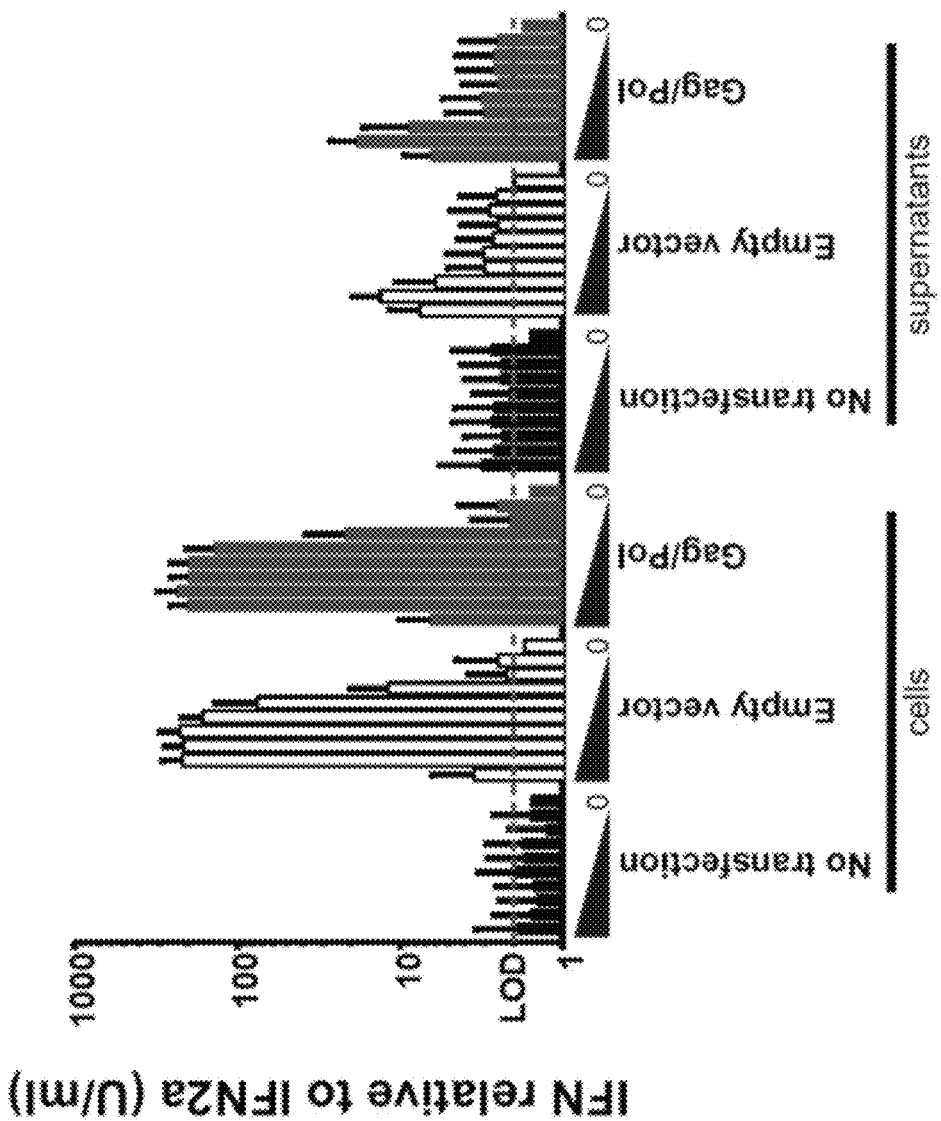
Figure 13B:
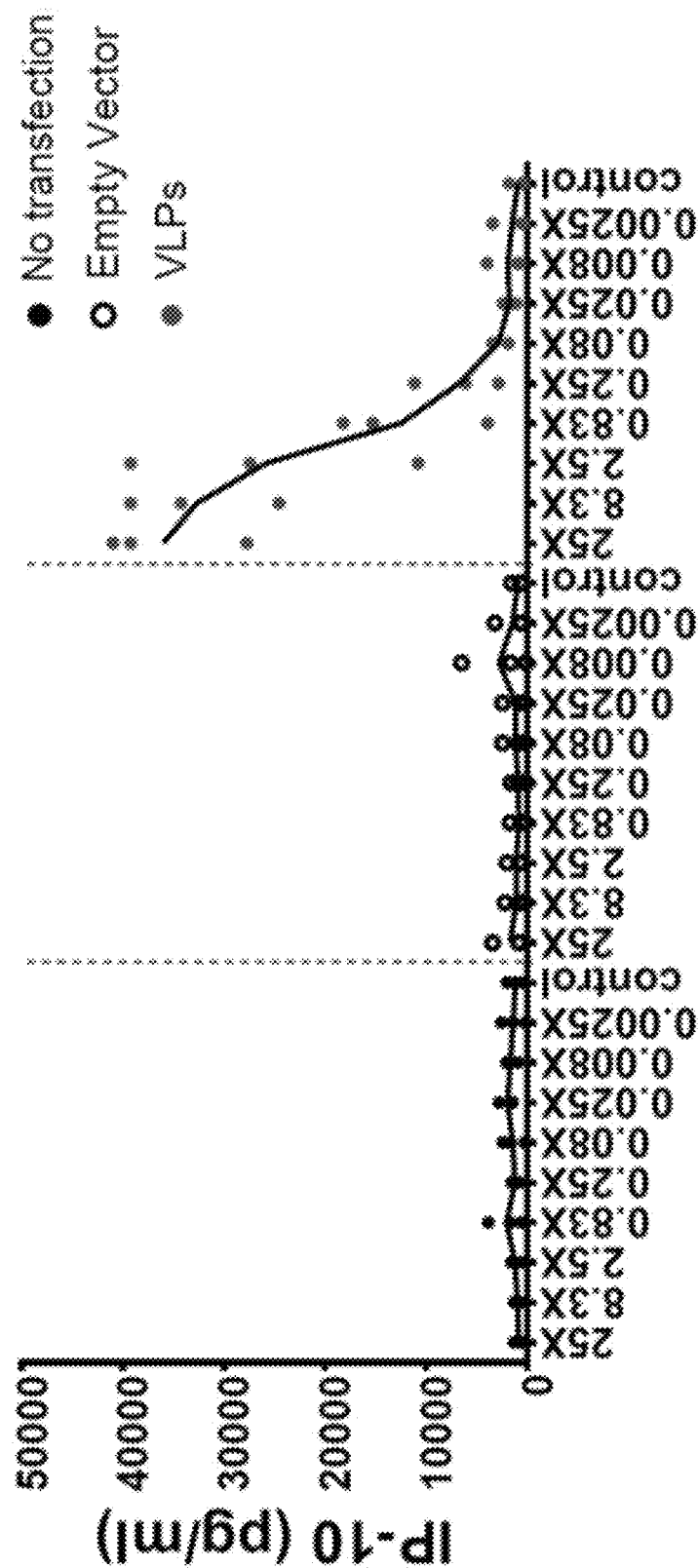
Figure 13C:
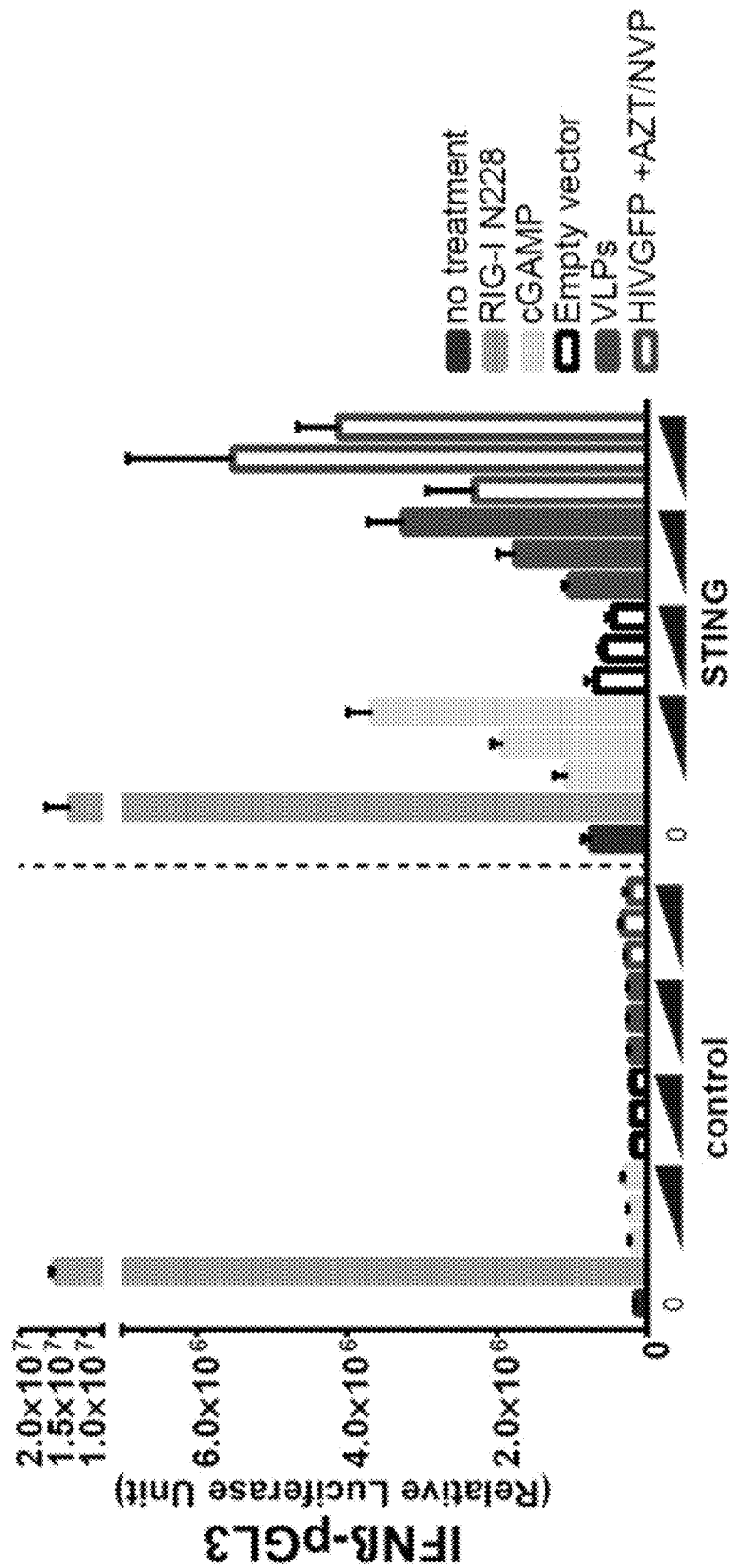

FIGS. 13A-13C. cGAMP transfer by viral particles occurs at a physiologically relevant level of cGAS expression. (A) Type I IFN activity measured after exposure of permeabilized PMA-treated THP-1 cells to the heat-resistant, benzonase-resistant extracts coming from HeLa transfected cells and pelleted material. HeLa cells were either non-transfected, transfected with an empty vector or transfected with a Gag/Pol expressing vector and a VSV-G expressing vector (n=3). (B) Stimulation of PMA treated THP-1 cells with ultracentrifuged filtered material produced from HeLa cells transfected as in (A) and soluble IP-10 production quantification (n=3). (C) 293FT cells transfected with a Luciferase reporter plasmid under control of the IFN-β promoter with or without a STING coding plasmid. The cells were either stimulated with titrated amounts of ultracentrifuged material from transfected HeLa cells, stimulated with synthetic 2'-3' cGAMP using lipofectamine or transfected with a plasmid coding for the constitutively active protein RIG-I N228. (n=3).

Figure 14A:
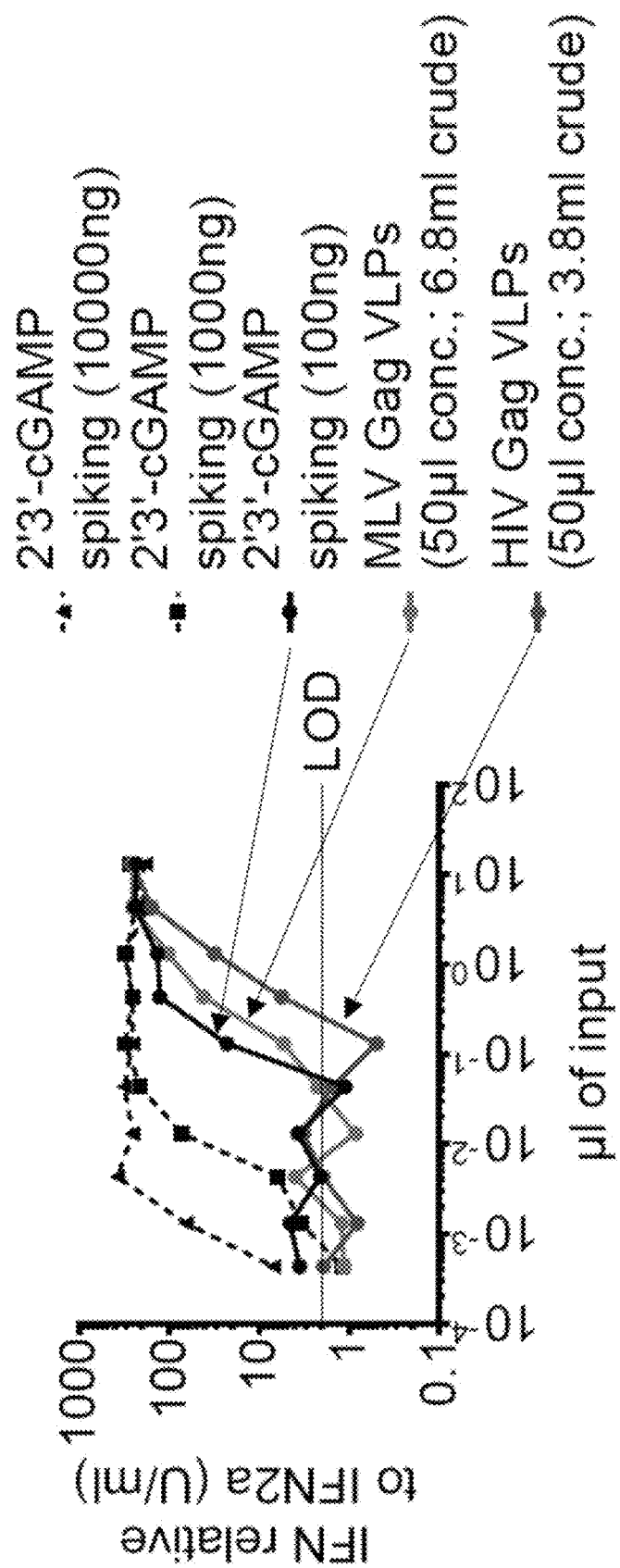
Figure 14B:
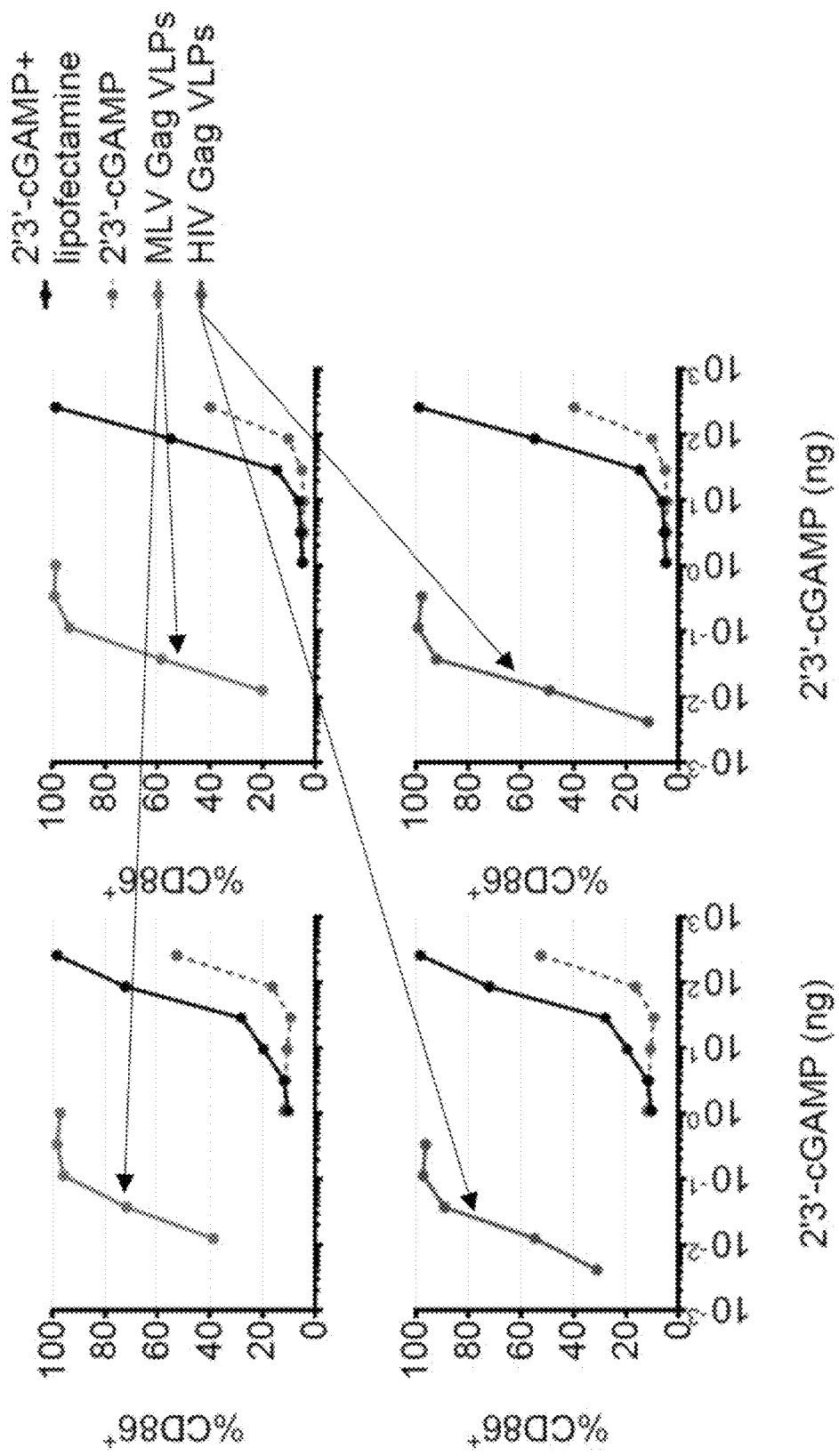

FIGS. 14A-14B. cGAMP content quantification and efficacy of delivery of VLPs. (A) Small molecules extraction from MLV Gag VLPs (expressing OVA as in-frame fusion to the C-terminus of Gag) and HIV Gag VLPs and cGAMP quantification by bioassay with internal spiking controls included to estimate cGAMP content in the viral preps. Each dot represents a 1:3 dilution. MLV Gag VLPs cGAMP content was estimated to be 3-fold less than 100 ng of cGAMP at top dose (final concentration in concentrated prep: 660 ng/ml); HIV Gag VLPs cGAMP content was estimated to be 9-fold less than 100 ng of cGAMP at top dose (final concentration in concentrated prep: 220 ng/ml). (B) Infection of monocytes from two independent donors with MLV Gag and HIV Gag viral preps. Estimated cGAMP content for viral preps based on bioassay in (A) and for cGAMP stimulation is represented on x axis and the correspondant activity on monocytes measured by the upregulation of the co-stimulatory molecule CD86 is shown on y axis. MLV Gag and HIV Gag VLPs are approximately 1,000 fold more efficient than 2'3'-cGAMP complexed with lipofectamine and approximately 10,000 fold more efficient than 2'3'-cGAMP in inducing dendritic cell maturation.

FIGS. 15A-15H. Adjuvanticity of cGAS-VLP containing a specific antigen (Figures A to E) or not (Figures F to H). (FIG. 15A) Mice were immunized s.c. with VLPs containing cGAMP and Ova protein at 3 different doses, successively diluted by 3. Control mice received the VLPs containing the cGAMP without the antigen, or OVA protein (20 µg) administered with synthetic cGAMP (10 µg) (InVivogen) or CpG (40 µg) (Trilink Technologies) as adjuvant. (FIG. 15B) Experimental schedule. Mice (6/group) were first immunized and 11 days later, immune responses were analyzed in the blood. On day 14, B16-OVA melanoma tumor cells were grafted by s.c. and 11 days later, immune responses were analyzed in the blood of mice. (FIG. 15C) CD8 T cell responses were analyzed after VLPs immunization by IFN-g producing cells measurement and tetramer detection. Results are expressed as individual mice with the mean±SEM. (FIG. 15D) Then CD8 responses were analyzed after the tumor engraftment by the measurement of IFN-g producing cells. (FIG. 15E) Individual curves for tumor growth in each group. (FIG. 15F) Experimental groups received cGAMP-VLPS at 3 different doses, successively diluted by 3. Control mice received PBS saline solution. (FIG. 15G) Experimental schedule. Mice (7 or 8/group) were first grafted by B16-OVA melanoma tumor and 12 days later, were injected i.t. with the cGAMP-VLPs. After 10 days, immune responses were analyzed in the blood. (FIG. 15H) CD8 T cell responses were analyzed by the quantification of IFN-g producing cells and tetramer detection. Results are expressed as individual mice with the mean±SEM.

DETAILED DESCRIPTION OF THE INVENTION

The present invention relates to a virus-like particle (VLP) comprising a lipoprotein envelope including a viral fusogenic glycoprotein, wherein said virus-like particle contains cyclic dinucleotides, in particular cGAMP, packaged into said virus-like particle.

It also relates to the use of an enveloped VLP comprising a lipoprotein envelope including a viral fusogenic glycoprotein for vectorizing or delivering cyclic dinucleotides, in particular cGAMP, to cells.

It further relates to a method for preparing an enveloped VLP containing cyclic dinucleotides, in particular cGAMP, and comprising a lipoprotein envelope including a viral fusogenic glycoprotein.

It finally relates to the use of a virus-like particle comprising an enveloped VLP comprising a lipoprotein envelope including a viral fusogenic glycoprotein and containing the VLP cyclic dinucleotides, in particular cGAMP, for inducing an immune response. It relates to its use as a vaccine or vaccine adjuvant. Accordingly, it relates to a pharmaceutical composition or a vaccine composition comprising an enveloped VLP containing cyclic dinucleotides, in particular cGAMP, and comprising a retroviral capsid protein. It relates to the use of an enveloped VLP containing cyclic dinucleotides, in particular cGAMP, and comprising a retroviral capsid protein as a drug, in particular for treating or preventing a viral infection or for treating cancer.

Definitions

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding an enzyme of the present invention. Control sequences may be native (i.e., from the same gene) or heterologous (i.e., from a different gene and/or a different species) to the polynucleotide encoding the enzyme. Preferably, control sequences are heterologous. Well-known control sequences currently used by the person skilled in the art will be preferred. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding the enzyme. The functional combination of control sequences and coding sequences can be referred as expression cassette.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding the enzyme of the invention and is operably linked to control sequences that provide for its expression. Then the expression vector comprises an expression cassette suitable for expressing the enzyme of the invention.

Recombinant: Recombinant refers to a nucleic acid construct, a vector and a protein produced by genetic engineering.

Heterologous: In the context of a host cell, a vector or a nucleic acid construct, it designates a coding sequence for a cyclic dinucleotide synthase introduced into the host cell, the vector or the nucleic acid construct by genetic engineering. In the context of a host cell, it can mean that the coding sequence for the cyclic dinucleotide synthase originates from a source different from the cell in which it is introduced (e.g., human vs mouse or mouse vs human). Alternatively, it can also mean that the coding sequence for cyclic dinucleotide synthase comes from the same species as the cell in which is introduced but it is considered heterologous due to its environment which is not natural, for example because it is under the control of a promoter which is not its natural promoter, or is introduced at a location which differs from its natural location.

Nucleic acid construct: The term "nucleic acid construct" means a nucleic acid molecule, either single- or double-stranded, which is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to a coding sequence, in such a way that the control sequence directs expression of the coding sequence.

Adjuvant: Substances which are added and/or co-formulated in an immunization to the active antigen in order to enhance or elicit or modulate the humoral and/or cell-mediated immune response against the active antigen. Preferably, the adjuvant is also able to enhance or elicit the innate immune response.

Antigen: A structure capable of causing a cellular or humoral immune response.

Treatment or Therapy: A process that is intended to produce a beneficial change in the condition of an individual, e.g., mammal, especially human. Human and veterinary treatments are both contemplated. A beneficial change can include one or more of: restoration of function, reduction of symptoms, limitation or retardation of a disease, disorder, or condition, or prevention, limitation or retardation of deterioration of a patient's condition, disease or disorder. In particular, as used herein, the term "treatment" (also "treat" or "treating") refers to any administration of an immunogenic composition that partially or completely alleviates, ameliorates, relieves, inhibits, delays onset of, reduces severity of and/or reduces incidence of one or more symptoms or features of a particular disease, disorder, and/or condition (e.g., viral infection) or the predisposition toward the disease. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In certain embodiments, the term "treating" refers to the vaccination of a patient.

VLP or Virus-like particle: These resemble viruses but are non-infectious. It does not contain any wild-type viral genetic material and more preferably any viral infectious genetic material. The expression of viral structural proteins such as envelope or capsid, results in the self-assembly of VLP. VLP can be a virosome (i.e., a lipoprotein envelope devoid of capsid) and a VLP comprising both a capsid and a lipoprotein envelope.

Fusion protein: Refers to a polypeptide including at least two segments, these segments not being included in a single peptide in nature.

Therapeutic active agent or active ingredient: Refers to a chemical substance, which exhibits a therapeutic activity when administered to a subject. These include, as non-limiting examples, inhibitors, ligands (e.g., receptor agonists or antagonists), co-factors, anti-inflammatory drugs (steroidal and non-steroidal), antiviral drugs, antifungal drugs, anti-parasitic drugs, anti-psychotic agents, analgesics, anti-thrombogenic agents, anti-platelet agents, anticoagulants, anti-diabetics, statins, toxins, antimicrobial agents, anti-histamines, metabolites, anti-metabolic agents, vasoactive agents, vasodilator agents, cardiovascular agents, chemotherapeutic agents, antioxidants, phospholipids, anti-proliferative agents and heparins.

Virus-Like Particles

The present invention relates to a virus-like particle (VLP) comprising a lipoprotein envelope including a viral fusogenic glycoprotein, wherein said virus-like particle contains cyclic dinucleotides packaged into said virus-like particle.

The viral fusogenic glycoprotein can be a glycoprotein or a combination of several glycoproteins from retroviridae (including lentivirus and retrovirus, e.g., alpharetrovirus, betaretrovirus, gammaretrovirus, deltaretrovirus, epsilonretrovirus), herpesviridae, poxviridae, hepadnaviridae, flaviviridae, togaviridae, coronaviridae, hepatitis D virus, orthomyxoviridae, paramyxoviridae, filoviridae, rhabdoviridae, bunyaviridae, or orthopoxiviridae (e.g., variola). In a preferred aspect, the viral fusogenic glycoprotein is from flaviviridae, retroviridae, orthomyxoviridae, paramyxoviridae, bunyaviridae, or hepadnaviridae. In a specific aspect, the viral fusogenic glycoprotein is from orthomyxovirus, rhabdoviridae, or retroviridae.

More specifically, the viral fusogenic glycoprotein can be from Hepatitis C virus (HCV), human immunodeficiency virus (HIV) including HIV-1 and HIV-2, simian immunodeficiency virus (SIV), feline immunodeficiency virus (FIV), Puma lentivirus, bovine immunodeficiency virus (BIV), Jembrana disease virus, Equine infectious anemia virus, Visna/maedi virus, Caprine arthritis encephalitis virus, feline leukemia virus (FeLV), murine leukemia virus (MLV), bovine leukemia virus (BLV), human T-lymphotropic virus (HTLV, e.g., HTLV-1, -2, -3 or -4), Rous sarcoma virus, Avian sarcoma leucosis virus, Newcastle disease virus (ND), Dengue virus, Hantaan virus, Influenza viruses A or B (e.g., H1N1, H2N2, H3N2, H5N1, H7N7, H1N2, H9N2, H7N2, H7N3, H10N7, H7N9 or any combination thereof), Hepatitis B virus (HBV), Vesicular Stomatitis Virus (VSV), Measles virus (MV), thogotovirus, herpes virus including HSV-1 and HSV-2, cytomegalovirus (CMV), Epstein-Barr virus (EBV), Kaposi's sarcoma-associated herpes virus (KSHV), Ebola virus, Marburg virus, Murray Valley encephalitis virus, Respiratory syncytial virus (RSV), Japanese encephalitis virus, Yellow fever virus, and West Nile virus. In a very specific aspect, the viral fusogenic glycoprotein is a glycoprotein from HIV (Human Immunodeficiency Virus) including HIV-1 and HIV-2, thogotovirus, Chikungunya virus, human severe acute respiratory syndrome coronavirus (SARS CoV), and VSV (Vesicular Stomatitis Virus).

In a particular embodiment, the viral fusogenic glycoprotein can be non-exhaustively chosen from the group consisting of HBsAg of HBV (e.g., M-, S- or L-HBsAg), E1 and/or E2 proteins of HCV (e.g., WO2014/128568), HA (hemaglutinin) and NA (neuraminidase) of Influenza, glycoprotein G of VSV, glycoprotein GP of Ebola or Marburg virus, glycoproteins Gp120 (or its CD4-binding domain) and Gp41 of lentiviruses, envelop protein (DENV E) and pre-membrane protein (prM DENV) of Dengue virus, two envelope glycoproteins of Hantaan virus, glycoprotein E2 of Chikungunya virus, glycoproteins HN and F of Newcastle virus, gp85 and gp37 of Rous sarcoma virus, and protein E and prM of Murray Valley encephalitis virus. The viral glycoprotein can be a derivative of the wildtype protein, for instance by truncation such as removing the cytoplasmic domain or by introduction of mutation(s).

Optionally, the viral glycoprotein can be fused or covalently bound to an antigen of interest or to a targeting moiety.

Alternatively, the lipoprotein envelope or VLPs may further comprise other proteins of interest such as an antigen, a targeting moiety or an immunostimulatory adhesion molecules and cytokines such as membrane-bound CD40 ligand (CD40L), membrane-anchored granulocyte-macrophage colony stimulating factor (GM-CSF) for enhancing VLPs immunogenicity. It can also further comprise flagellin, in particular membrane-anchored flagellin, especially in combination with influenza.

A non-exhaustive list of antigens which can be further included in VLPs, in addition to the viral glycoprotein and capsid proteins, includes any viral protein from Hepatitis C virus (HCV) such as core protein, p7 protein, NS3 and/or NS4A polypeptides, human immunodeficiency virus (HIV) including HIV-1 and HIV-2 such as gag, nef, Tat, Pol, Rev or reverse transcriptase, simian immunodeficiency virus (SIV), feline immunodeficiency virus (FIV), Puma lentivirus, bovine immunodeficiency virus (BIV), Jembrana disease virus, Equine infectious anemia virus, Visna/maedi virus, Caprine arthritis encephalitis virus, feline leukemia virus (FeLV), murine leukemia virus (MLV), bovine leukemia virus (BLV), human T-lymphotropic virus (HTLV, e.g., HTLV-1, -2, -3 or -4), Rous sarcoma virus (RSV), Avian sarcoma leucosis virus, Newcastle disease virus (ND), Dengue virus, Hantaan virus, Influenza viruses A or B such as matrix proteins M1 and M2, Hepatitis B virus (HBV), Vesicular Stomatitis Virus (VSV), thogotovirus, hepatitis A virus (HAV), Ebola virus, Marburg virus such as matrix VP40, Murray Valley encephalitis virus, Japanese encephalitis virus and West Nile virus. In a very specific aspect, the viral fusogenic glycoprotein is a glycoprotein from HIV (Human Immunodeficiency Virus) including HIV-1 and HIV-2, thogotovirus, Chikungunya virus such as C protein, human papilloma virus (HPV) such as L1 proteins or antigenic fragments thereof, human severe acute respiratory syndrome coronavirus (SARS CoV), and VSV (Vesicular Stomatitis Virus). More specifically, VLPs can also include antigens from tumor associated antigens such as Her2/neu, CEA (carcinoembryogenic antigen), HER2/neu, MAGE2 and MAGE3 (Melanoma-associated antigen), RAS, mesothelin or p53, from HIV such as Vpr, Vpx, Vpu, Vif and Env, from bacteria such as *C. albicans* SAP2 (secreted aspartyl proteinase 2), *Clostridium difficile*, from parasites such as *P. falciform* proteins such as CSP (circumsporozoite protein), AMA-1 (apical membrane antigen-1), TRAP/SSP2 (sporozoite surface protein 2), LSA (liver stage antigen), Pf Exp1 (Pf exported protein 1), SALSA (Pf antigen 2 sporozoite and liver stage antigen), STARP (sporozoite threonine and asparagins-rich protein) or any protein as disclosed in WO2011/138251.

The enveloped VLPs may include several, in particular two or more, different epitopes/antigens which are selected either (a) from different viral strains of the same virus and/or (b) from different serotypes of the same virus and/or (c) from different viral strains specific for different hosts. Different viral strains of the invention are, for example, different strains of influenza virus, for example influenza virus A strains H1N1, H5N1, H9N1, H1N2, H2N2, H3N2 or H9N2, or also influenza virus B or influenza virus C. Different serotypes are, for example, different serotypes of human papilloma virus (HPV), for example serotypes 6, 11, 16, 18, 31, 33, 35, 39, 45, 48, 52, 58 62, 66, 68, 70, 73 and 82, or also from the proto-oncogenic types HPV 5, 8, 14, 17, 20 and 47 or from human papilloma relevant types HPV 6, 11, 13, 26, 28, 32 and 60.

For instance, WO14068001 discloses VLPs having CMV surface proteins. Surface proteins could be chosen from the group consisting of gpUL75 (gH), gpUL115 (gL), gpUL55 (gB), gpUL74 (gO), gpUL100 (gM), gpUL73 (gN), gpUL128, gpUL130, and gpUL131A. VLPs may further comprise CMV tegument proteins such as pUL83 and pUL32. CMV proteins may be from different strains selected from the group of Towne, Toledo, AD169, Merlin, TB20 and VR1814 strains.

In another example, the VLPs comprise L1 proteins of HPV or antigenic fragments thereof. In particular, they include at least L1 proteins from HPV16 and HPV18, and optionally from HPV6 and HPV11.

In the context of Influenza vaccine, the VLPs comprise HA and NA surface proteins. They may further or alternatively include M1 and/or M2 proteins, in particular the external domain of M2.

The virus-like particle disclosed herein preferably further comprises a capsid. Preferably, the capsid is from retroviridae. Retroviridae includes lentivirus and retrovirus, e.g., alpharetrovirus, betaretrovirus, gammaretrovirus, deltaretrovirus, and epsilonretrovirus. For instance, the capsid is from human immunodeficiency virus (HIV) including HIV-1 and HIV-2, simian immunodeficiency virus (SIV), feline immunodeficiency virus (FIV), Puma lentivirus, bovine immunodeficiency virus (BIV), Caprine arthritis encephalitis virus, feline leukemia virus (FeLV), murine leukemia virus (MLV), bovine leukemia virus (BLV), human T-lymphotropic virus (HTLV, e.g., HTLV-1, -2, -3 or -4), Rous sarcoma virus (RSV), Avian sarcoma leucosis virus, Equine infectious anemia virus, Moloney Murine leukemia virus (MMLV). More preferably, the retroviral capsid is from HIV or MLV (Murine Leukemia Virus).

Cyclic dinucleotides packaged into said virus-like particle are ubiquitous small molecule second messengers able to directly bind the endoplasmic reticulum-resident receptor STING (stimulator of interferon genes) and to activate a signaling pathway that induces the expression of type I interferon and also nuclear factor-κB (NF κB) dependent inflammatory cytokines. It includes cyclic di-adenosine monophosphate (c-di-AMP), cyclic di-guanosine monophosphate (c-di-GMP), more specifically c[G(2',5')pG(3',5')p] and c[G(3',5')pG(3',5')p], and cyclic guanosine monophosphate-adenosine monophosphate (cGAMP), more specifically c[G(2',5')pA(3',5')p] and c[G(3',5')pA(3',5')p]. In a preferred embodiment, the VLP contains at least 0.015 ng/ml of cGAMP.

Method for Preparing a Virus-Like Particle Containing Cyclic Dinucleotides.

The inventors surprisingly observed that a VLP containing cyclic dinucleotides, especially cGAMP, can be prepared when the corresponding cyclic dinucleotide synthase such as cGAS, diguanylate cyclase or diadenylate cyclase is co-expressed in a cell with the components of VLPs. However, the inventors defined that the VLP needs to be an enveloped VLP. Therefore, the present invention relates to a method for preparing an enveloped virus-like particle containing cyclic dinucleotides, especially c-di-GMP, c-di-AMP or cGAMP, comprising the co-expression of cyclic dinucleotide synthase such as cGAS, diguanylate cyclase or diadenylate cyclase and of the proteins of the enveloped virus-like particle in a cell.

Cyclic dinucleotide synthase is also called dinucleotide cyclase and belongs to the nucleotidyl transferase superfamily. It includes the cyclic GMP-AMP synthase belonging to EC 2.7.7.86, the diadenylate cyclase belonging to EC 2.7.7.85 and the diguanylate cyclase belonging to EC 2.7.7.65.

cGAS is a cyclic GMP-AMP synthase. Several members of this family have been recently identified and characterized, in particular murine cGAS and human cGAS (Wu et al., 2012, *Science*, 339, 826-830; Sun et al., 2012, *Science*, 339, 786-791). Human cGAS is referenced in UniprotKB ID No. Q8N884. The reference sequences are disclosed in NCBI RefSeq as NP_612450.2 for the amino acid sequence and as NM_138441.2 for the mRNA sequence.

(SEQ ID NO: 1)
MQPWHGKAMQRASEAGATAPKASARNARGAPMDPTESPAAPEAALPKAGK

FGPARKSGSRQKKSAPDTQERPPVRATGARAKKAPQRAQDTQPSDATSAP

GAEGLEPPAAREPALSRAGSCRQRGARCSTKPRPPPGPWDVPSPGLPVSA

PILVRRDAAPGASKLRAVLEKLKLSRDDISTAAGMVKGVVDHLLLRLKCD

SAFRGVGLLNTGSYYEHVKISAPNEFDVMFKLEVPRIQLEEYSNTRAYYF

-continued

VKFKRNPKENPLSQFLEGEILSASKMLSKFRKIIKEEINDIKDTDVIMKR

KRGGSPAVTLLISEKISVDITLALESKSSWPASTQEGLRIQNWLSAKVRK

QLRLKPFYLVPKHAKEGNGFQEETWRLSFSHIEKEILNNHGKSKTCCENK

EEKCCRKDCLKLMKYLLEQLKERFKDKKHLDKFSSYHVKTAFFHVCTQNP

QDSQWDRKDLGLCFDNCVTYFLQCLRTEKLENYFIPEFNLFSSNLIDKRS

KEFLTKQIEYERNNEFPVFDEF.

Murine cGAS is referenced in UniprotKB ID No Q8C6L5. The reference sequences are disclosed in NCBI RefSeq as NP_775562.2 for the amino acid sequence and as NM_173386.4 for the mRNA sequence.

(SEQ ID NO: 2)
MEDPRRRTTAPRAKKPSAKRAPTQPSRTRAHAESCGPQRGARSRRAERDG

DTTEKPRAPGPRVHPARATELTKDAQPSAMDAAGATARPAVRVPQQQAIL

DPELPAVREPQPPADPEARKVVRGPSHRRGARSTGQPRAPRGSRKEPDKL

KKVLDKLRLKRKDISEAAETVNKVVERLLRRMQKRESEFKGVEQLNTGSY

YEHVKISAPNEFDVMFKLEVPRIELQEYYETGAFYLVKFKRIPRGNPLSH

FLEGEVLSATKMLSKFRKIIKEEVKEIKDIDVSVEKEKPGSPAVTLLIRN

PEEISVDIILALESKGSWPISTKEGLPIQGWLGTKVRTNLRREPFYLVPK

NAKDGNSFQGETWRLSFSHTEKYILNNHGIEKTCCESSGAKCCRKECLKL

MKYLLEQLKKEFQELDAFCSYHVKTAIFHMWTQDPQDSQWDPRNLSSCFD

KLLAFFLECLRTEKLDHYFIPKFNLFSQELIDRKSKEFLSKKIEYERNNG

FPIFDKL.

cGAS have also been well characterized in Bovine, pig and *Vibrio cholera* serotype O1 (respectively, see UniprotKB ID Nos E1BGN7, I3LM39 and Q9KVG7) and can be also found in *Drosophila* (e.g., *D. melanogaster*), zebrafish (*D. rerio*), *A. carolinensis, A. melanoleuca, A. mellifera, B. floridae, C. lupus familiaris, E. caballus, F. catus, G. gallus, G. gorilla gorilla, H magnipapillata, I. scapularis, M. brevicollis, M. domestica, M. gallopavo, M. mulatta, N. vectensis, N. vitrioennis, O. anatinus, O. aries, O. cuniculus, O. latipes, P. abelii, P. anubis, P. paniscus, P. troglodytes, R. norvegicus, S. harrisii, T. castaneum, T. guttata* and *X. tropicalis* or *laevis* (Wu et al., 2014, *Nucleic Acids Research*, 42, 8243-8257, the disclosure of which is incorporated by reference). In a preferred embodiment, nucleic acid sequence encoding either the human or murine cGAS is used.

The cyclic dinucleotide cGAMP can be cGAMP (2'-3'-cyclic GMP-AMP) or cGAMP (3'-3'-cyclic GMP-AMP). In a first embodiment, cGAMP is cGAMP (2'-3'-cyclic GMP-AMP) [also called Cyclic [G(2',5')pA(3',5')p]; CAS number: 1441190-66-4). In a second embodiment, cGAMP can be cGAMP (3'-3'-cyclic GMP-AMP) [also called cyclic A-P(3'-5')G-P(3'-5'); CAS number: 849214-04-6].

In a preferred embodiment, human or murine cGAS is used for preparing cGAMP (2'-3'-cyclic GMP-AMP). In another preferred embodiment, cGAS from *Vibrio cholera* serotype O1 is used for preparing cGAMP (3'-3'-cyclic GMP-AMP).

The diadenylate cyclase is a cyclic di-AMP synthase. It may also be called DisA (DNA integrity scanning protein) or CdaA. Numerous members of this family have been identified (see Corrigan and Grundling, 2013, *Nature*, 11, 513-524, the disclosure of which is incorporated by reference). For instance, the diadenylate cyclase can be chosen from the enzymes of *Bacillus subtilis* (UniProt No. P37573), *Listeria monocytogenes* (UniProt No. Q8Y5E4), *Bacillus thuringiensis* (UniProt No. D5TK88), and *Thermotoga maritima* (UniProt No. Q9WY43).

The diguanylate cyclase is a cyclic di-GMP synthase. Several members of this family have been identified (see, Massie et al., 2012, *PNAS*, 109, 12746-12751; the disclosure of which is incorporated by reference). For instance, the diguanylate cyclase can be chosen from the enzymes of *Thermotoga maritima* (UniProt No. Q9X2A8), *Desulfotalea psychrophila* (UniProt No. Q6ARU5), *Anaplasma phagocytophilum* (UniProt No. Q2GKF8), *E. coli* (UniProt No. P0AA89), *Vibrio chloerae* (UniProt No. Q9KPJ7), *Caulobacter vibrioides* (UniProt No. Q9A515), *Pseudomonas fluorescens* (UniProt No. Q3K751 or Q3KFC4), *Marinobacter hydrocarbonoclasticus* (UniProt No. A1U3W3), and *Pseudomonas aeruginosa* (UniProt No. Q914M8).

By Cyclic dinucleotide synthase is also encompassed variants thereof keeping the activity for cyclic dinucleotide synthesis. In particular, it includes Cyclic dinucleotide synthase having a tag moiety, in particular useful for purification or immobilization of the enzyme. Such a tag is well-known by the person skilled in the art, for instance a His tag ($His_6$), a FLAG tag, an HA tag (epitope derived from the Influenza protein haemagglutinin), a maltose-binding protein (MPB), a MYC tag (epitope derived from the human proto-oncoprotein MYC) or a GST tag (small glutathione-S-transferase). It also includes variants having mutations, in particular mutations improving the activity for cyclic dinucleotide synthesis. Such variants may vary by 1, 2, 3, 4, 5, 6, 7, 8, 9 or 10 amino acids substitutions, deletions and/or additions. Preferably, the variants have at least 75, 80, 85, 90, 95 or 99% identity with the wildtype Cyclic dinucleotide synthase. The variant may be obtained by various techniques well known in the art. In particular, examples of techniques for altering the DNA sequence encoding the wild-type protein include, but are not limited to, site-directed mutagenesis, random mutagenesis and synthetic oligonucleotide construction.

As used herein, the term "sequence identity" or "identity" refers to the number (%) of matches (identical amino acid residues) in positions from an alignment of two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithm (e.g., Needleman-Wunsch algorithm; Needleman and Wunsch, 1970, *J. Mol. Biol* 48:443) which aligns the sequences optimally over the entire length, while sequences of substantially different lengths are preferably aligned using a local alignment algorithm (e.g., Smith-Waterman algorithm (Smith and Waterman, 1981, *Adv. Appl. Math.* 2:482) or Altschul algorithm (Altschul et al., 1997, *Nucleic Acids Res.* 25:3389-3402; Altschul et al., 2005, *FEBS J.* 272:5101-5109)). Alignment for purposes of determining percent amino acid sequence identity can be achieved in various ways that are within the skill in the art, for instance, using publicly available computer software available on internet web sites such as http://blast.ncbi.nlm.nih.gov/ or Worldwide Website ebi.ac.uk/Tools/emboss/). Those skilled in the art can determine appropriate parameters for measuring alignment, including any algorithms needed to achieve maximal alignment over the full length of the sequences being compared. For purposes herein, % amino acid sequence identity values refers to values generated using the pair wise sequence alignment program EMBOSS Needle, which creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

Cyclic dinucleotide synthase coding sequence is in a nucleic acid construct including all the necessary elements for its expression in cells, in particular the elements required for transcription and translation in the host cell. Preferably, cyclic dinucleotide synthase coding sequence is overexpressed in the cell. Therefore, the coding sequence for the cyclic dinucleotide synthase coding sequence is under control of a strong promoter such as the promoters PGK, CMV, Ubiquitin, MHC-II, beta2-migroglobulin, CAG, SV40, SFFV LTR, EF1a, and retroviral LTR.

Similarly, the sequences coding of the proteins of the enveloped virus-like particle, especially the envelope's glycoprotein and the capsid protein, are comprised in a nucleic acid construct including all the necessary elements for its expression in cells, in particular the elements required for transcription and translation in the host cell.

Coding sequence for the cyclic dinucleotide synthase in the cell can be episomal, e.g., in an expression vector, or can be incorporated in the cell's chromosome. Optionally, coding sequence for the cyclic dinucleotide synthase can be in an expression vector distinct from vector(s) comprising the coding sequences for the proteins of the enveloped virus-like particle. Alternatively, the coding sequence for the cyclic dinucleotide synthase and the coding sequences for the proteins of the enveloped virus-like particle are comprised in the same expression vector.

Accordingly, when the coding sequences for the cyclic dinucleotide synthase and for the proteins of the enveloped virus-like particle are not comprised in the same expression vector or construct, the present invention relates to a combination or kit of nucleic acid constructs or expression vectors comprising at least one nucleic acid construct or expression vector comprising the sequence encoding the cyclic dinucleotide synthase and one nucleic acid construct or expression vector comprising the sequence encoding at least one protein of the enveloped virus-like particle, in particular the envelope glycoprotein and/or the capsid.

The present invention relates to a nucleic construct or an expression vector comprising a sequence encoding a cyclic dinucleotide synthase and a sequence encoding a viral fusogenic glycoprotein and/or a sequence encoding a capsid, especially a capsid from retroviridae. Preferably, the nucleic construct or expression vector comprises a sequence encoding a capsid, especially a capsid from retroviridae, and a sequence encoding a viral fusogenic glycoprotein. The fusogenic glycoprotein, cyclic dinucleotide synthase and capsid can be any one of those described above. In a preferred embodiment, the nucleic construct or expression vector comprises a sequence encoding cGAS, in particular under the control of a strong promoter. Optionally, the nucleic construct or expression vector may further comprise a sequence encoding an antigen or a protein of interest or nucleic acid of interest (siRNA, miRNA, antisense, and the like).

Expression vectors that can be used in the present invention include non-exhaustively eukaryotic expression vectors, in particular mammalian expression vectors, virus based expression vectors, baculovirus expression vectors, plant expression vectors, and plasmid expression vectors. Suitable expression vectors can be derived from viruses such as baculoviruses, papova viruses such as SV40, vaccinia viruses, adenoviruses, fowlpox viruses, pseudorabies viruses and retroviruses, especially lentiviruses, or combinations thereof.

Any eukaryotic cell can be used in the method. For instance, cells used for the production can be mammalian cells, for example COS-1 cells, CHO (Chinese hamster ovary) cells (U.S. Pat. No. 4,889,803; U.S. Pat. No. 5,047,335), HEK (human embryonic kidney) cell lines such as 293 and 293T cell lines and HL-116 cell lines, Vero cell lines, BHK (baby hamster kidney) cell lines; plant cells (e.g., N. bethamiana); insect cells such as *Spodoptera frugiperda* (Sf)-derived cells, such as Sf-9 cells, SF21, Hi-5, Express Sf+, and S2 Schneider cells, in particular with a baculovirus-insect cell expression system; or avian cells.

The present invention relates to a recombinant host cell comprising a nucleic construct or an expression vector as described above.

The present invention relates to a method for producing a virus-like particle comprising cyclic dinucleotides packaged into said virus-like particle as described above, wherein the method comprises:
  co-expression of a cyclic dinucleotide synthase and a viral fusogenic glycoprotein in aeukaryotic host cell in conditions allowing the synthesis and activity of cyclic dinucleotides and the viral fusogenic glycoprotein in said cell; and
  recovery of the virus-like particles produced by said cell.

Preferably, the host cell further co-expresses a capsid from retroviridae. The fusogenic glycoprotein, cyclic dinucleotide synthase and capsid can be any one of the proteins as described above.

In a particular embodiment, the method may further comprise a preliminary step of introducing into the host cell a nucleic construct or expression vector encoding the viral fusogenic glycoprotein. It may also comprise the introduction into the host cell of a nucleic construct or expression vector encoding the cyclic dinucleotide synthase and/or a nucleic construct or expression vector encoding the capsid protein. In a preferred embodiment, the method comprises a step of introducing into the host cell double-stranded DNA by transfection, in particular a nucleic construct or expression vector by transfection.

In a preferred embodiment, the cyclic dinucleotide synthase is cGAS, in particular a human or murine cGAS, more preferably a murine cGAS. In another embodiment, the cyclic dinucleotide synthase is cGAS from *Vibrio cholera* serotype O1.

Methods for producing VLPs are well-known by the person skilled in the art (Zeltins, 2013, *Mol Biotechnol*, 53, 92-107, the disclosure of which being incorporated herein by reference): in particular, in Baculovirus expression system (Liu et al., 2013, *Protein Exper Purif*, 90, 104-116; Sokolenko et al., 2012, *Biotechnol Adv*, 30, 766-81; and Vicente et al., 2011, *J Invertebr Pathol*, 107 suppl., S42-48, the disclosure of which is incorporated herein by reference); in plants (Scotti and Rybicki, 2013, *Expert Rev Vaccines*, 12, 211-24; and Chen and Lai, 2013, *Hum Vaccin Immunother.*, 9, 26-49, the disclosure of which is incorporated herein by reference) and in avian expression systems. Indeed, several VLP-based vaccine are already marketed. For review, please refer for instance to Kushnir et al. (2012, *Vaccine*, 31, 58-83)

and Grgacic and Anderson (2006, *Methods*, 40, 60-65), the disclosure of which is incorporated herein by reference.

Produced VLPs may be recovered and/or purified according to any known techniques such as centrifugation, chromatography, and the like.

The present invention relates to the virus-like particle as described above as a drug or vaccine adjuvant. It relates to the use of the virus-like particle as described above for the manufacture of a drug or a vaccine, especially against an infectious disease or a cancer. Therefore, the present invention relates to a pharmaceutical, vaccine or veterinary composition comprising a virus-like particle as disclosed herein and a pharmaceutically acceptable carrier or excipient. The composition may further comprise an adjuvant. The composition may also comprise or be administered in combination with one or more additional therapeutically active substances.

The present invention relates to the expression vector or combination thereof as disclosed herein as a drug or vaccine adjuvant. Indeed, the expression vector can be administered to a subject and, when expressed in the recipient cells, the cells produce in vivo the virus-like particles as described above. Accordingly, the present invention relates to a pharmaceutical, vaccine or veterinary composition comprising an expression vector or combination thereof and a pharmaceutically acceptable carrier or excipient. It relates to the use of an expression vector or combination thereof as described above for the manufacture of a drug or a vaccine, especially against an infectious disease or a cancer. The expression vector or combination thereof comprises the coding sequence for proteins necessary for producing VLPs as disclosed herein.

Similarly, host cells as described above can also be used as a vaccine adjuvant or vaccine. Indeed, when such host cells are administered to the subject, they produce in vivo the virus-like particles as described above. In this context, the host cells can be cells from the receiving subject which have been genetically engineered before administration or are host cells compatible with the subject. Accordingly, the present invention relates to a pharmaceutical, vaccine or veterinary composition comprising host cells and a pharmaceutically acceptable carrier or excipient. The present invention relates to the use of a host cell as described above for the manufacture of a drug or a vaccine, especially against an infectious disease or a cancer. Host cells are able of producing VLPs as disclosed herein.

Pharmaceutical compositions of the present invention may additionally comprise a pharmaceutically acceptable excipient, which, as used herein, may be or comprise solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention. Pharmaceutically acceptable excipients can be preservative, inert diluent, dispersing agent, surface active agent and/or emulsifier, buffering agent and the like. Suitable excipients include, for example, water, saline, dextrose, sucrose, trehalose, glycerol, ethanol, or similar, and combinations thereof. In addition, if desired, the vaccine may contain auxiliary substances such as wetting or emulsifying agents, pH buffering agents, or adjuvants which enhance the effectiveness of the vaccines. In some embodiments, pharmaceutical compositions comprise one or more preservatives. In some embodiments, pharmaceutical compositions comprise no preservative.

The pharmaceutical compositions as disclosed herein may comprise an adjuvant. Any adjuvant may be used in accordance with the present invention. A large number of adjuvants are known; a useful compendium of many such compounds is prepared by the National Institutes of Health and can be found (see Worldwide Website: niaid.nih.gov/daids/vaccine/pdf/compendium.pdf). See also Allison (1998, *Dev. Biol. Stand.*, 92:3-11; incorporated herein by reference), Unkeless et al. (1998, *Annu. Rev. Immunol.*, 6:251-281; incorporated herein by reference), and Phillips et al. (1992, *Vaccine*, 10: 151-158; incorporated herein by reference). Hundreds of different adjuvants are known in the art and may be employed in the practice of the present invention. Exemplary adjuvants that can be utilized in accordance with the invention include, but are not limited to, cytokines, gel-type adjuvants (e.g., aluminum hydroxide, aluminum phosphate, calcium phosphate, etc.); microbial adjuvants (e.g., immunomodulatory DNA sequences that include CpG motifs; endotoxins such as monophosphoryl lipid A; exotoxins such as cholera toxin, *E. coli* heat labile toxin, and pertussis toxin; muramyl dipeptide, etc.); oil-emulsion and emulsifier-based adjuvants (e.g., Freund's Adjuvant, MF59 [Novartis], SAF, etc.); particulate adjuvants (e.g., liposomes, biodegradable microspheres, saponins, etc.); synthetic adjuvants (e.g., nonionic block copolymers, muramyl peptide analogues, polyphosphazene, synthetic polynucleotides, etc.); and/or combinations thereof. Other exemplary adjuvants include some polymers (e.g., polyphosphazenes; described in U.S. Pat. No. 5,500,161, which is incorporated herein by reference), Q57, QS21, squalene, tetrachlorodecaoxide, etc. Pharmaceutically acceptable excipients have been previously described in further detail in the above section entitled "Pharmaceutical Compositions."

The pharmaceutical compositions may optionally comprise and/or be administered in combination with one or more additional therapeutically active substances, in particular an antigen such as disclosed above.

The pharmaceutical compositions as disclosed herein are useful for inducing or enhancing an immune response. The present invention relates to a method for inducing or enhancing an immune response in a subject in need thereof, comprising administering a therapeutically efficient amount of a pharmaceutical composition as disclosed herein.

An immune response may refer to cellular immunity or humoral immunity or may involve both. An immune response may also be limited to a part of the immune system. For example, in certain embodiments, an immunogenic composition may induce an increased IFNγ response. In certain embodiments, an immunogenic composition may induce a mucosal IgA response (e.g., as measured in nasal and/or rectal washes). In certain embodiments, an immunogenic composition may induce a systemic IgG response (e.g., as measured in serum). In certain embodiments, an immunogenic composition may induce virus-neutralizing antibodies or a neutralizing antibody response. In certain embodiments, an immunogenic composition may induce a CTL response.

Accordingly, the pharmaceutical or veterinary compositions are useful as vaccines or as vaccine adjuvants. They are also useful for treating an infectious disease or a cancer. The present invention relates to a method for treating an infectious disease or a cancer in a subject in need thereof, comprising administering a therapeutically efficient amount of a pharmaceutical composition as disclosed herein. The infectious disease can be due to a virus, a bacterium or a parasite.

The virus can be selected from the non-exhaustive list consisting of retroviridae (including lentivirus and retrovirus, e.g., alpharetrovirus, betaretrovirus, gammaretrovirus, deltaretrovirus, and epsilonretrovirus), herpesviridae, poxviridae, hepadnaviridae, flaviviridae, togaviridae, coronaviridae, hepatitis D virus, orthomyxoviridae, paramyxoviridae, filoviridae, rhabdoviridae, bunyaviridae, or orthopoxiviridae (e.g., variola). It can also be selected from the non-exhaustive list consisting of Hepatitis C virus (HCV), human immunodeficiency virus (HIV), including HIV-1 and HIV-2, simian immunodeficiency virus (SIV), feline immunodeficiency virus (FIV), Puma lentivirus, bovine immunodeficiency virus (BIV), Jembrana disease virus, Equine infectious anemia virus, Visna/maedi virus, Caprine arthritis encephalitis virus, feline leukemia virus (FeLV), murine leukemia virus (MLV), bovine leukemia virus (BLV), human T-lymphotropic virus (HTLV, e.g., HTLV-1, -2, -3 or -4), Rous sarcoma virus, Avian sarcoma leucosis virus, Newcastle disease virus (ND), Dengue virus, Hantaan virus, Influenza viruses A or B (e.g., H1N1, H2N2, H3N2, H5N1, H7N7, H1N2, H9N2, H7N2, H7N3, H10N7, H7N9 or any combination thereof), Hepatitis B virus (HBV), Vesicular Stomatitis Virus (VSV), Measles virus (MV), thogotovirus, herpes virus including HSV-1 and HSV-2, cytomegalovirus (CMV), Epstein-Barr virus (EBV), Kaposi's sarcoma-associated herpesvirus (KSHV), Ebola virus, Marburg virus, Murray Valley encephalitis virus, Respiratory syncytial virus (RSV), Japanese encephalitis virus, Yellow fever virus, hepatitis A virus (HAV), human papilloma virus (HPV) and West Nile virus. In a preferred aspect, the virus can be from in the non-exhaustive list comprising HSV, HIV, Influenza virus, especially H5N1, CMV, Dengue virus, HBV, Ebola virus, HCV, RSV (Respiratory syncytial virus), West Nile virus, variola virus, and rotavirus.

The bacteria can be selected from the non-exhaustive list comprising *Clostridium difficile, E. coli, Corynebacterium diphtheriae, Clostridium tetani, Bordetella pertussis, Bacillus anthracis, Boriella* bacteria involved in Lyme disease, *Yersinia, Staphylococcus pneumonia,* and *Mycobacterium tuberculosis.*

The parasite can be *Plasmodium falciparum.*

The cancer may be selected from the non-exhaustive list comprising ovarian cancer, cervical cancer, breast cancer, prostate cancer, malignant melanoma, kidney cancer, bladder cancer, colorectal or colon cancer, lymphoma, pancreatic cancer, lung cancer, glioblastoma, glioma, thyroid cancer, head and neck cancer, liver cancer, myeloma, acute myeloid leukemia, chronic lymphocytic leukemia, non-Hodgkin's lymphoma, neuroblastoma, gastric cancer, and sarcoma.

As used herein, the term "vaccination" refers to the administration of a composition intended to generate an immune response, for example to a disease-causing agent (e.g., virus). For the purposes of the present invention, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition.

As used herein, the term "therapeutically effective amount" refers to an amount sufficient to confer a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular immunogenic composition, a therapeutically effective amount (and/or an appropriate unit dose within an effective dosing regimen) may vary, for example, depending on the route of administration or the combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific immunogenic composition employed; the duration of the treatment; and like factors as is well known in the medical arts.

As used herein, the term "amelioration" or "improvement" is meant the prevention, reduction or palliation of a state, or improvement of the state of a subject. Amelioration includes, but does not require, complete recovery or complete prevention of a disease, disorder or condition. The term "prevention" refers to a delay of onset of a disease, disorder or condition. Prevention may be considered complete when onset of a disease, disorder or condition has been delayed for a predefined period of time.

As used herein, the terms "dosage form" and "unit dosage form" refer to a physically discrete unit of a therapeutic agent for the patient to be treated. Each unit contains a predetermined quantity of active material calculated to produce the desired therapeutic effect. It will be understood, however, that the total dosage of the composition will be decided by the attending physician within the scope of sound medical judgment.

"Dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses.

As used herein, the terms "subject," "individual" or "patient" refer to a human or a non-human mammalian subject. The individual (also referred to as "patient" or "subject") being treated is an individual (fetus, infant, child, adolescent, or adult) suffering from a disease, for example, viral infection. In some embodiments, the subject is at risk for viral infection. In some embodiments, the subject is an immunosuppressed subject. For example, in some embodiments, the immunosuppressed subject is selected from the group consisting of an HIV-infected subject, an AIDS patient, a transplant recipient, a pediatric subject, and a pregnant subject. In some embodiments, the subject is a human. In some other embodiments, the subject is an animal, especially a pet (e.g., cat and dog), a farm animal (e.g., cattle, pig, sheep, rabbit, swine, fish, poultry), horses.

The pharmaceutical, veterinary or vaccine composition can be administered or suitable for administration by any convenient route of administration. For instance the contemplated routes are subcutaneous, intramuscular, mucosal (e.g., sublingual, intranasal, intra-rectal, intra-vaginal, or intrabronchial), intravenous or intratumoral routes.

For example, pharmaceutical compositions provided herein may be provided in a sterile injectable form (e.g., a form that is suitable for subcutaneous injection or intravenous infusion). For example, in some embodiments, pharmaceutical compositions are provided in a liquid dosage form that is suitable for injection. In some embodiments, pharmaceutical compositions are provided as powders (e.g., lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

Pharmaceutical compositions can be provided in a form that can be refrigerated and/or frozen. Alternatively, they can be provided in a form that cannot be refrigerated and/or frozen. Optionally, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer).

Formulations of the pharmaceutical compositions described herein may be prepared by any method known or hereafter developed in the art of pharmacology. Such preparatory methods include the step of bringing active ingredient into association with one or more excipients and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses.

Relative amounts of active ingredient, pharmaceutically acceptable excipient, and/or any additional ingredients in a pharmaceutical composition in accordance with the invention may vary, depending upon the identity, size, and/or condition of the subject treated and/or depending upon the route by which the composition is to be administered. By way of example, the composition may comprise between 0.1% and 100% (w/w) active ingredient.

Compositions described herein will generally be administered in such amounts and for such a time as is necessary or sufficient to induce an immune response. Dosing regimens may consist of a single dose or a plurality of doses over a period of time. The exact amount of an immunogenic composition (e.g., VLPs) to be administered may vary from subject to subject and may depend on several factors. Thus, it will be appreciated that, in general, the precise dose used will be as determined by the prescribing physician and will depend not only on the weight of the subject and the route of administration, but also on the age of the subject and the severity of the symptoms and/or the risk of infection. In a first aspect, a particular amount of the pharmaceutical composition is administered as a single dose. Alternatively, a particular amount of the pharmaceutical composition is administered as more than one dose (e.g., 1-3 doses that are separated by 1-12 months). Instead, a particular amount of the pharmaceutical composition is administered as a single dose on several occasions (e.g., 1-3 doses that are separated by 1-12 months). The pharmaceutical composition may be administered in an initial dose and in at least one booster dose.

The methods disclosed herein may be used for veterinary applications, e.g., canine and feline applications. If desired, the methods herein may also be used with farm animals, such as ovine, avian, bovine, porcine and equine breeds.

EXAMPLES

Example 1

The inventors showed that cGAMP can be incorporated into lentiviral particles when these are produced in cGAS-expressing cells. cGAMP is transferred to infected cells and triggers STING-dependent type I interferon (IFN) induction.

This effect was independent of reverse transcription and integration and may accelerate antiviral responses and broaden the spectrum of cells in which IFN is induced.

Results

Among the viruses that trigger cGAS-dependent IFN responses in infected cells are retroviruses, including human immunodeficiency virus (HIV). Responses to HIV are thought to involve detection by cGAS of viral cDNA made upon reverse transcription, leading to IFN gene transcription in the same cell where cDNA detection occurred. However, it is conceivable that IFN induction upon retrovirus infection could also occur independently of reverse transcription or cGAS if the infecting virus were to carry within it the cGAMP second messenger. The inventors hypothesized that cGAMP can be packaged into HIV-1 particles and elicit an IFN response in newly infected cells independently of cGAS expression by the latter, allowing for potentiation of innate antiviral immunity.

Figure 1B:
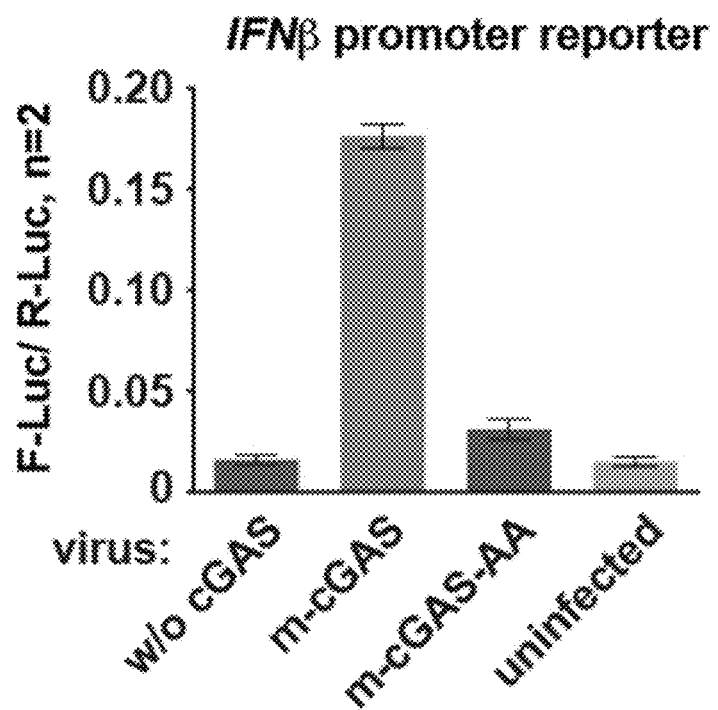
Figure 1C:
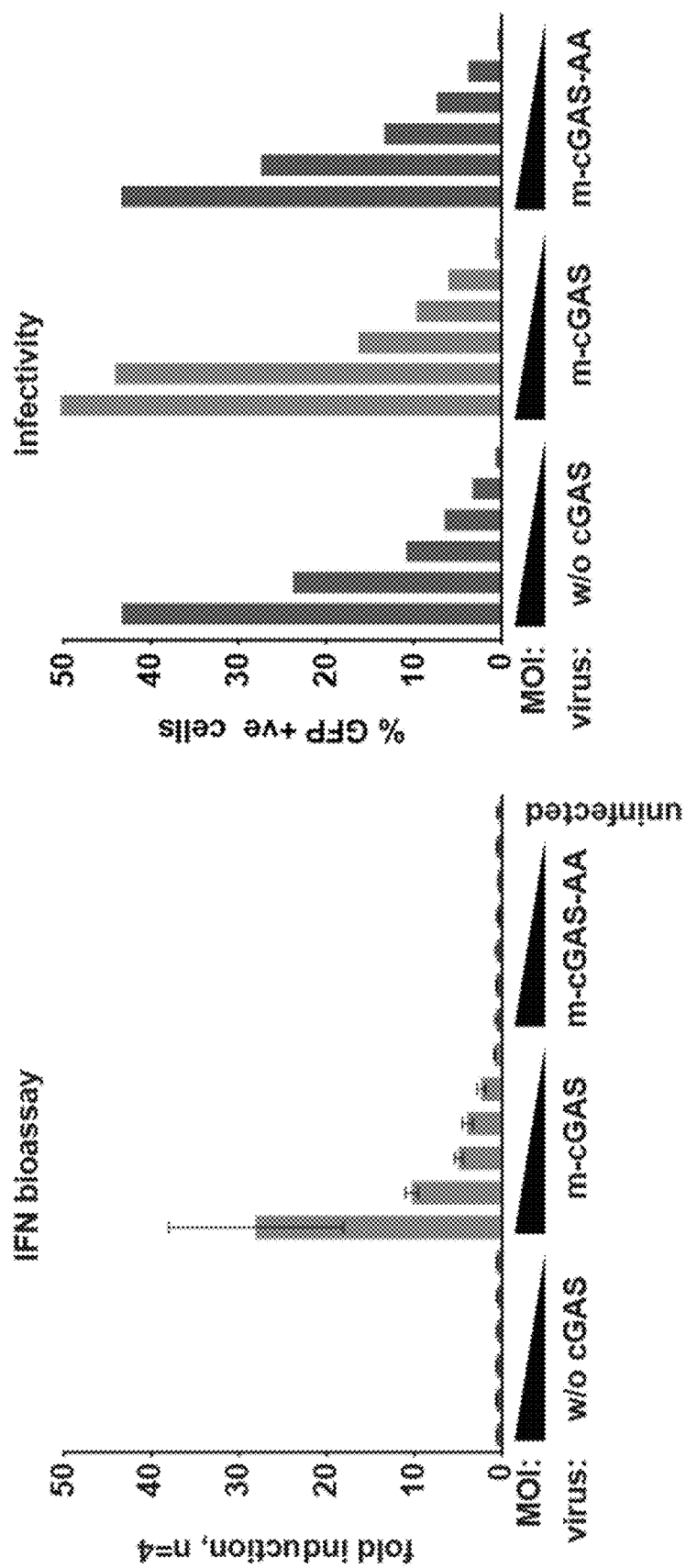
Figure 1D:
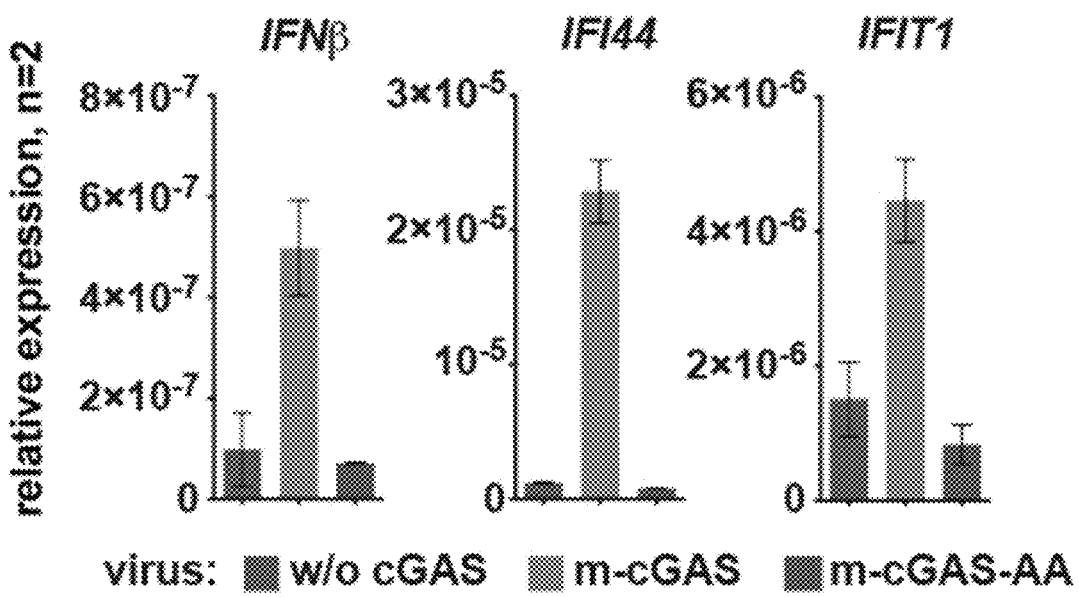
Figure 1E:
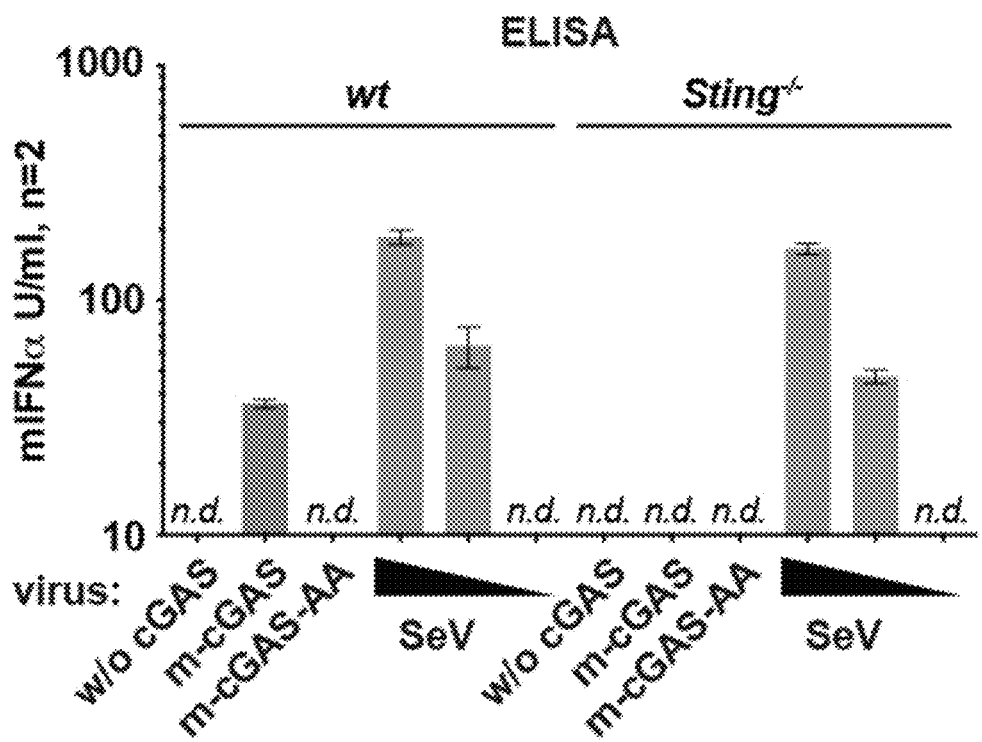
Figure 1F:
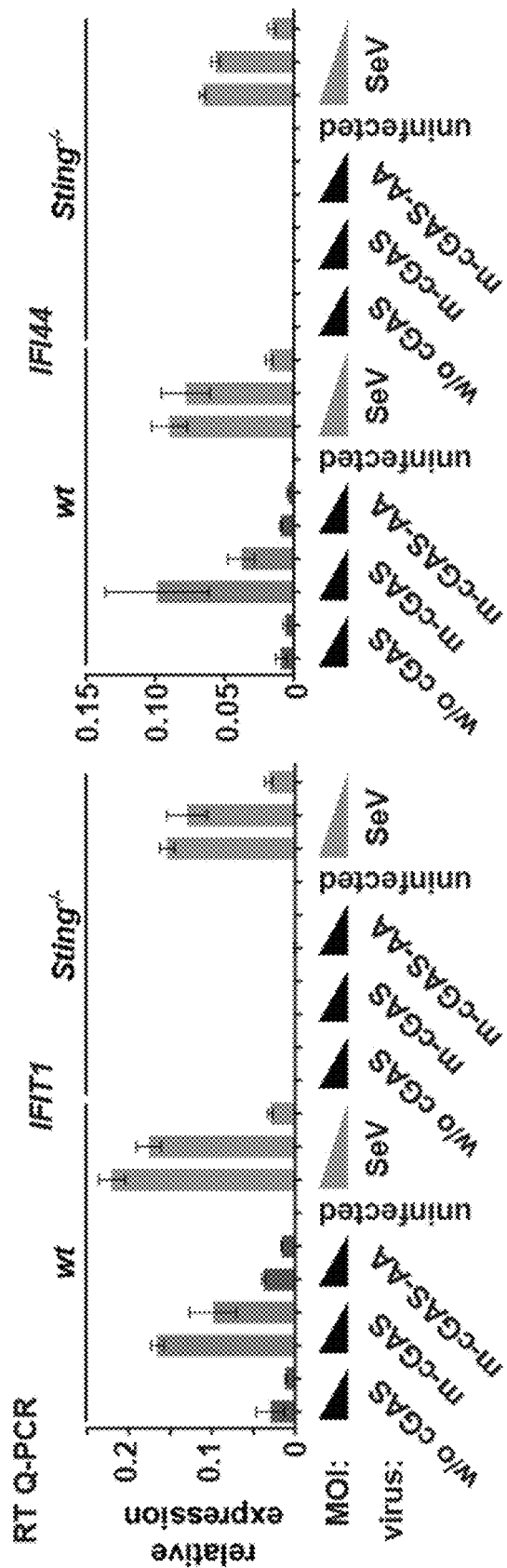

To test this idea, the inventors produced HIV-1-based lentivectors in 293T cells, a human cell line that does not express cGAS. Virus particles were pseudotyped with vesicular stomatitis virus glycoprotein (VSV-G) and the viral genome contained enhanced green fluorescent protein (EGFP) in the env open reading frame. These viruses, henceforth referred to as HIV-1-GFP, are replication incompetent due to the lack of functional env. In addition to the two plasmids required for virus production (pNL4-3-deltaE-EGFP and pVSV-G), some 293T cells were co-transfected with expression constructs for either wild-type m-cGAS or catalytically inactive m-cGAS-G198A/S199A (m-cGAS-AA) (Sun et al., 2013, *Science*, 339, 786-791). Titrated virus stocks were then used to infect fresh HEK293 cells (FIG. 1A), which express endogenous STING (FIG. 2A) and induce IFN in response to cGAMP (FIG. 2B). HIV-1-GFP collected from cGAS expressing cells triggered induction of an IFNβ promoter reporter, whereas viruses produced in the absence of exogenous cGAS or in the presence of mutant cGAS did not (FIG. 1B). Next, the inventors analyzed IFN secretion by transferring supernatants from infected cells to a reporter cell line (HEK293-ISRE-luc), in which firefly luciferase expression is driven by interferon stimulated response elements (FIG. 2C). Virus stocks produced in cGAS expressing cells triggered IFN secretion, while control viruses did not (FIG. 1C). The infectivity of these virus stocks was comparable (FIG. 1C) and wild-type and mutant cGAS were expressed at similar levels in virus producer cells (FIG. 2D). Moreover, infected cells induced IFNβ, IFI44 and IFIT1 mRNAs specifically when cGAS was present in virus producer cells, further demonstrating the induction of IFN and interferon-stimulated genes (ISGs) (FIG. 1D). The inventors next infected primary mouse bone marrow derived macrophages (BMDMs). The induction of IFN and ISGs was increased in BMDMs infected with HIV-1-GFP produced in cGAS-reconstituted 293T cells (FIGS. 1E, F). STING-deficient BMDMs did not induce IFN and ISGs in response to the same virus preparations, although RIG-I-dependent IFN production triggered by Sendai virus infection was normal (FIGS. 1E, F).

Figures 3A, 3B:
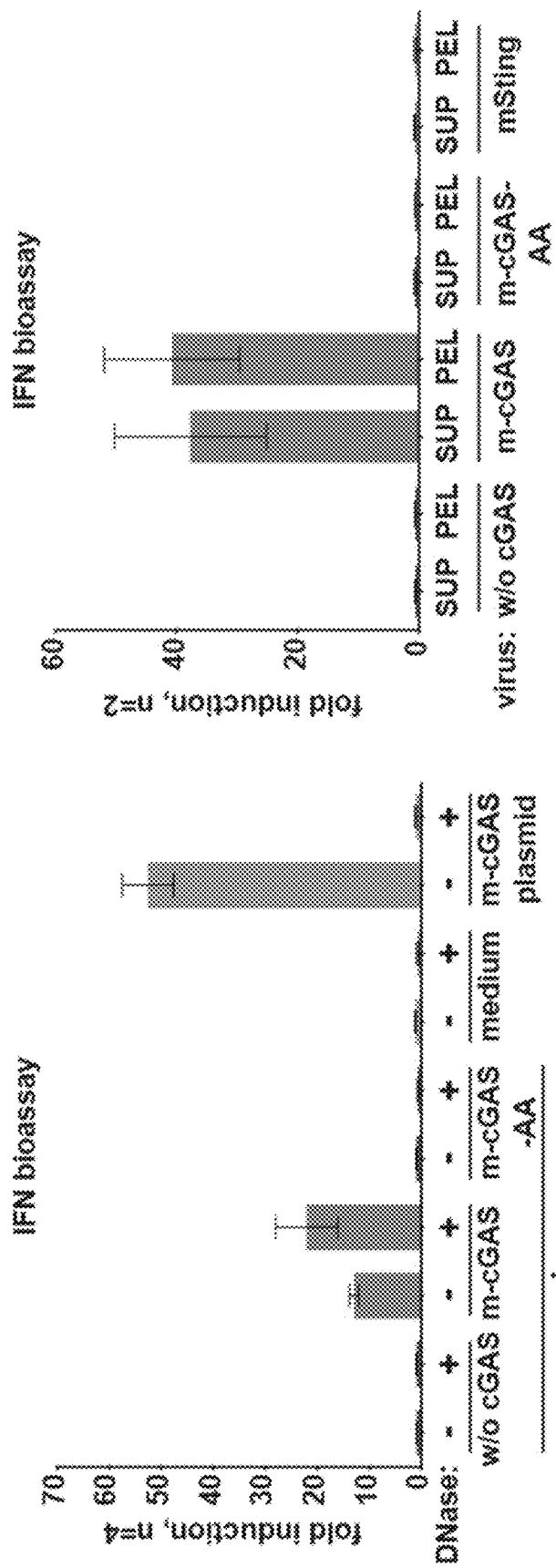
Figure 3C:
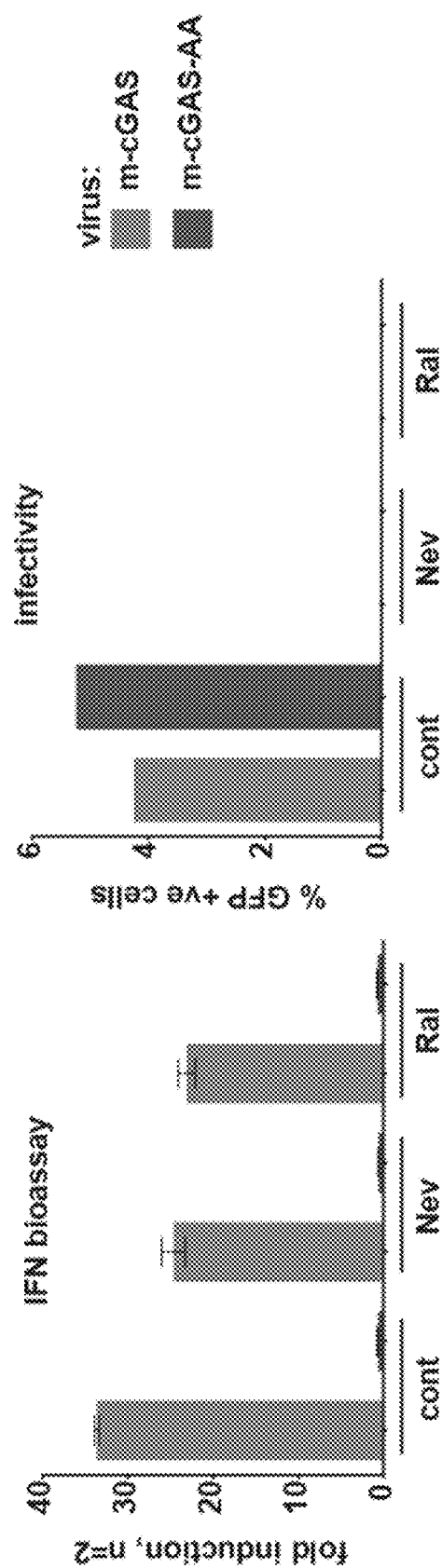
Figure 3D:
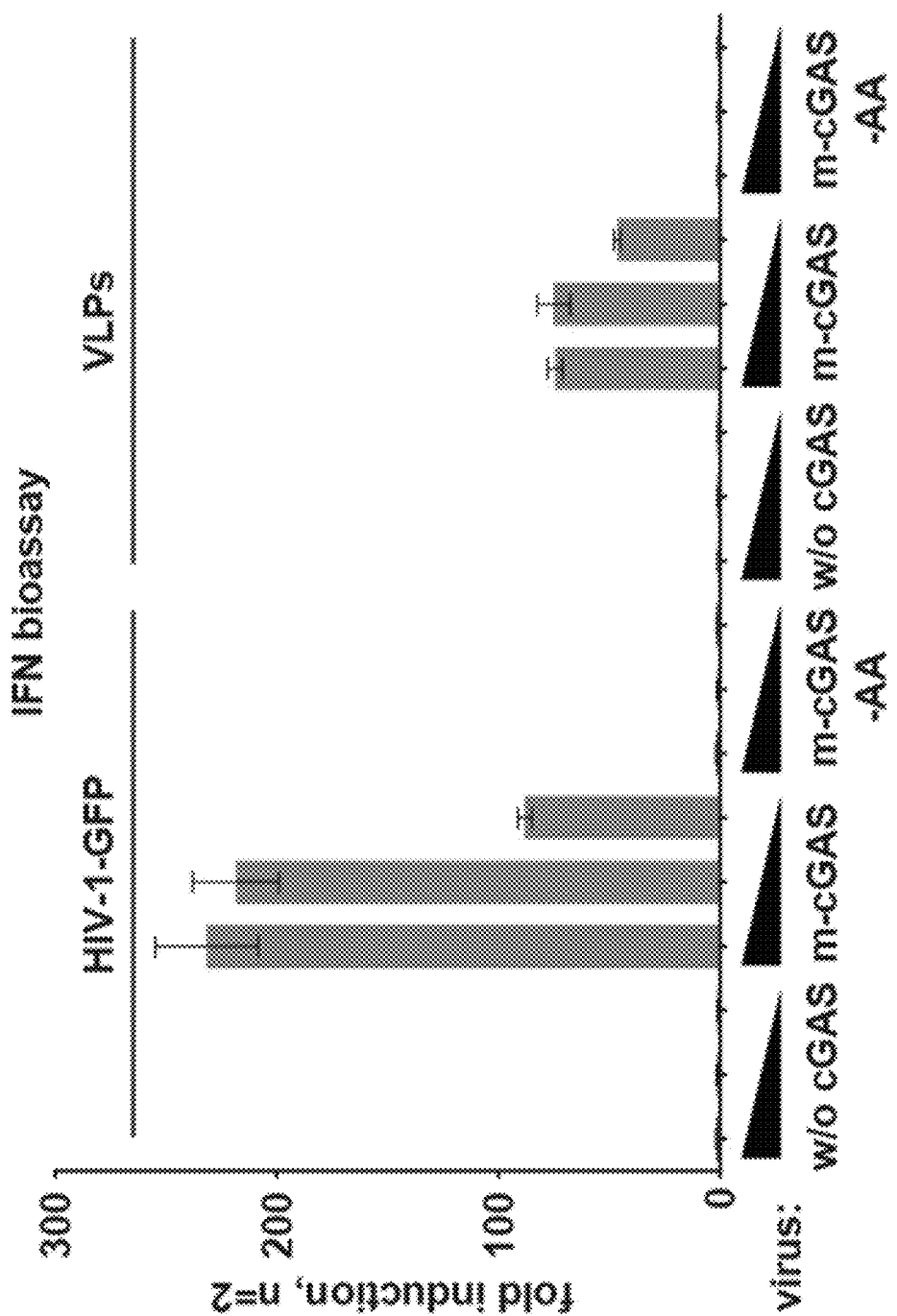
Figure 3E:
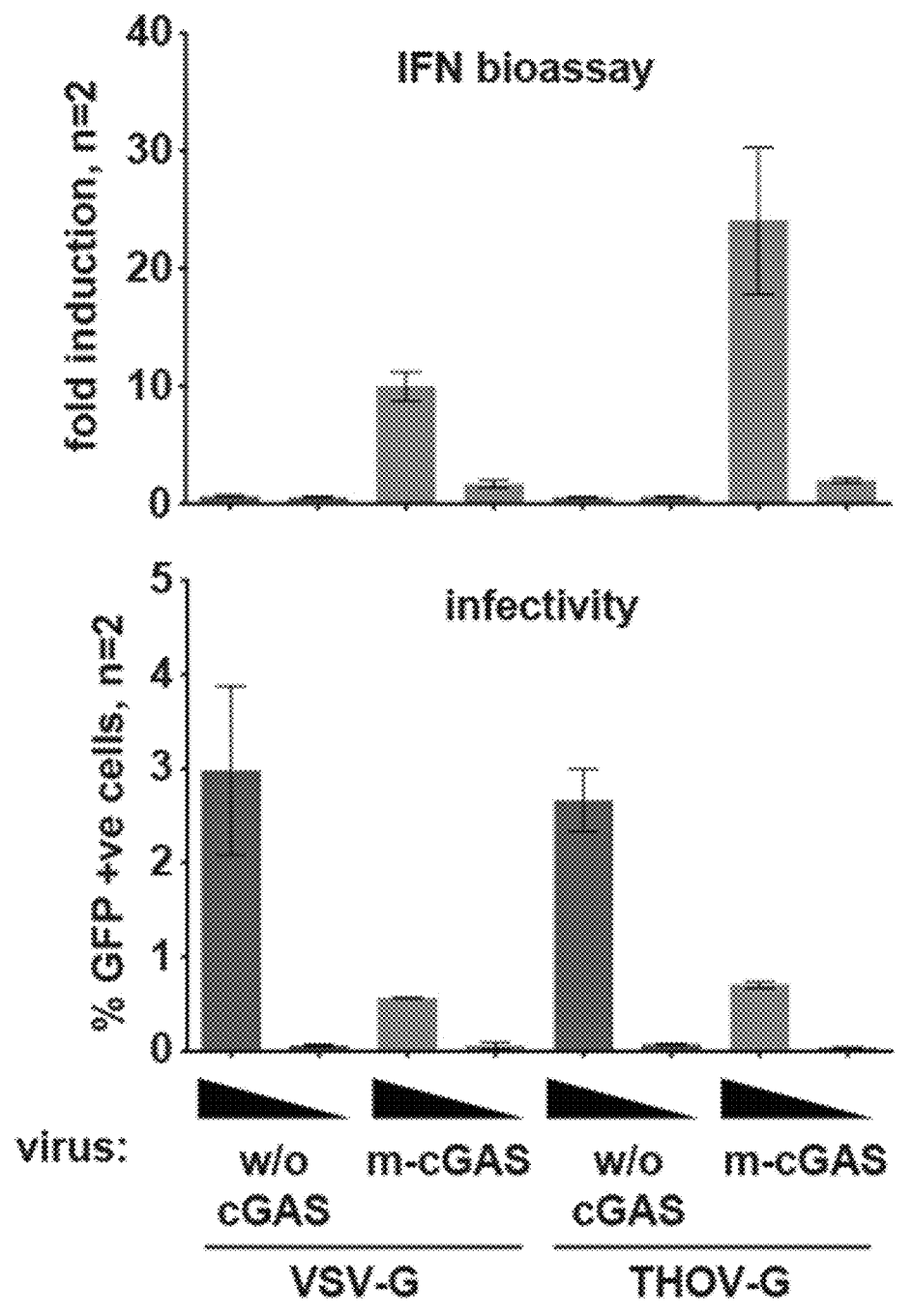
Figure 3F:
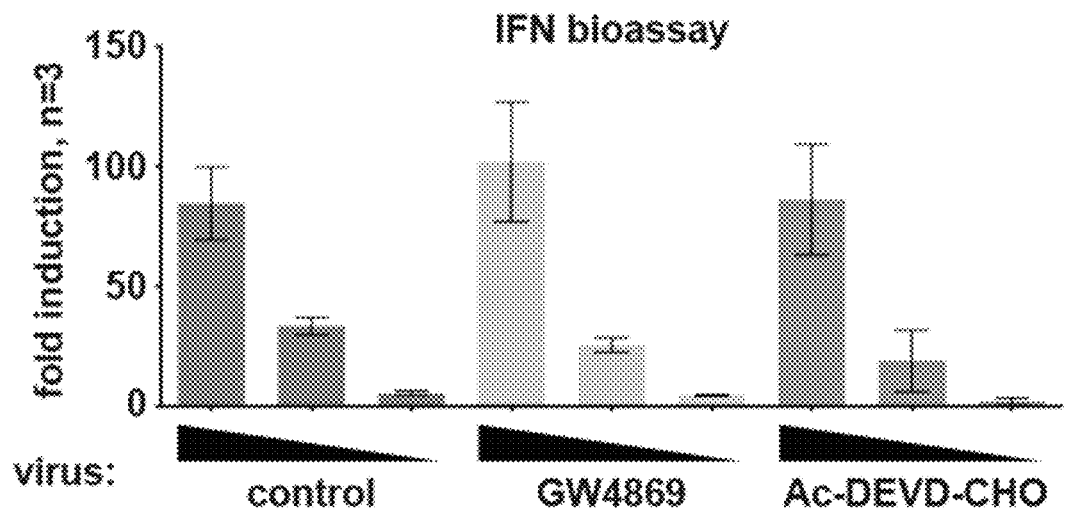

To exclude the possibility that transfer of plasmid DNA or of a soluble factor accounts for IFN production by freshly infected cells, the inventors treated virus preparations with DNase or pelleted virions by centrifugation. Neither treatment impacted the ability of HIV-1-GFP produced in cGAS expressing cells to induce IFN (FIGS. 3A, B). Moreover, the IFN response in target cells was independent of reverse transcription and integration, as shown by pharmacological inhibition with nevirapine and raltegravir, respectively (FIG. 3C). In addition, virus-like particles lacking a viral RNA genome induced IFN in target cells when collected from cGAS expressing producer cells (FIG. 3D), demonstrating that neither the viral genome nor its reverse transcription products account for IFN induction in this setting. Substitution of VSV-G with thogotovirus glycoprotein did not diminish the IFN inducing property of virus stocks from cGAS expressing cells, demonstrating that these effects are not related to VSV-G pseudotyping (FIG. 3E). It is possible that HIV-1-GFP stocks contain exosomes and other enveloped vesicles such as apoptotic bodies. Treatment of cGAS-reconstituted producer cells with the exosome inhibitor GW4869 (Li et al., 2013, *Nat Immunol*, 14, 793-803) or the caspase inhibitor Ac-DEVD-CHO during virus preparation did not diminish IFN induction by HIV-1-GFP (FIG. 3F), consistent with the idea that the IFN inducing activity is present within virions.

Figures 2E, 2F:
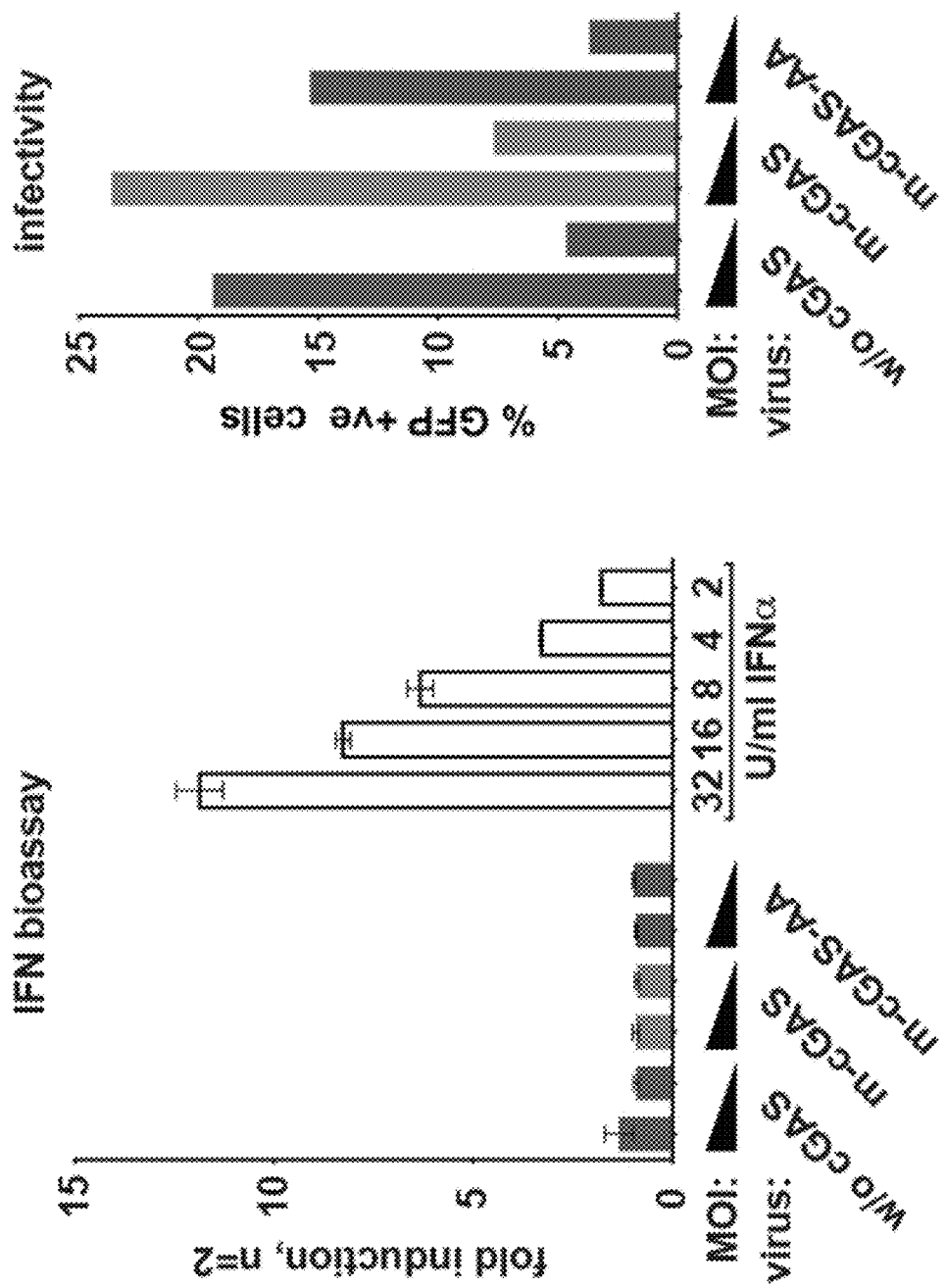
Figure 4A:
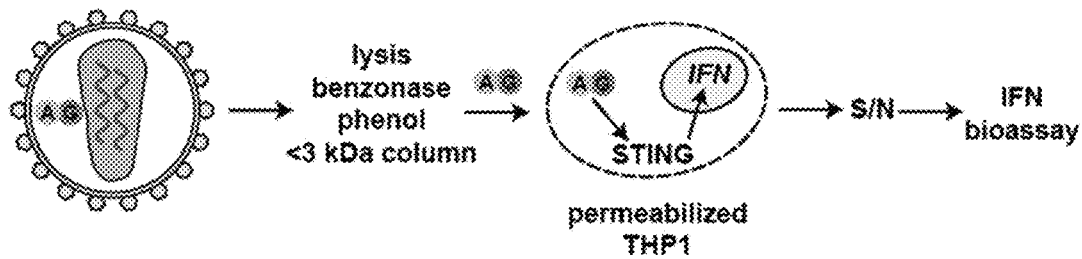
Figure 4B:
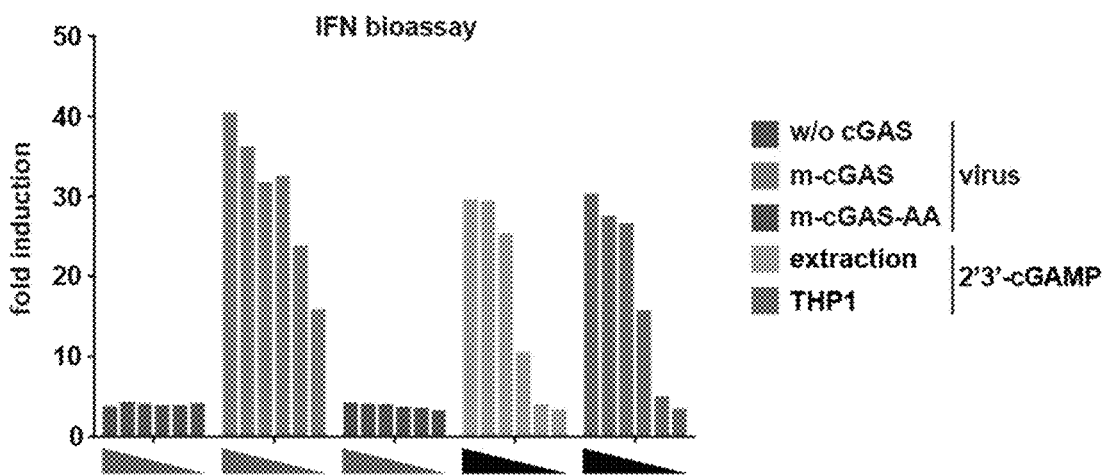
Figure 4C:
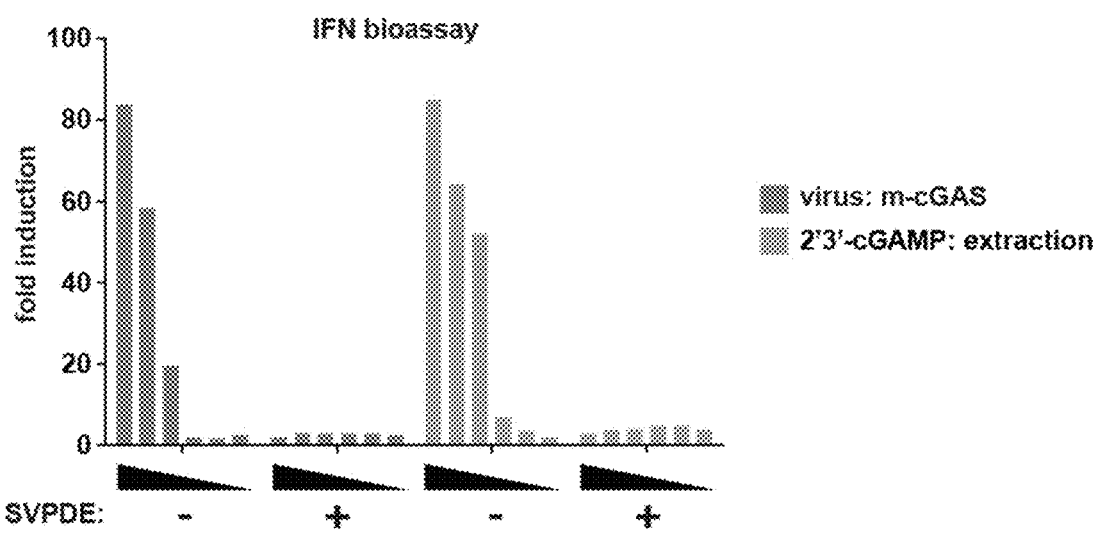
Figure 4D:
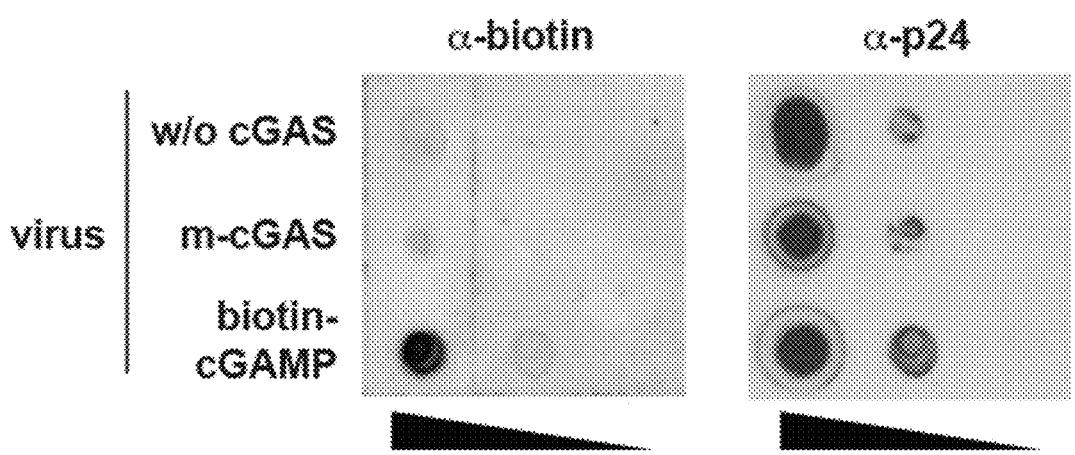

Next, the inventors prepared small molecule extracts from virus preparations. In the course of this protocol, proteins and nucleic acids are degraded and removed. Virus extracts were added to PMA differentiated THP1 cells that were mildly permeabilized with digitonin and the inventors analyzed IFN secretion (FIG. 4A). Extracts from HIV-1-GFP collected from wild-type cGAS reconstituted producer cells induced IFN secretion by THP1 cells in a dose-dependent manner (FIG. 4B). Pre-incubation of extracts with snake venom phosphodiesterase I, which cleaves cGAMP, abrogated this effect (FIG. 4C). To further test whether cGAMP is present in lentiviral particles, the inventors transfected virus producer cells with biotin-labeled cGAMP. Pelleted virus stocks were spotted on a nylon membrane that was then probed with streptavidin. Biotin-cGAMP was indeed detectable in virus preparations (FIG. 4D). Whether the incorporation of cGAMP into virus particles is a selective process or is based on diffusion remains to be determined. It is likely that the lipid envelope of HIV-1 encompasses cGAMP in the virus particle upon budding from an infected cell. Consistent with this notion, non-enveloped adenovirus produced in cGAS-reconstituted cells did not induce IFN in newly infected cells (FIGS. 2E-F).

Taken together, these data show that cGAMP can be packaged into enveloped lentiviral virions and induces IFN via STING in newly infected cells. These results have implications for gene therapy and vaccination as the incorporation of cGAMP in lentiviral vectors, which are typically produced in cGAS-deficient 293T cells, may be undesirable in the former case but advantageous in the latter case. Indeed, virus stocks containing cGAMP potently induced IFN and the expression of the co-stimulatory molecule CD86 in human dendritic cells without Vpx-delivery (FIG. 5).

The cGAS pathway is uniquely characterized by employing the small diffusible molecule cGAMP and this has interesting implications for the induction of innate immune responses. For example, cGAMP can diffuse from virus-infected cells across gap junctions into neighboring uninfected cells, in which an antiviral state is induced via STING. Here, the inventors show that cGAMP can additionally be packaged into HIV-1 particles and that infection of target cells results in delivery of cGAMP into the cytosol and subsequent triggering of STING. This Trojan horse mechanism allows productively infected cells to transfer their knowledge of the presence of infection to other cells. This may act to broaden the spectrum of cells that initiate an IFN response as reverse transcription, which is inhibited in some cells by SAMHD1, is not required for virus sensing via cGAMP transfer. In addition, the transfer of cGAMP in virus particles may accelerate the IFN response. Finally, it is tempting to speculate that other enveloped viruses carry cGAMP in their virions. In sum, the inventors have identified a novel mechanism by which a signal for innate immunity is transferred between cells.

Materials and Methods

Plasmids

FLAG-m-cGAS, FLAG-m-cGAS-G198A/S199A and m-Sting-HA pcDNA constructs have been described elsewhere (Sun et al., 2013, *Science*, 339, 786-791; Burdette et al., 2011, *Nature*, 478, 515-518). pNL4-3-deltaE-EGFP was from the NIH AIDS reagent program. pCAAGS-THOV-G was from G. Kochs. pGreenFire-ISRE was purchased from System Biosciences. pSIV4+, pVSV-G, p125-F-Luc and pRL-TK have been described before (Rehwinkel et al., 2013, *EMBO J*, 32, 2454-2462; Rehwinkel et al., 2010, *Cell*, 140, 397-408).

Cells

BMDMs were obtained from fresh bone marrow using 20% L929 supernatant as described (Rehwinkel et al., 2013, *EMBO J*, 32, 2454-2462). Human dendritic cells were derived from CD14$^+$ monocytes with 40 ng/ml GM-CSF and 40 ng/ml IL-4 (Peprotech) for 5 days. The purity of dendritic cells was >95% according to DC-SIGN staining. CD14$^+$ monocytes were isolated from PBMCs using MACS separation columns and CD14 microbeads (Miltenyi). PBMCs were harvested from CD leukocyte cones (NHS Blood & Transplant, Bristol, UK) using lymphoprep (Alere, UK). HEK293 cells and 293T cells were grown in DMEM medium. THP1 cells, BMDMs and human dendritic cells were grown in RPMI 1640 medium. All media contained 10% FCS and 2 mM glutamine. 100 units/ml penicillin, 100 mg/ml streptomycin and 50 μM 2-mercaptoethanol were additionally added to the RPMI medium used for BMDMs and human dendritic cells.

Antibodies, Western Blot and FACS

α-hSTING antibody was from Cell Signaling (cat. nb. 3337s; 1:1000) and was used for Western blot with secondary HRP-coupled antibody (GE Healthcare Life Sciences; cat. no. NA934; 1:5000). α-FLAG and α-actin HRP conjugated antibodies were from Sigma (cat. no. A8592, 1:5000 and A3854, 1:10,000). α-CD86 PE (clone IT2.2) and α-CD209 (DC-SIGN) APC (clone eB-h209) were from eBioscience. 1 µg/ml DAPI (Sigma Aldrich) was used to exclude dead cells. FACS data were acquired on Beckman Coulter CyAn or BD Biosciences LSRFortessa cell analyzers.

Mice

STING-deficient (Mpys$^{-/-}$) animals have been described before (Jin et al., 2011, *The Journal of Immunology*, 187, 2595-2601) and are on a C57BL/6 background. Femurs and tibias were obtained from humanely killed animals aged 2-3 months and from age and gender matched C57BL/6 wild-type control animals. This work was performed in accordance with the UK Animals (Scientific Procedures) Act 1986 and institutional guidelines for animal care. This work was approved by a project license granted by the UK Home Office (PPL No. 40/3583) and was also approved by the Institutional Animal Ethics Committee Review Board at the University of Oxford.

IFN Bioassay

Human IFN reporter cells were generated by transducing HEK293 cells with pGreenFire-ISRE derived lentivirus. Single clones were established by limiting dilution and clone 3C11 was selected based on its responsiveness to IFN. For the bioassay, cells were overlaid with cell culture supernatant and after 24 hours luciferase expression was quantified using One-Glo Luciferase Assay System (Promega) according to manufacturer's instructions. The detection limit of the bioassay is 1.6 U/ml hIFNα2 (R&D Systems) as shown in FIG. 2C.

RT Q-PCR

RNA extraction from cells, reverse transcription and quantitative PCR have been described (Rehwinkel et al., 2013, *EMBO J*, 32, 2454-2462). Predeveloped TaqMan assay reagents containing primers and fluorescent probe for human 18S rRNA, IFNβ, IFI-44 and IFIT1 and for murine GAPDH, IFIT1 and IFI-44 were from Applied Biosystems.

HIV-1-GFP Production

VSV-G pseudotyped HIV-1-GFP was produced in 293T cells transfected with pNL4-3-deltaE-EGFP, pVSV-G and m-cGAS (or m-cGAS-AA) at a ratio of 2:1:2 using FuGene HD (Promega, cat. no. E2311). THOV-G pseudotyped virus was produced with pCAAGS-THOV-G instead of VSV-G and using a plasmid ratio of 1:1:1. Medium was replaced the following day. At this point, DEVD (60 µM; A0835, Sigma) and GW4869 (20 µM; D1692, Sigma) were added in some experiments. After an additional 48 hours, supernatants were filtered (0.22 µm) and, if required, concentrated by centrifugation over a 20% sucrose cushion (64,000 g, 2.5 hours, 4° C.). Viral titres were determined as infectious units/ml by infection of 293T cells with a dilution series of virus stocks, followed by FACS analysis of GFP expression.

HIV-1-GFP containing biotin-cGAMP was produced as above in 293T cells transfected with pNL4-3-deltaE-EGFP, pVSV-G and biotin-cGAMP (Biolog, cat. no. 157-001) at a ratio of 2:1:1.6 using FuGene HD.

VLPs were produced by transfecting 293T cells with pSIV4+(Vpx deficient), pVSV-G and m-cGAS or m-cGAS-AA at a ratio of 2:1:2. The medium was exchanged the following day. After an additional 48 hours, VLPs were collected and processed as HIV-1-GFP (see above).

HIV-1-GFP Infection $10^5$ HEK293 were seeded in 24-wells. After 24 hours, virus stocks were added in the presence of polybrene (8 µg/ml). 18 hours later the medium was exchanged. After additional 48 to 72 hours supernatants and cells were harvested for IFN bioassay and FACS analysis or RT Q-PCR analysis, respectively.

For the IFNβ promoter reporter assay, cells were additionally transfected with 125 ng p125-F-Luc and with 25 ng pRL-TK using lipofectamine 2000. This was done 6-8 hours prior to infection. Luciferase activity was analysed 24 hours after infection and F-Luc activity was normalized to R-Luc. In some experiments, cells were treated for 1 hour prior to infection with nevirapine (5 µM; cat. no. 4666; NIH AIDS reagent program) or raltegravir (5 µM; cat. no. 11680; NIH AIDS reagent program). Alternatively, virus stocks or cGAS plasmid were pre-treated with DNase I (40 µg/ml; Roche, 11284932001) for 1 hour at 37° C. prior to infection.

4-8×$10^5$ BMDMs were seeded in 12-wells and, after O/N incubation, were infected in the presence of polybrene (8 µg/ml) by spin-infection (1100 g; 90 min; room temperature). The inoculum was then removed and fresh medium was added. Supernatant and cells were harvested 24 hours later. mIFNα was detected by ELISA as described in Rehwinkel et al., 2013, *EMBO J*, 32, 2454-2462.

0.5×$10^5$ human dendritic cells were seeded in 24-wells and infected for 2 hours in the presence of polybrene (8 µg/ml). The inoculum was washed away and the cells were incubated for 48 hours with fresh medium. The cells were harvested for FACS analysis and the supernatant was tested with the IFN bioassay.

Adenovirus

Adenovirus was produced in HEK293 cells transfected with m-cGAS or m-cGAS-AA using FuGene HD or in untransfected cells. 2 hours after transfection, cells were infected with AdenoCreGfp virus (cat. no. 1700, Vector Biolabs) at an MOI of 1. Virus was harvested 48 hours later from cells by three cycles of freeze, thaw and sonication.

Fresh HEK293 cells were infected for 18 hours. Cells were then washed and provided with new medium. After 48 additional hours, supernatants were harvested for analysis with the IFN bioassay and cells were collected for FACS analysis.

Sendai Virus

Sendai virus was from LGC Standards (cat. no. VR-907). Cells were infected by addition of Sendai virus to the culture medium.

Small Molecule Extractions and THP1 Stimulation

The method for small molecule extraction from virions was adapted from Ablasser et al., 2013, *Nature*, 498, 380-384. Pelleted virions were resuspended in lysis buffer (1% Triton X-100, 10 mM Tris-HCl, pH 7.4, 1 mM NaCl, 1 mM EDTA and 3 mM MgCl$_2$) and left on ice for 20 min. Lysates were clarified by centrifugation for 10 min at 1000 g at 4° C. To remove nucleic acids, samples were treated for 45 min with 50 U/ml benzonase (Sigma) on ice. Next, proteins were eliminated by two sequential phenol-chloroform extractions followed by a chloroform wash to remove traces of phenol. The extract was filtered using Amicon Ultra 3 kDa centrifugal filters (Millipore, cat. no. UFC500396) and the filtrate was concentrated by centrifugation under vacuum. Samples were resuspended in 20 µl water and stored at −80° C. until further use.

100,000 THP-1 cells treated with 30 ng/ml PMA were seeded in 96-well plates and left overnight. Cells were then washed with medium and overlaid with 25 µl permeabilisation buffer (10 g/ml digitonin, 50 mM Hepes, pH 7.4, 100 mM KCl, 3 mM MgCl$_2$, 0.1 mM DTT, 85 mM sucrose, 0.2% BSA, 1 mM ATP and 0.1 mM GTP) containing virion extracts or 2'3'-cGAMP standard (cat. no. C161-005, Biolog) for 30 min at 37° C. Next, cells were washed with medium and 75 μl fresh medium was added. After 24 hours, supernatant was tested in the IFN bioassay.

In some experiments, 5 μl extract or 1 μg cGAMP were incubated in 50 mM Tris, pH 8.8, and 10 mM MgCl$_2$ with or without 0.002 units SVPDE (cat. no. P3243, Sigma) at 37° C. for 1 hour. Treated extracts and cGAMP were then serially diluted in permeabilisation buffer and added to THP1 cells as above.

Dot Blot

Virus preparations were resuspended in lysis buffer (1% Triton X-100, 10 mM Tris-HCl pH 7.4, 1 mM NaCl, 1 mM EDTA and 3 mM MgCl$_2$) and blotted onto a nylon membrane (Zeta-Probe GT membrane, cat. no. 162-0197, Bio-Rad), which was left to dry and UV cross-linked (UV Stratalinker 2400; 2× Autocross link, 120,000 μJ/cm$^2$). Biotin-cGAMP was detected with streptavidin-HRP (cat. no. 3310-9, Mabtech, 1:1000). HRP was inactivated with 0.2% sodium azide and the absence of residual signal was validated by exposing the membrane for one hour. The membrane was then reprobed with mouse α-p24 (cat. no. 4313, Advanced Bioscience Laboratories, 1:5000) followed by α-mouse HRP (cat. no. NA931VS, GE Healthcare Life Sciences, 1:3000).

Example 2

Results

Figure 6A:
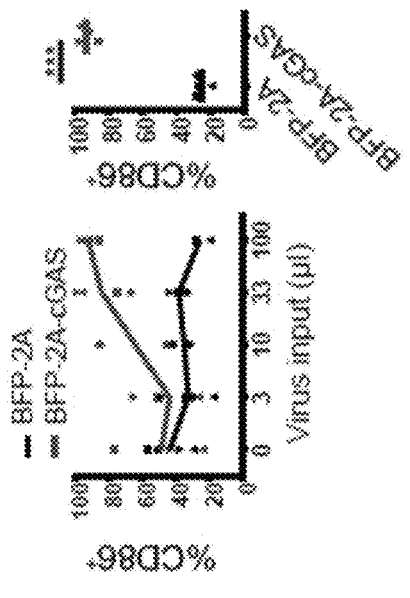
Figure 6B:
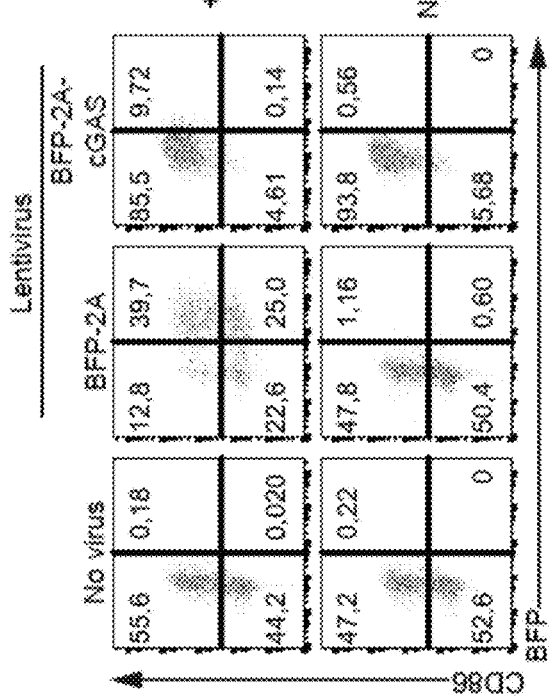
Figure 7A:
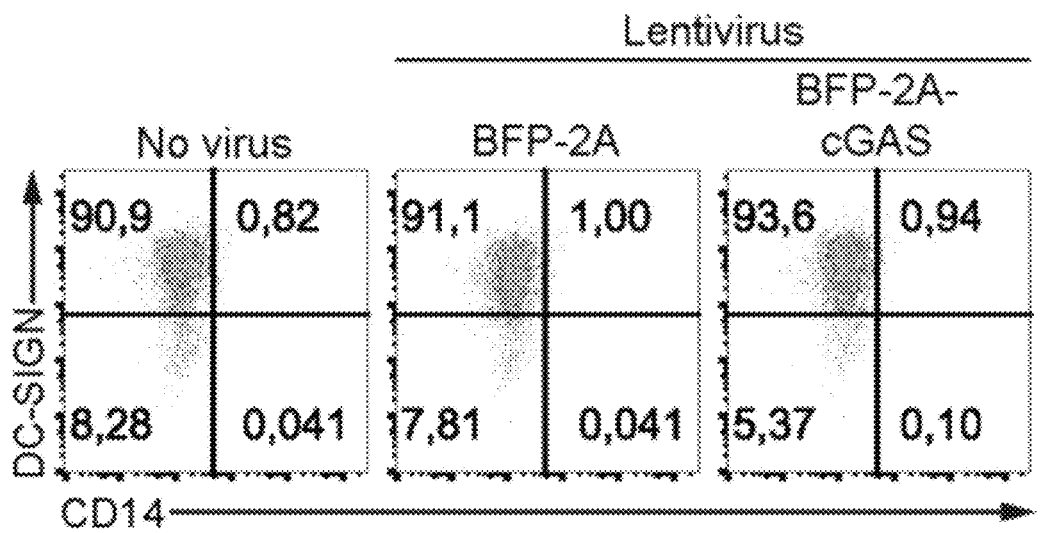
Figure 7B:
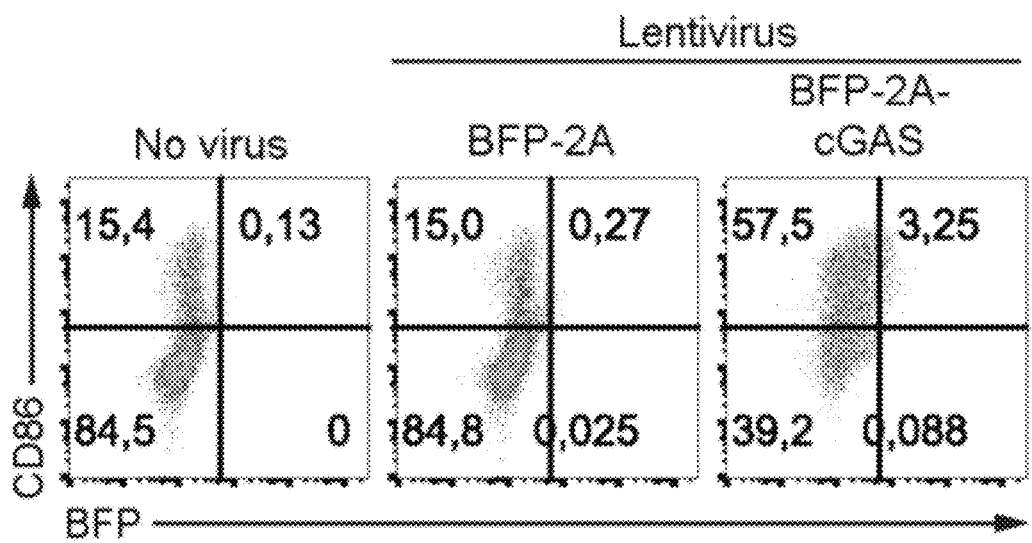
Figure 7C:
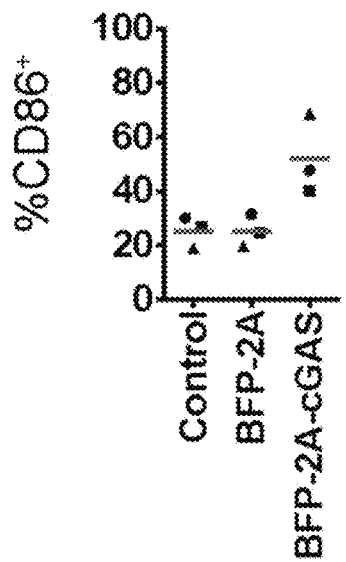

To study cGAS function, the inventors sought to manipulate its expression in human monocyte-derived DCs (Dendritic Cells). They generated a lentiviral vector expressing cGAS, produced lentiviral particles and infected monocytes with the cell-free viral supernatant before differentiating them in DCs. At day 4 of differentiation, the majority of differentiated DCs exposed to the cGAS virus expressed CD86 and were therefore activated, although the efficiency of transduction as indicated by expression of the reporter fluorescent protein BFP was low (FIG. 6A). In contrast, infection with a lentivirus coding only for BFP efficiently transduced monocytes but did not increase the percentage of activated DCs, as compared to non-virus exposed cells (FIG. 6A). This confirmed that the general process of lentiviral vector infection is not sensed by monocytes and DCs and that it could not be responsible for inducing the activation observed in the case of the cGAS lentiviral vector. Importantly, the DCs were fully differentiated, as shown by expression of DC-SIGN and down-regulation of CD14 (FIG. 7A). The cGAS lentiviral vector also activated DCs that were fully differentiated prior to infection (FIG. 7B, FIG. 7C). This indicated that an activating innate immune signal was present and associated with the apparent process of infection of DCs with a cGAS-expressing lentiviral vector.

Figure 6C:
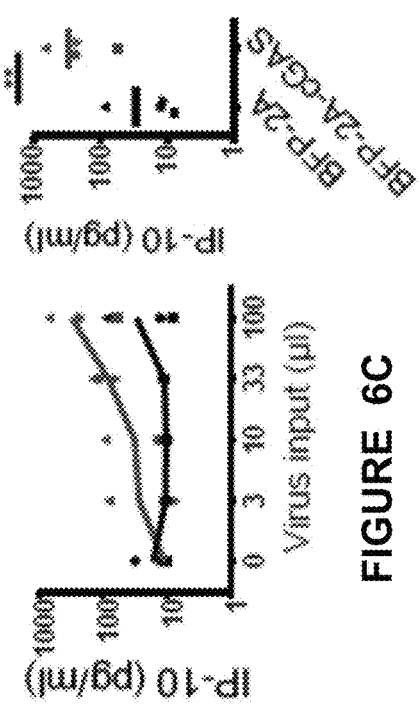
Figure 6D:
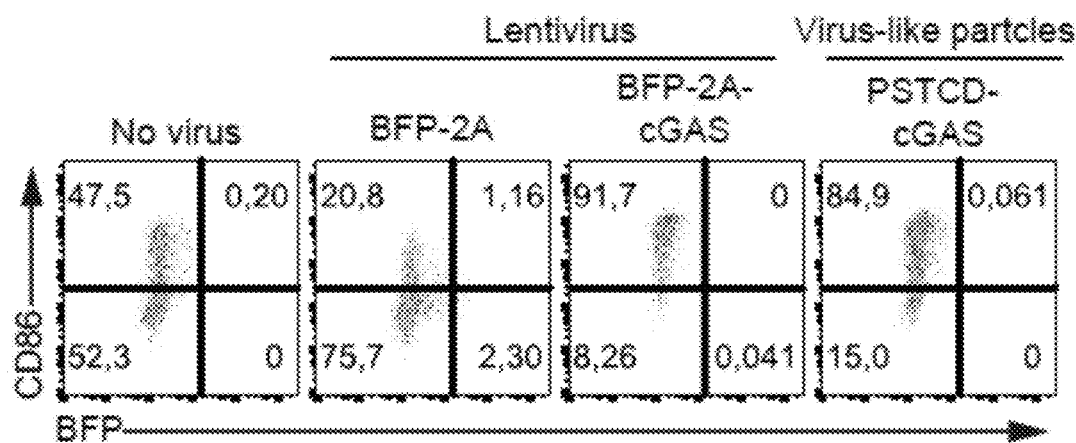
Figure 6E:
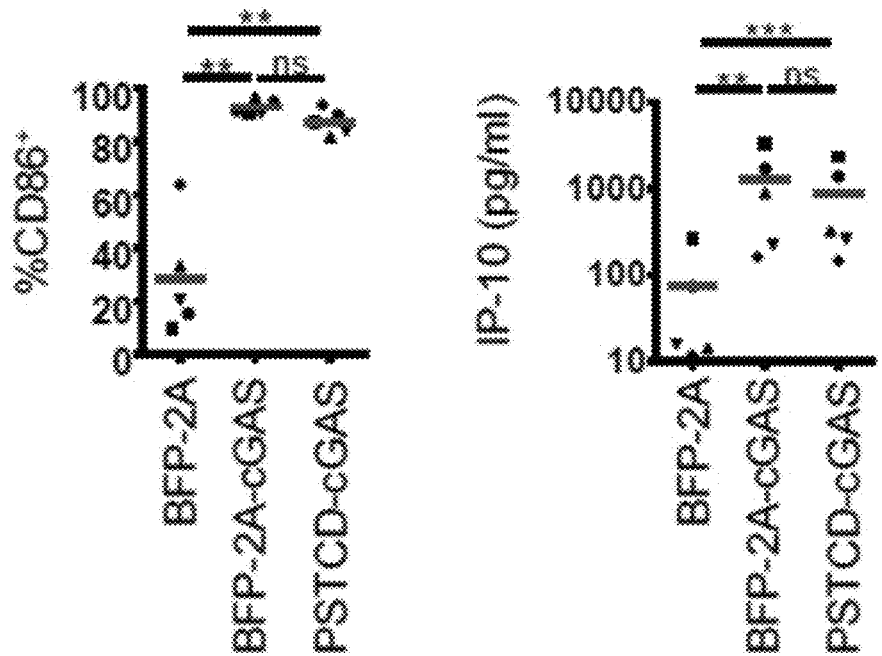
Figure 7D:
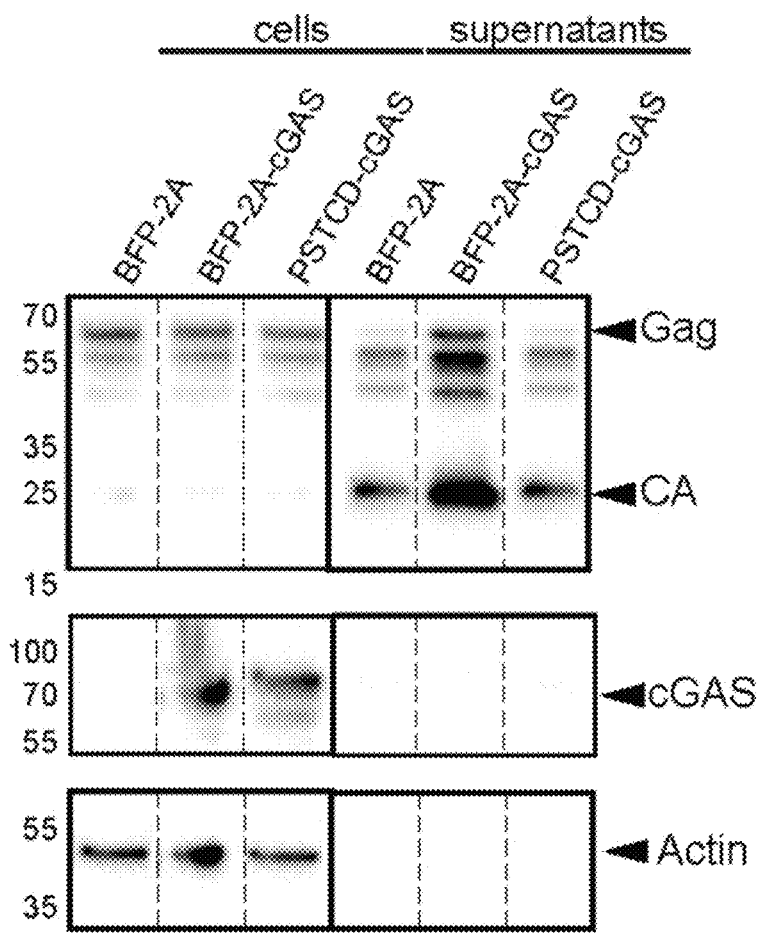

Efficient expression of a lentivirus-encoded gene in DCs requires the lentiviral protein Vpx which alleviates a constitutive restriction to HIV infection imposed by SAMHD1, thus leading to efficient transduction of the cells by the vector. To check whether expression of cGAS in the target cell was required for activation of the cells, the inventors omitted the Vpx protein from the transduction procedure. In this case, the SAMHD1 restriction is active and prevents efficient transduction, as shown by lack of detection of the reporter fluorescent protein BFP with the control virus (FIG. 6A, lower panels). Unexpectedly, activation of the DCs by the cGAS lentivirus was conserved without Vpx (FIGS. 6A, 8B), suggesting that cGAS expression in the target cells was not required. The activation was not restricted to CD86 expression since the type I interferon-inducible cytokine IP-10 (gene CXCL10) was also produced by DCs (FIG. 6C). To confirm this observation and to exclude that a low level of cGAS vector transduction was responsible for the activation, the inventors produced HIV-1 virus-like particles (VLPs) that did not contain a lentiviral genome in cells expressing cGAS from a non-lentiviral plasmid (FIG. 7D). The VLP-containing supernatant from cGAS-expressing cells activated DCs to the same extent as the transduction-competent lentiviral vector, as measured by CD86 expression (FIG. 6D) and IP-10 production (FIG. 6E). Thus, the supernatant from cells that produce viral particles and express cGAS can transmit an innate signal to immune cells.

Figure 8A:
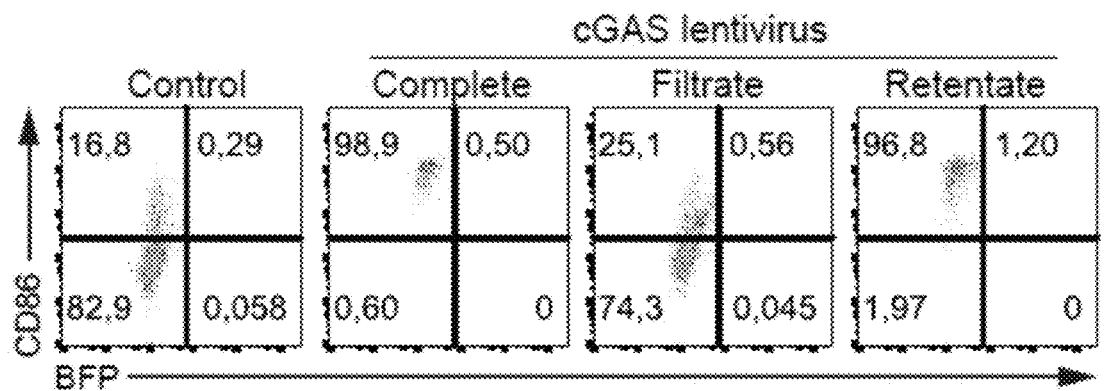
Figure 8E:
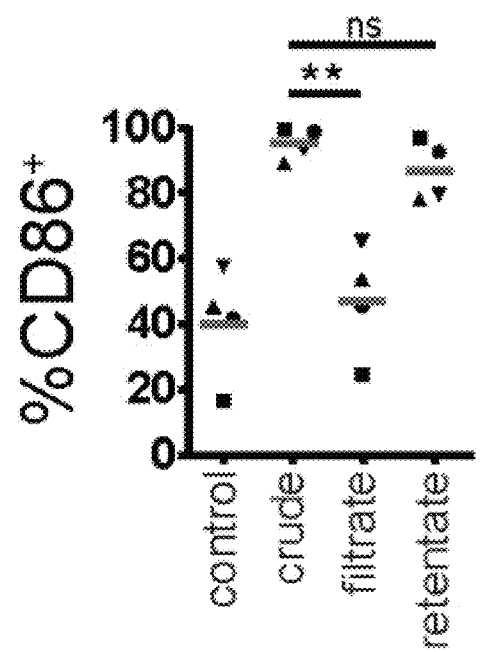
Figure 8B:
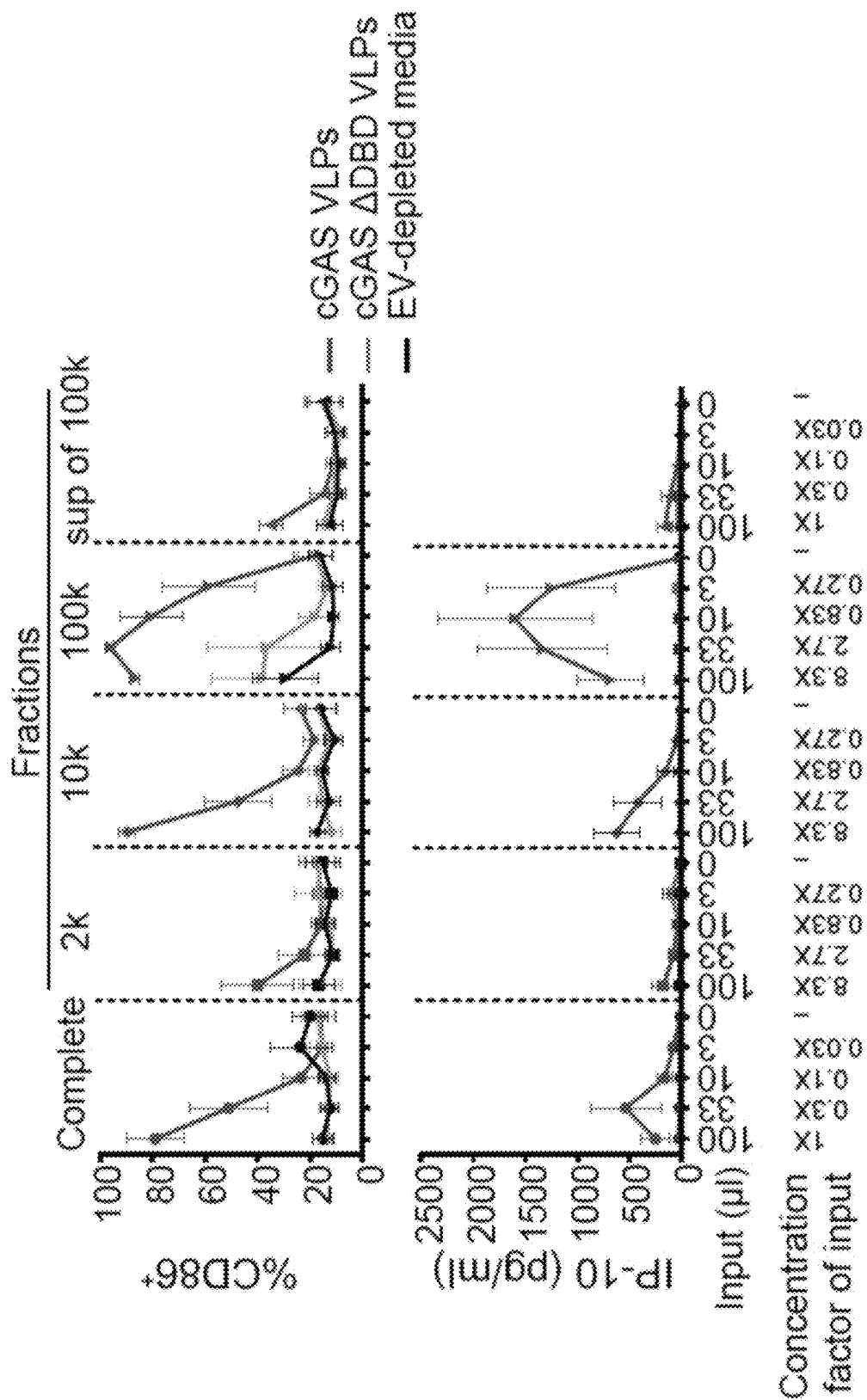
Figures 8C, 8D:
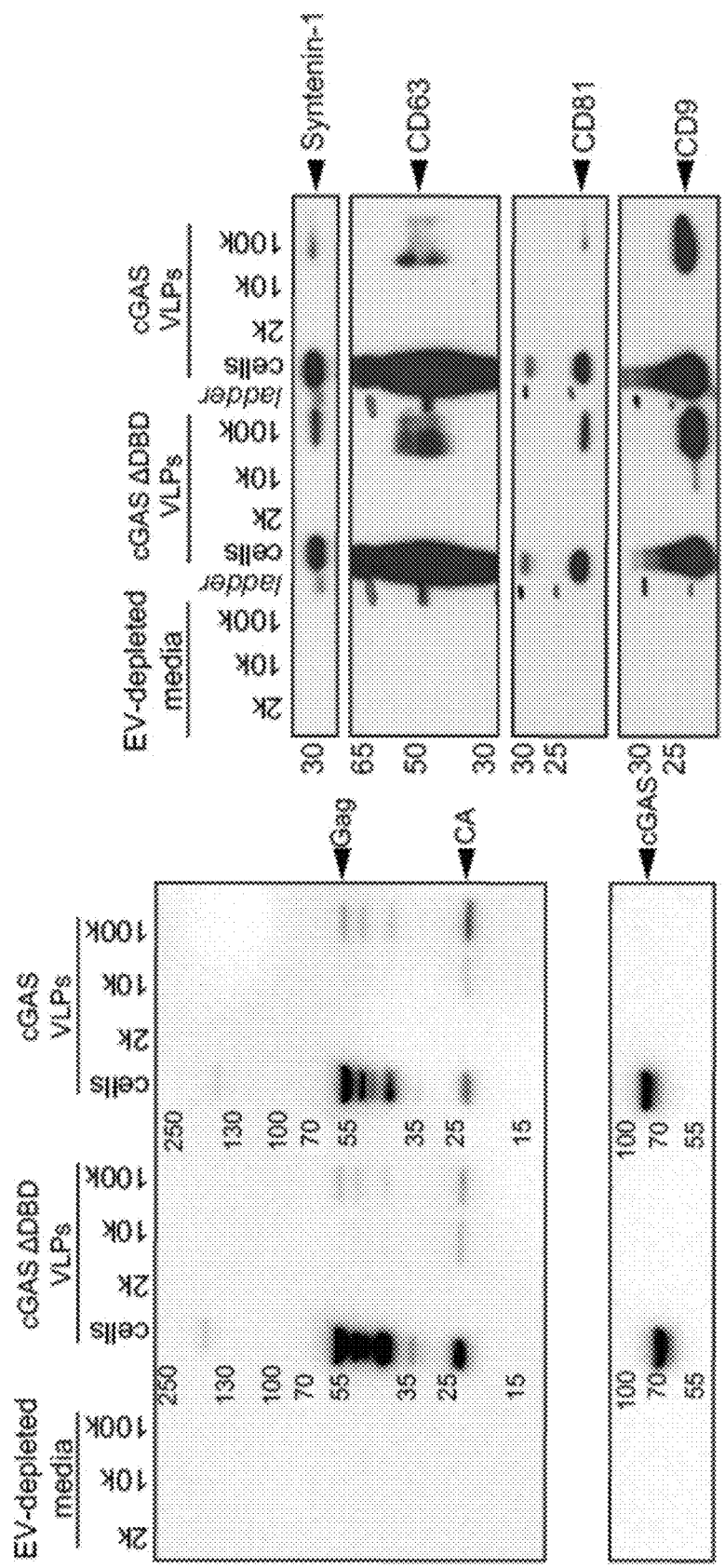

To determine the nature of this signal, the inventors first fractionated viral supernatants over a 10 kDa filter. The retentate efficiently induced CD86 expression and IP-10 production in monocytes, while activity was depleted from the filtrate, indicating that the activity was carried by components larger than 10 kDa (FIG. 8A, FIG. 8E). The inventors then performed differential ultracentrifugation, to separate the various types of membrane-enclosed vesicles released by cells in their medium, collectively called extracellular vesicles (EVs), from soluble factors. Cell debris pellet first (2,000 g), followed by large vesicles such as apoptotic blebs (10,000 g), and finally small EVs including exosomes and viruses (100,000 g). Strikingly, the culture supernatant recovered after these ultracentrifugations had almost completely lost ability to activate monocytes (FIG. 8B). By contrast, most activity was recovered in the 100,000 g pellet, which contained Gag as well as some exosome-associated proteins, the tetraspanins CD63, CD9, and CD81 and the cytosolic syntenin-1 (FIG. 8B, FIG. 8C, FIG. 8D). Some activity was also present in the 10,000 g pellet, which only contained Gag and no exosome markers, whereas the larger cell debris that contained only traces of Gag (not shown) displayed a marginal activity (FIG. 8B, FIG. 8C, FIG. 8D). These results show that the innate signal transferred by cGAS-expressing cells to DCs is contained within small EVs, including Gag-containing viral particles, rather than being a diffusible soluble factor.

The innate signal that is transmitted by EVs could be mediated by packaging and transfer of the cGAS protein to target cells. The inventors did not favor this hypothesis because they could not detect cGAS protein in the pelleted supernatants (FIG. 7D). As an alternative possibility, the second messenger cGAMP could hence transmit the innate signal. cGAMP is a small molecule of 675 Da produced in the cytosol, and could thus be packaged in the viral particles and EVs, since these structures contain cytosol from the producing cells.

The inventors reasoned that if cGAMP was present in the cell-derived viral particles, it should activate a type I interferon response in a STING-dependent but cGAS-independent manner. They transfected an interferon reporter construct with or without a STING plasmid in 293FT cells that lack detectable cGAS expression (data not shown). Delivery of synthetic cGAMP with lipofectamine or transfection of cGAS expression plasmid activated the reporter only in the presence of STING, validating the assay (FIG. 9A, FIG. 9C). VLPs that were produced from cGAS-expressing cells activated the reporter in the presence of STING, but no activation was detected without STING or when the particles were produced in the absence of cGAS (FIG. 9A). Supernatants from cGAS-expressing cells that did not produce VLPs were much less effective at activating the reporter (FIG. 9A). Therefore, viral particles can transmit an innate signal from cGAS in produced cells to STING in target cells. To further demonstrate that cGAMP was present in the viral particles, the inventors used a bioassay based on permeabilized THP-1 and an IFN reporter cell line (FIG. 9B). They extracted small molecules from viral-producing cells and pelleted VLPs. As expected, cGAMP activity was detected from cells transfected with cGAS, but not in control cells. Strikingly, cGAMP activity was also detected in the pelleted VLPs and this activity was lost when they used the catalytic mutant of cGAS E225A/D227A (FIG. 9B).

To confirm that the activity measured in the extracts corresponded to cGAMP, the inventors performed mass spectrometry analysis using synthetic cGAMP. They detected the presence of cGAMP in pelleted VLPs. Overall, these data provide strong indications that viral particles package and transfer the second messenger cGAMP.

Figure 10A:
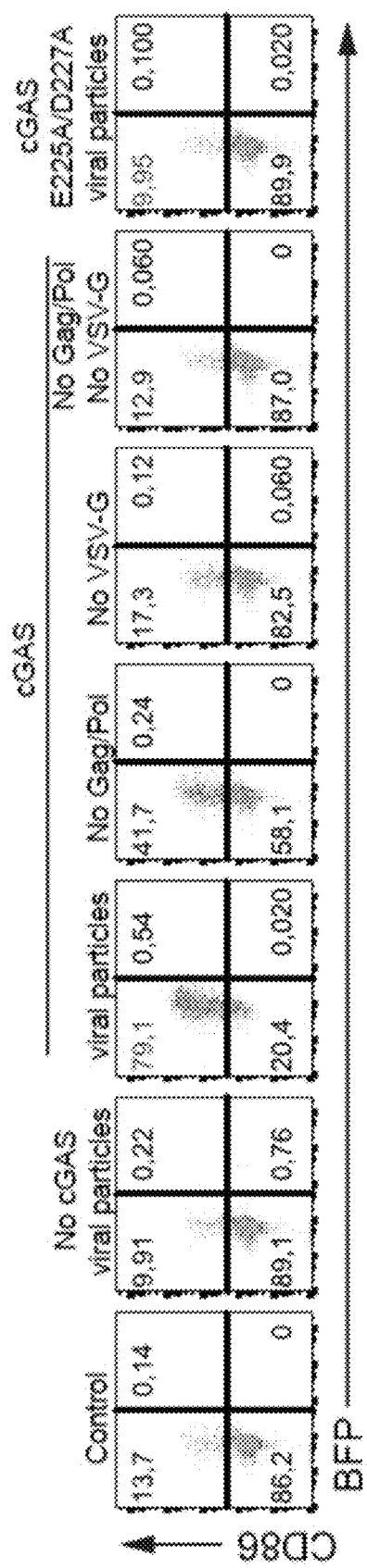
Figures 10B, 10C:
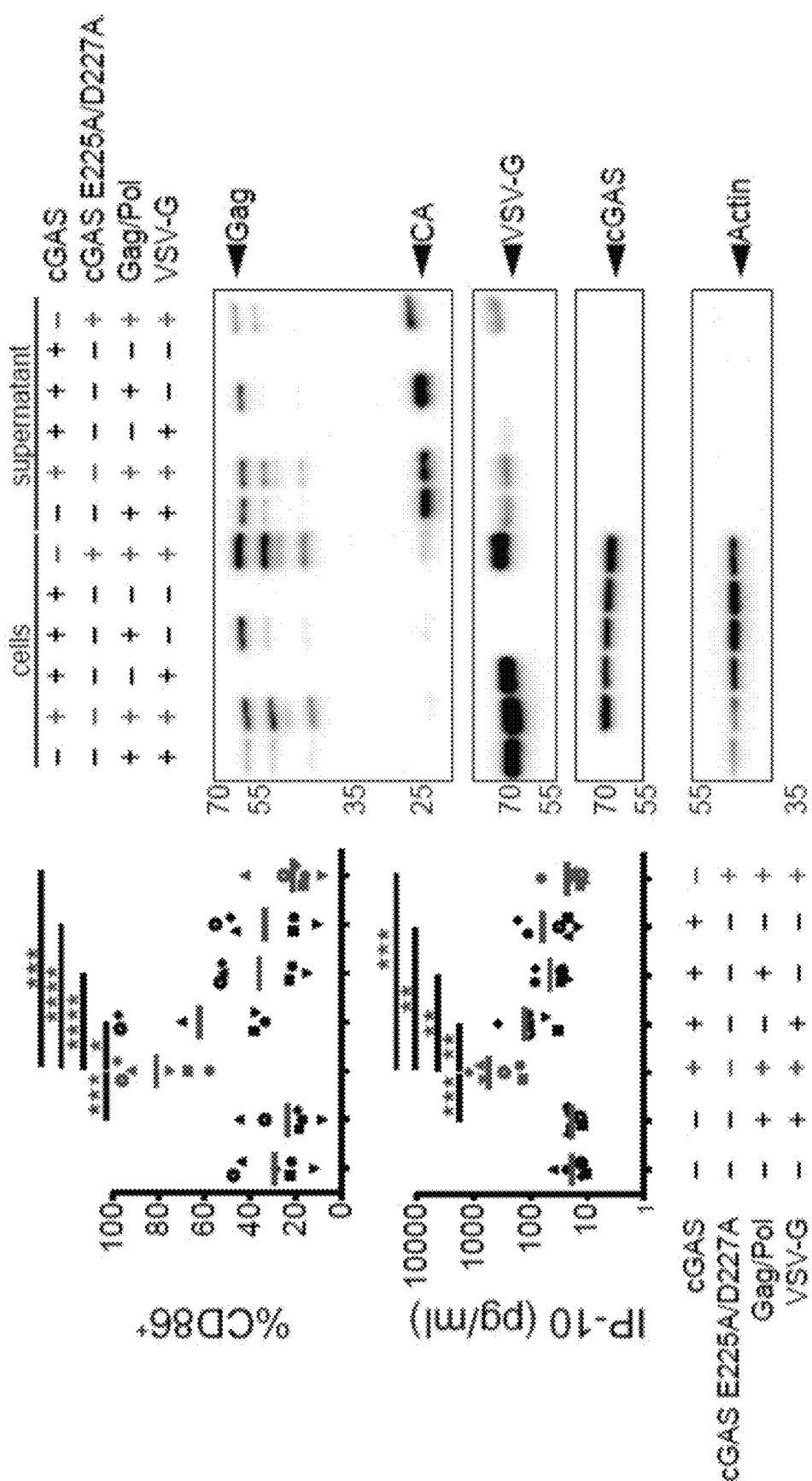

Next, the inventors examined which components were required for transmitting cGAMP. Transmission of cGAMP by the viral particles was abrogated when cGAS E225A/D227A was used, indicating that a functional cGAS protein is required (FIG. 10A). VLPs were produced by expressing the viral protein Gag/Pol and the fusogenic viral envelope protein VSV-G. Omitting expression of either Gag/Pol or VSV-G or both decreased the ability of the supernatants to induce CD86 and IP-10 in DCs (FIGS. 10A, 10B). Absence of VSV-G decreased most strongly DC activation (FIGS. 10A, 10B), indicating that fusogenic extracellular material is the major DC-activating factor. The inventors confirmed that Gag-containing VLPs were still present in the supernatant in the absence of VSV-G, and that VSV-G containing EVs were secreted in the absence of Gag (FIG. 10C). Altogether, this indicates that cGAS and fusion-competent EVs including viral particles are required for transmitting cGAMP.

Figure 10D:
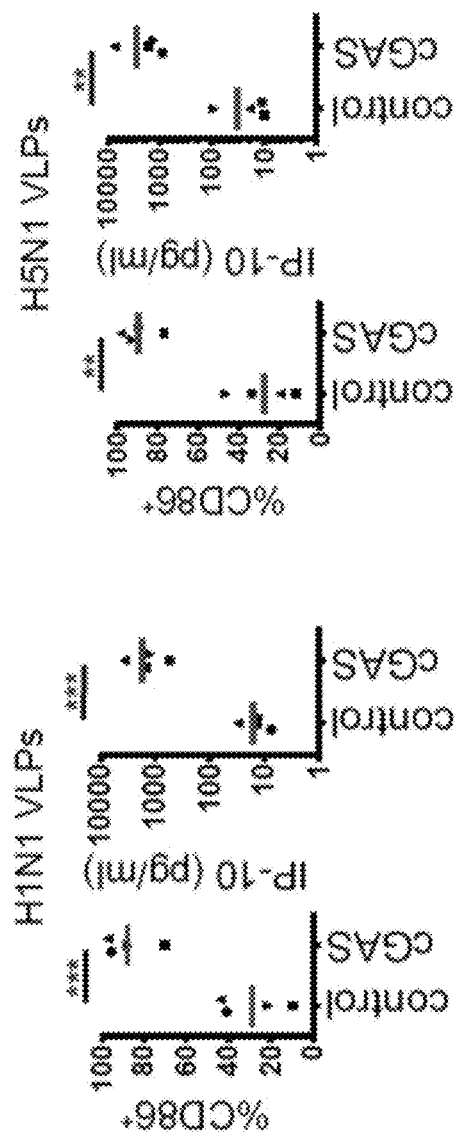
Figure 10F:
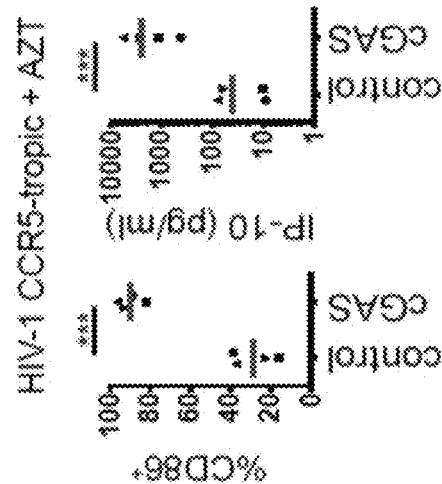
Figure 10E:
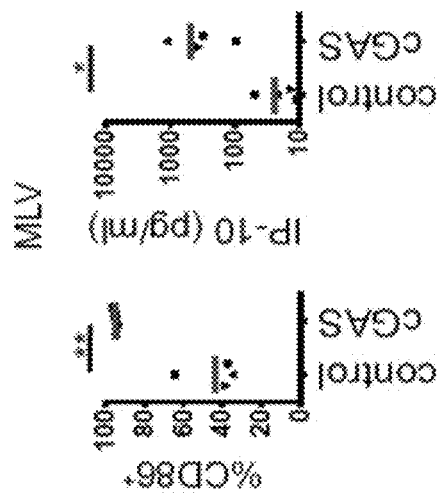
Figure 11A:
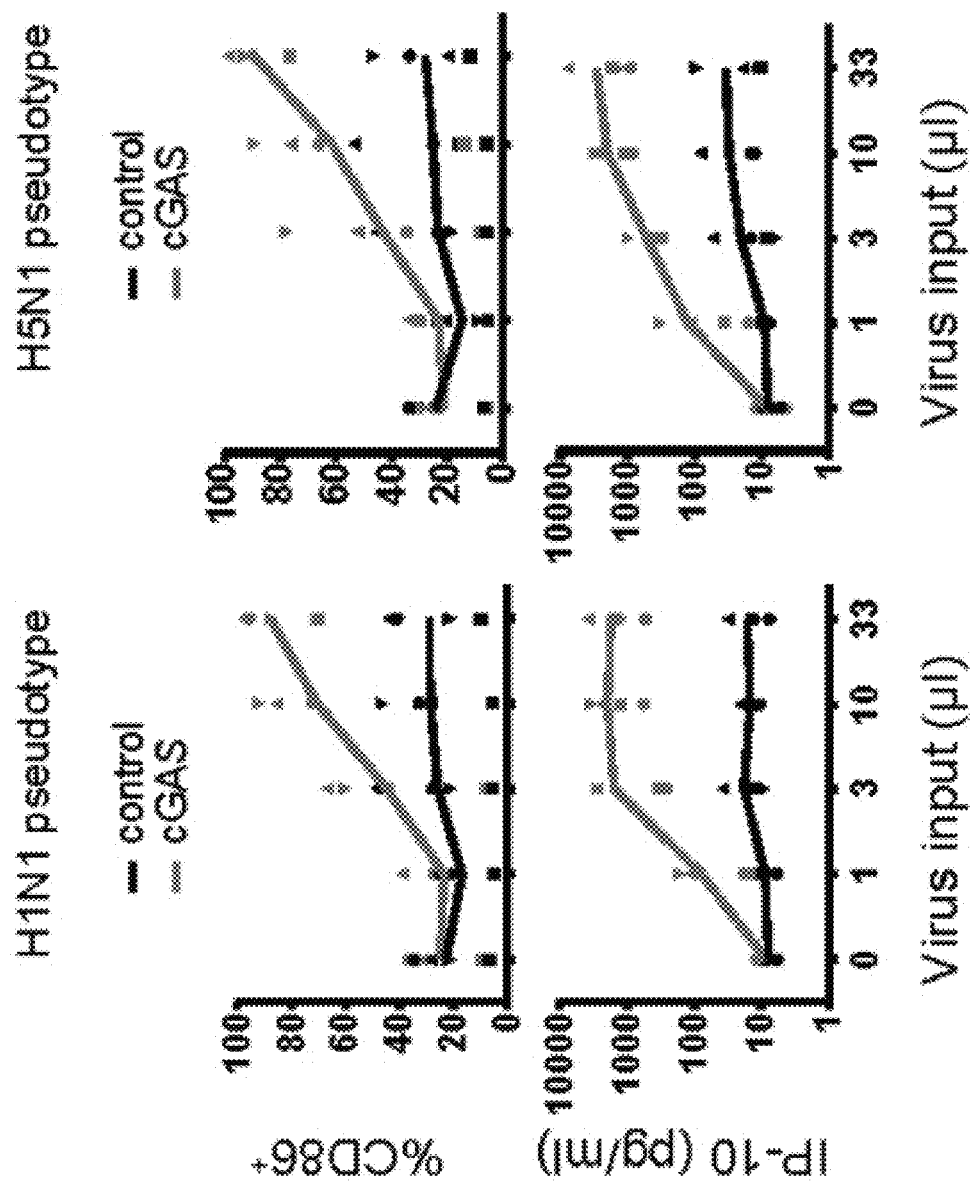
Figures 11B, 11C:
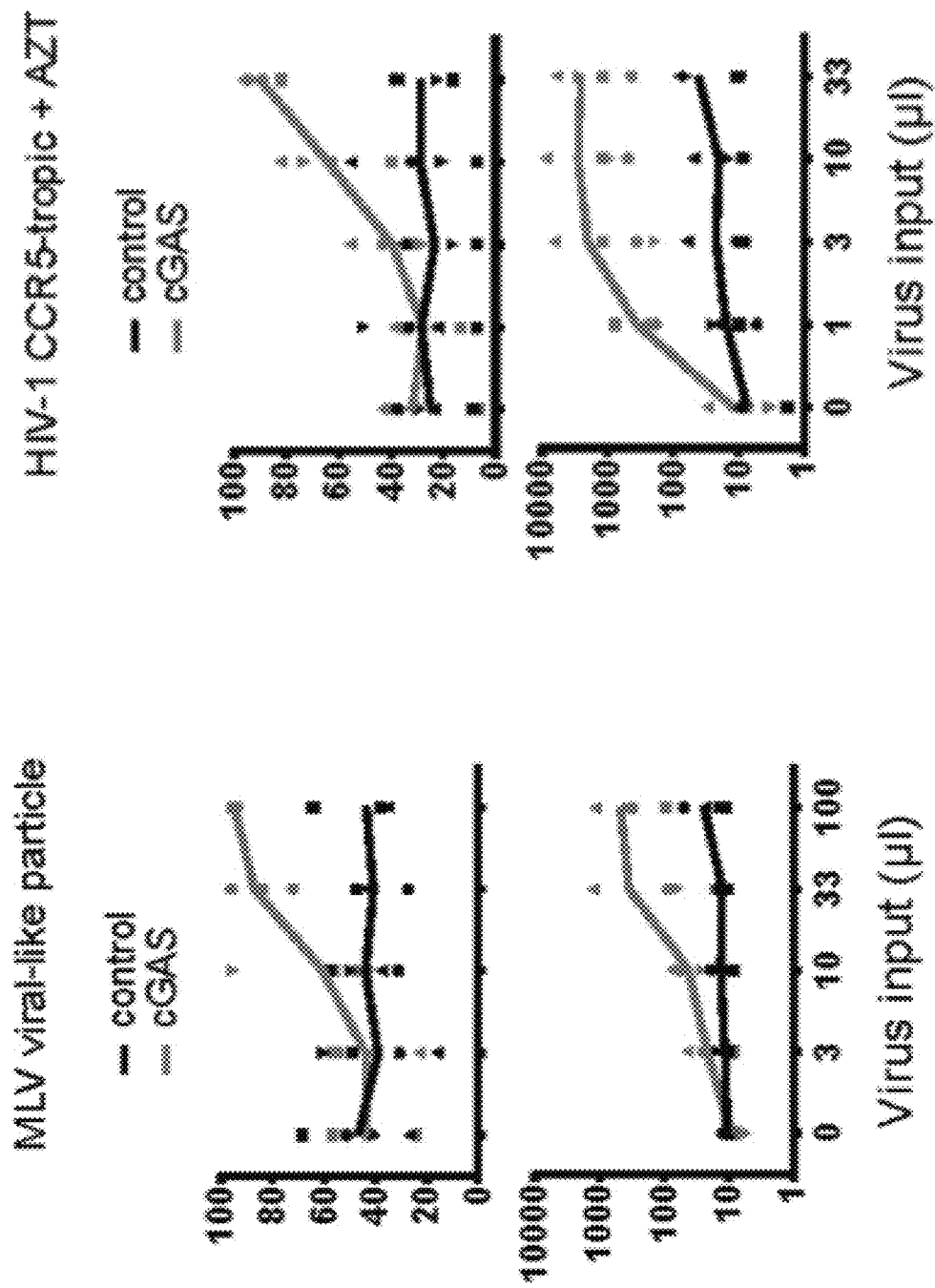
Figure 11E:
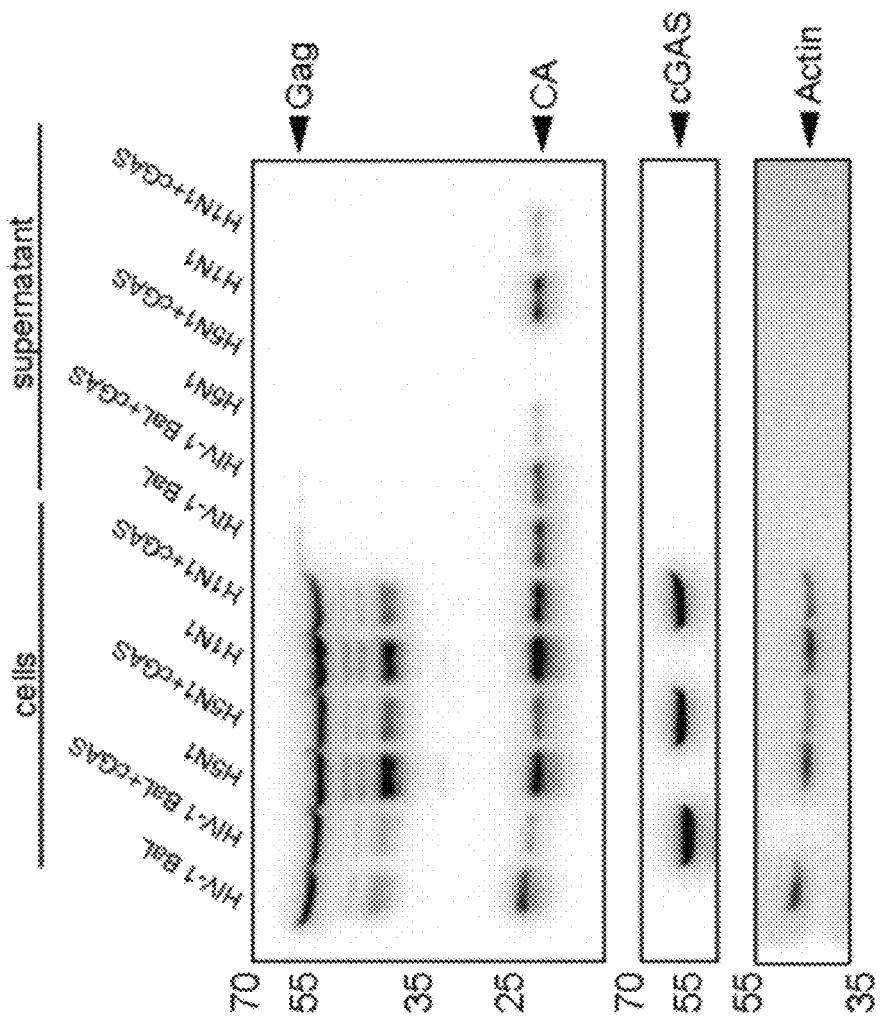
Figure 11D:
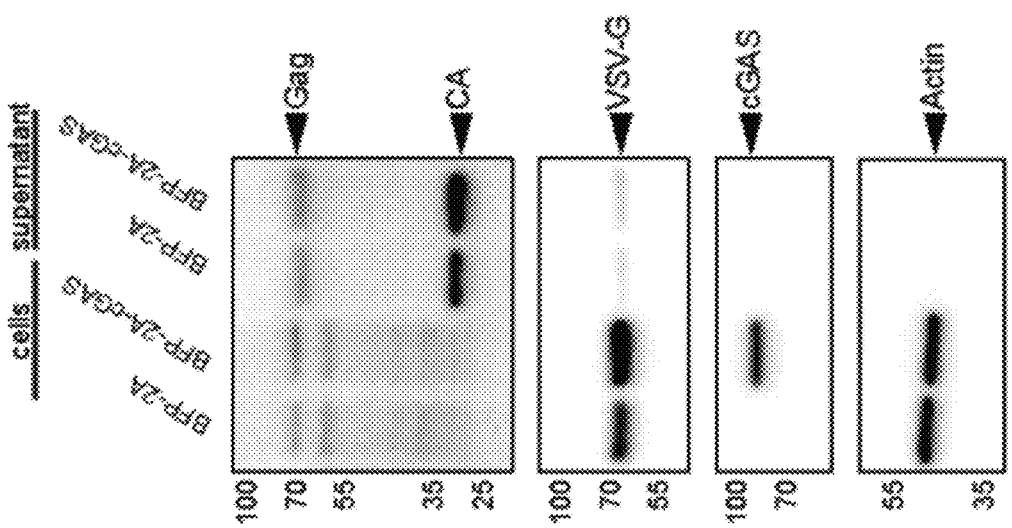

Expression of VSV-G by cells leads to production of tubulovesicular structures. To exclude that transmission of cGAMP was a specificity of VSV-G, the inventors produced VLPs carrying the Influenza envelope proteins H1N1 and H5N1 instead of VSV-G. Such particles, which were produced in the presence of cGAS, activated monocytes in all cases (FIG. 10D, FIG. 11A, FIG. 11E). The inventors next considered whether cGAMP packaging and transfer to target cells was specific to HIV-1 particles. They produced VLPs from another retrovirus, the gammaretrovirus MLV, and found that they could also transmit cGAMP (FIG. 10E, FIG. 11B, FIG. 11D). Finally, they examined whether HIV-1 particles expressing the wild-type CCR5-tropic envelope protein BaL could transfer cGAMP. Indeed, they found that HIV-1 particles produced with cGAS could transmit cGAMP and activate in an innate immune response in target cells (FIG. 10F, FIG. 11C, FIG. 11E). Thus, cGAMP packaging and transfer to target cells is a general property of retroviral particles from different origins.

Collectively, the present results provide evidence that cGAMP can be transferred between cells by virtue of packaging within viral particles or fusion-competent EVs, defining a new mechanism of innate immune signal transmission (FIG. 12). Spreading of innate responses is generally attributed to the production of cytokines, including interferons. The ensuing innate signals induce the production of effector molecules. Interestingly, some antiviral effectors can be packaged into viral particles and EVs, such as APOBEC3G, but effectors do not directly induce an innate immune response in the target cells. cGAMP has the ability to diffuse between cells that are physically connected by gap junctions. Viral transfer of cGAMP does not require a direct contact between the cells, which may allow transmission of an innate signaling molecule within the organism or during transmission between hosts. This process could maximize the rapid induction of effector responses in target cells. Interestingly, immunostimulatory cyclic dinucleotides that are produced by bacteria can be delivered into the target cell and induce an innate immune signal, providing an appealing parallel with viral-mediated transfer of cGAMP.

The present results additionally indicate that non-viral cell-derived EVs that could be exosomes can also transmit cGAMP to some extent. Consistent with this finding, EVs can transmit cellular RNA between cells. However, transmission of cGAMP is of low efficiency in the absence of a fusogenic viral envelope protein. The inventors speculate that the step of membrane fusion with the target cell membrane is limiting in the case of EVs from non-infected cells. Nevertheless, in addition to its function as a viral sensor, cGAS appears to contribute to setting the tonic level of interferon-induced genes in uninfected mice, which plays a crucial role in determining subsequent susceptibility to infection. Although it is not yet known whether this function of cGAS requires cGAMP synthesis, transmission of cGAMP by host EVs might contribute to set the tonic interferon response.

The inventors demonstrate that the vectorization of cGAMP by VLP of the present invention is far more efficient than 2'3'-cGAMP complexed with lipofectamine (i.e., MLV Gag and HIV Gag VLPs being approximately 1,000 fold more efficient) and than 2'3'-cGAMP in inducing dendritic cell maturation (i.e., MLV Gag and HIV Gag VLPs being approximately 10,000 fold more efficient) (FIG. 14).

The inventors propose that packaging of cGAMP within viral particles can be interpreted as an immune tagging process. This may allow infected cells to further signify progeny viruses as non-self, or dangerous, in order to alert subsequent target cells. It is tempting to speculate that other signaling molecules are also packaged and disseminated by viral particles.

Finally, cGAMP packaging by expressing its synthesizing enzyme in cells producing viral particles provides an attractive strategy to vectorize immunogenic cyclic dinucleotides for therapeutics and vaccines.

Materials and Methods

Cells

293FT and HL-116 cells were cultured as previously described (Lahaye et al., 2013, Immunity, 39, 1132-1142). Monocytes were isolated from peripheral adult human blood as previously described (Lahaye et al., supra). Monocytes were cultured and differentiated into dendritic cells in RPMI medium with GlutaMAX, 10% FBS (Biowest or GIBCO), Penicillin-Streptomycin (GIBCO), Gentamicin (50 mg/ml, GIBCO), and HEPES (GIBCO) in the presence of recombinant human GM-CSF (Miltenyi) at 10 ng/ml and IL-4 (Miltenyi) at 50 ng/ml. THP-1 were cultured in RPMI medium with GlutaMAX, 10% FBS (GIBCO), and Penicillin-Streptomycin (GIBCO).

Constructs

Human cGAS WT open reading frame was amplified by PCR from cDNA prepared from monocyte-derived dendritic cells. Murine cGAS WT open reading frame was amplified by PCR from cDNA prepared from C57BL6 murine bone-marrow derived dendritic cells. Human cGAS E225A/D227A mutant was obtained by overlapping PCR mutagenesis. ntcGAS was obtained by overlapping PCR mutagenesis in order to generate a cGAS variant that is non-targetable by the shRNAs previously described (Lahaye et al., supra). mTagBFP2 (Subach et al., 2011, PLoS One, 6, e28674) sequence was generated synthetically (Invitrogen). The plasmids pSIV3+, psPAX2, pCMV-VSV-G and pTRIP-CMV were previously described (Satoh et al., 2013, *Methods Mol Biol*, 960, 401-409). BFP-2A, BFP-2A-FLAG-ntcGAS, BFP2AFLAG-cGAS E225A/D227A, Puro-2A were cloned in pTRIP-CMV. Non-lentiviral vectors were based on the mammalian expression plasmid pcDNA3.1-Hygro(+) (Invitrogen). Mouse WT, human WT cGAS, human cGAS E225A/D227A, PSTCD-cGAS and PSTCD-cGAS ADBD were cloned in pcDNA3.1-Hygro(+) by PCR. *Propionibacterium shermanii* transcarboxylase domain (PSTCD) is a streptavidin-binding protein (Fukata et al., 2013, *J Cell Biol*, 202, 145-161). PSTCD-cGAS ΔDBD was generated by deleting amino acid regions K173-1220 and H390-C405 by overlapping PCR. The human isoform of cGAS was used in all experiments except noted otherwise. Human STING open reading frame was cloned by PCR from the IMAGE clone 5762441. This clone encodes a histidine residue at position 232, which was mutated into an arginine residue by overlapping PCR mutagenesis (Diner et al., 2013, *Cell Reports*, 3, 355-1361). STING R232 was cloned in pMSCVhygro (Addgene) by PCR. In all final constructs, the entire DNA fragments originating from the PCR and encompassing the restriction sites used for cloning were fully verified by sequencing. IFNβ-pGL3 plasmid was obtained from the lab of Olivier Schwartz, Pasteur Institute. The Influenza envelope plasmids encoding for H1, H5 and N1 were obtained from the lab of Adolfo Garcia-Sastre, Mount Sinai Medical Center. MLV Gag/Pol was expressed from pCL-10A1 (Naviaux et al., 1996, *J Virol*, 70, 5701-5705). Replication competent CCR5-tropic R5GFP construct was NL4-3/BaL env, Δnef, enconding GFP in nef, previously described (Lahaye et al., supra).

Viruses

Viral particles were produced as previously described from 293FT cells (Lahaye et al., supra). Lentiviral particles and virus-like particles were produced by transfecting 1 µg of psPAX2 and 0.4 µg of pCMV-VSV-G together with 1.6 µg of a mammalian expression plasmid or lentiviral vector plasmid per well of 6-well plate.

For CCR5 tropic NL4-3/BaL env virus 1.6 µg of pcDNA3.1-Hygro(+)-ms cGAS plasmid was co-transfected with 1.4 µg of R5GFP plasmid. For Influenza psuedotyped VLPs 1 µg of pcDNA3.1-Hygro(+)-ms cGAS plasmid was co-transfected with 1 µg of psPAX2 and 0.5 µg of either H1 or H5 and 0.5 µg of N1 encoding plasmids. For MLV viral particles 1.6 µg of pTRIP-CMV-BFP-2A or pTRIP-CMV-BFP2A-FLAG-ntcGAS were mixed with 1 µg of pCL-10A1 and 0.4 µg of pCMV-VSV-G. When psPAX2 and/or pCMV-VSV-G were omitted the same amount of DNA was substituted by pcDNA3.1-Hygro(+). Virus-containing cell supernatants were systematically filtrated over 0.45 µM filters.

For cGAMP OVA VLPs and cGAMP VLPs used in FIG. 14, the viral particles were concentrated and purified as follows. 34 ml of crude supernatant coming from 293FT were loaded in Ultra-Clear Centrifuge tubes (Beckman Coulter) on top of 6 ml of a sucrose (Sigma) cushion (20% dissolved in PBS) and ultracentrifuged at 100,000 g in an SW32 rotor (Beckman Coulter). The recovered viral pellet was resuspended in 13 ml of PBS and transferred in new Ultra-Clear Centrifuge tubes and ultracentrifuged at 100,000 g in an SW41 rotor (Beckman Coulter). The recovered pellet was then resuspended in 750 µl of PBS for cGAMP OVA VLPs or in 1350 µl of PBS for cGAMP VLPs. Three aliquots of 50 µl of each prep were transferred into a separate tube for cGAMP extraction, monocytes infection and p24/p27 ELISA, respectively. All the aliquots were then frozen at −80° C. until further use.

Infections 50,000 freshly isolated monocytes or day 4 differentiated DCs were seeded in 96-well U bottom plates and infected in a final volume of 200 µl with Protamine (Sigma) at 81 g/ml in presence of human recombinant GM-CSF (Miltenyi) at 10 ng/ml and IL-4 (Miltenyi) at 50 ng/ml. Infections with Influenza envelope pseudotyped VLPs and HIV1 NL4-3/BaL env viruses were performed with an additional spin-oculation step at 1200 g, 25° C. for 2 hours. When indicated, Vpx was delivered by adding 50 µl of SlVmac VLPs produced as previously described (Lahaye et al., supra). AZT (Sigma) was added at 25 µM. For the Luciferase assay, VLPs produced in presence or absence of pcDNA3.1-Hygro(+)-ms cGAS were used to infect 293FT in a final volume of 2.5 ml with Protamine at 81 µg/ml.

Western Blotting

293FT cells were detached with PBS and cell pellets were lysed in Sample Buffer (2% SDS, 10% glycerol, 0.05M Tris-HCl pH 6.8, 0.025% bromophenol blue, 0.05M DTT). Virus supernatants were filtered at 0.45 µm and centrifuged at 16,000 g for 2 hours at 4° C. Unless noted otherwise, virus pellets were lysed in 65 µl of sample buffer. Cellular and viral protein lysates were resolved on 4%-20% SDS-PAGE gels (Bio-Rad) and transferred on nitrocellulose membrane (Bio-Rad). Proteins were blotted with antibodies as follows: mouse monoclonal anti-Gag (clone 183-H12-5C-produced in-house), mouse monoclonal anti-VSV tag (clone P5D4—produced in-house), rabbit polyclonal anti-MB21D1 (Sigma), mouse monoclonal anti-Actin (clone C4—Millipore), supernatant from R187 hybridoma for MLV Gag (Chesebro et al., 1983, *Virology*, 127, 134-148) (provided by Marc Sitbon and Jean-Luc Battini), mouse monoclonal anti-CD9 (clone MM2/57—Millipore), mouse monoclonal anti-CD81 (clone B-11—Santa Cruz Biotechnology), mouse monoclonal anti-CD63 (clone H5C6—BD Bioscience), rabbit polyclonal anti-Syntenin-1 (kindly provided by Pascale Zimmerman) (Zimmermann et al., 2001, *Molecular Biology of the Cell*, 12, 339-350) and Streptavidin-HRP (Pierce) in the case of PSTCD-cGAS proteins. ECL signal was recorded on the ChemiDoc XRS Imager (Bio-Rad). Data was analyzed with Image Lab (Bio-Rad).

Luciferase Assay

293FT cells were plated in a 24-well plate. The next day, cells were transfected with 300 ng of total DNA comprising IFNβ-pGL3 and the empty vector pTRIP-CMV-Puro-2A or pMSCVhygro-STING R232 with TransIT-293 (Mirus). The next day, medium was removed and replaced with 2.5 ml of crude supernatant coming from 293FT-producer cells. 3'3' cGAMP (InvivoGen) was delivered with Lipofectamine 2000 (Invitrogen) transfection (1 µg 3'3'cGAMP:1 Lipofectamine 2000) in a final volume of 500 µl. After 24 hours cells were washed with PBS and lysed with Passive Lysis Buffer (Promega) and 10 µl of the lysate were used to perform the Luciferase assay. Luciferase activity was measured using Luciferase Assay Reagent (Promega). Luminescence was acquired on a FLUOstar OPTIMA microplate reader (BMG labtech).

cGAMP Extraction and Bioassay

The assay was adapted from previously described protocols (Woodward et al., 2010, *Science*, 328, 1703-1705; Ablasser et al., 2013, *Nature*, 497, 380-384; Wu et al., 2012, *Science*, 339, 826-830). 293FT cells and supernatants were recovered as described for Western blotting. After centrifugation, cells and viral pellets were lysed in lysis buffer (1 mM NaCl, 3 mM $MgCl_2$, 1 mM EDTA, 10 mM Tris-HCl pH7.4, 1% Triton X-100) for 20 minutes at 4° C. The cells and viral lysates were centrifuged at 1000 g for 10 min and the supernatant was treated with 50U/ml of Benzonase (Sigma) for 45 minutes at 4° C. The suspension was then extracted using Phenol:Chloroform:Isoamyl alcohol (25:24:

1, v/v—Sigma) for two rounds, and the recovered aqueous phase was then washed with Chloroform (VWR Chemicals). The remaining aqueous phase was loaded on an Amicon 3KDa cutoff column (Millipore) and centrifuged at 14000 g for 30 minutes. The eluted solution was then subjected to speed vacuum in Savant DNA Speed Vac DNA 110 at 43° C. for 2 hours. For cGAMP OVA VLPs and cGAMP VLPs used in FIG. 14, to a 50 µl aliquot 50 µl of DNAse/RNAse Free Water (GIBCO) were added; the obtained 100 µl were then lysed with 400 µl of methanol (VWR Chemicals) in order to obtain an 80/20 (v/v) mix of MeOH/$H_2O$. The lysates were subjected to 5 cycles of freezing and thawing, and centrifuged at 16,000 g at 4° C. for 20 min. The recovered supernatants were then subjected to speed vacuum in Savant DNA Speed Vac DNA 110 at 43° C. for 2.5 hours or at 65° C. for 2.5 hours. As an internal control for the extraction process, known quantities of 2'3'-cGAMP were spiked in an 80/20 (v/v) mix of MeOH/$H_2O$ and extracted as the viral preps, omitting the freeze and thaw steps. The pellets were resuspended in 25 µl (Phenol:Chloroform:Isoamyl alcohol extraction) or 30 µl (methanol/water extraction) of RNAse-DNAse free water (GIBCO) and used on THP-1. 24 hours prior to the assay, 100,000 THP-1 cells were re-suspended in fresh medium with PMA (Sigma) at 30 ng/ml and seeded in 96-well plate flat bottom. PMA was then washed and THP-1 cells were treated with the resuspended samples during permeabilization with a buffer containing 50 mM HEPES (GIBCO), 100 mM KCl, 3 mM $MgCl_2$, 0.1 mM DTT, 85 mM sucrose (Sigma), 1 mM ATP (Sigma), 1 mM GTP (Sigma), 0.2% BSA (Euromedex), and 0.001% Digitonin (Calbiochem) for 30 minutes at 37° C., 5% $CO_2$ atmosphere. At the same time permeabilized THP-1 cells were treated with synthetic 2'3' cGAMP (InvivoGen). The buffer was then washed and fresh medium was added on the cells and incubated overnight. For samples extracted with MeOH/$H_2O$, 50U/ml of benzonase were added during the initial stimulation phase. The supernatant was then transferred on HL-116 cells to measure interferon activity as described (Lahaye et al., supra).

Filtration

293FT cells were transfected with 1.6 µg of pTRIP-CMV-BFP-2A-FLAG-ntcGAS, 1 µg of psPAX2 and 0.4 µg of pCMV-VSV-G and treated as previously described for virus production. The supernatant was then recovered and centrifuged on an Amicon 10KDa cutoff tube (Millipore) for 30 minutes at 4,000 g at 4° C. The retentate was resuspended in previously described DC media. The resuspended retentate and the filtrated fraction were then used to treat monocytes as previously described.

Fractionation

RPMI with GlutaMAX medium containing 10% FBS and Penicillin-Streptomycin was depleted from bovine EVs by an overnight centrifugation at 100000 g and then filtered at 0.22 µm. 293FT were transfected as described for viruses. 12 hours after transfection, medium was replaced with fresh EV-depleted medium. 30 hours later, the supernatant was recovered and filtered at 0.45 m. Vesicles were isolated from conditioned medium by sequential untracentrifugation steps: 20 minutes at 2,000 g (bench-top centrifuge); 25 minutes at 9,000 rpm (ultracentrifuge XL-100K Beckman with SW55Ti rotor, k_factor=1,759.27, 10,000 g fraction); 1 hour at 30,000 rpm (ultracentrifuge XL-100K Beckman with SW55Ti rotor, k_factor=169.44, 100,000 g fraction). Each pellet was suspended in either 50 µl of PBS (Western blotting) or 600 µl of EV depleted media (infection of monocytes). The remaining supernatant of the 100,000 g fraction was used only for infection of monocytes.

Flow Cytometry

Cell surface staining was performed in PBS, 1% BSA (Euromedex), 1 mM EDTA (GIBCO). The antibodies used were anti-human CD86 PE (clone IT2.2—eBioscience), anti-human CD14 FITC (clone 61D3—eBioscience) and anti-human DC SIGN PE (clone 120507—R&D Systems). Cells were stained for 15 minutes at 4° C., washed for two times and fixed in 1% paraformaldehyde (Electron Microscopy Sciences). Data was acquired on a FACSVerse (BD) or an Accuri C6 (BD) and analyzed in FlowJo.

IP-10 Protein Quantification

IP-10 concentration was measured on pure or 10-fold dilutions (100,000 g fraction, Influenza pseudotyped viral particles, NL4-3/BaL env virus) of supernatants from treated monocytes. IP-10 concentration was measured with a Human IP-10 cytometric assay (BD) according to the manufacturer's protocol. Data was acquired on a BD FACSVerse (BD) and analyzed in FCAP Array (BD).

Statistics

Statistical analyses were performed in Prism (GraphPad).

Mass Spectrometry

Extracts obtained after cGAMP extraction procedure were diluted (1/1000, 1/100 or 1/10) in solution A (2% (v/v) acetonitrile/water, 0.1% (v/v) formic acid) and analyzed (1 µL) using an actively split capillary HPLC system (Ultimate 3000, Dionex, Germering, Germany) connected to a QSTAR Elite quadrupole time-of-flight (Q-TOF) mass spectrometer (Applied Biosystems/MDS SCIEX). Sample separation was achieved on an analytical C18 column (75 am id×150 mm long, packed with 3 am particles with 100 Å pore size, C18 PepMap™, Dionex S.A.) using a 30 min isocratic elution (5% (v/v) B, 95% (v/v) A, with mobile phase B, 80% (v/v) acetonitrile/water, 0.085% (v/v) formic acid) at 200 nL/min. Data acquisition was performed using the Analyst QS Software (2.0), set for the positive-ion mode with an electrospray (ESI) voltage of 2.2 kV. TOF-MS survey scan was acquired for 1 s over a mass range of 300-800 m/z. Then a product acquisition method was used to acquire product ion scans of ion m/z 675.1 at 40 eV collision energy (CE) per cycle of 2 s over a mass range of 50-680 m/z and three product ion scans in pseudo selected reaction monitoring (pseudo-SRM) mode of ion m/z 675.1 at 30 eV CE per cycle of 1 s over mass range 520-530 m/z, at 60 eV CE per cycle of 1 s over mass range 120-170 m/z and at 40 eV CE per cycle of 1 s over mass range 460-490 m/z.

Example 3

Results

The inventors sought to determine whether transfer of cGAMP by viral particles would occur at physiologically relevant levels of cGAS expression. HeLa cells express the cGAS protein. HeLa cells did not contain detectable amounts of intracellular cGAMP at steady-state, but it was detected after DNA stimulation. Disruption of the cGAS gene by CRISPR/Cas9 in HeLa abolished cGAMP production after DNA stimulation. Next, the inventors harvested the pelletable extracellular material of control HeLa, DNA-stimulated HeLa or HeLa transfected with VLP-coding plasmids (which also provide a DNA stimulus). cGAMP was detected in the material of all DNA-stimulated HeLa, consistent with it being packaged in extracellular vesicles (EVs) and viral particles (FIG. 13A). However, only HeLa-derived VLPs induced IP-10 production in PMA-treated THP-1 cells, and not EVs from control HeLa or DNA-stimulated HeLa (FIG. 13B). To ascertain that cGAMP was transferred, the inventors tested the material in the STING Luciferase reporter assay. HeLa-derived VLPs, but not EVs from DNA-stimulated HeLa, activated the interferon promoter in a STING-dependent manner (FIG. 13C). Overall, these data demonstrate that viral particles and EVs package cGAMP produced by endogenous cGAS, but only viral material can efficiently transfer the second messenger cGAMP.

Methods

HeLa Transfection 0.8 million HeLa cells per well were seeded in a 6 well plate and transfected the same day. Transfection was performed with 7.5 µl of Lipofectamine 2000 (Invitrogen) and 4 µg of DNA total. In the case of Empty Vector transfections, 4 µg of pcDNA3.1-Hygro(+) were delivered. In the case of VLPs, 3.5 µg of psPAX2 and 0.5 µg of pCMV-VSV-G were transfected. In the case of HIVGFP, 3.5 µg of HIVGFP env-nef- and 0.5 µg of pCMV-VSV-G were transfected. The medium was changed after 14-16 hours. The supernatant was then harvested after 28-30 hours and systematically filtered at 0.45 µm. For cGAMP extraction and THP-1 stimulation the supernatant was first centrifuged at 2000 g for 20 minutes at 4° C., and then 30 ml were loaded in Ultra-Clear Centrifuge tubes (Beckman Coulter) and ultra-centrifuged at 100000 g in an SW32 rotor (Beckman Coulter). For the IFN-βLuciferase reporter assay the 2000 g centrifugation was skipped. The obtained ultracentrifuged pellets were resuspended in RPMI 10% FBS (GIBCO), PenStrep to treat THP-1, in DMEM 10% FBS (GIBCO), PenStrep for the IFN-β Luciferase reporter assay, and in 500 µl of lysis buffer (1 mM NaCl, 3 mM $MgCl_2$, 1 mM EDTA, 10 mM Tris-HCl pH7.4, 1% Triton X-100) for cGAMP extraction. Cells were recovered by trypsinization, pelleted, washed with PBS, resuspended in lysis buffer for cGAMP extraction and then frozen at −80° C.

THP-1 Stimulation 100,000 THP-1 cells were seeded the day prior to stimulation in a 96 well plate flat bottom in fresh medium containing PMA (SIGMA) at 30 ng/ml. Before stimulation the medium was replaced with fresh medium and the cells were then treated with the re-suspended ultracentrifuged material in presence of 81a/ml of Protamine (SIGMA). 48 hours after stimulation the supernatant was collected and stored at 4° C. until IP-10 quantification.

IP-10 Protein Quantification

IP-10 concentration was measured on pure or 10-fold dilutions of supernatants from treated THP-1. IP-10 concentration was measured with a Human IP-10 cytometric assay (BD) according to the manufacturer's protocol. Data was acquired on a BD FACSVerse (BD) and analyzed in FCAP Array (BD).

Luciferase Assay 45,000 293FT cells were plated in a 24-well plate. The next day, cells were transfected with 500 ng of total DNA comprising 200 ng of IFNβ-pGL3 and 300 ng of the empty vector pMSCV-hygro or pMSCV-hygro-STING R232 with TransIT-293 (Mirus). For RIG-I N228 transfections, 150 ng of pCAGGS-FlagRIGIN228 were co-transfected with 150 ng of the empty or STING expressing vector. The next day, medium was removed and replaced with 380 µl of the re-suspended pelleted material in presence of 81 µg/ml of Protamine (SIGMA). In the case of HIVGFP env-nef-(G) pellets, 293FT cells were treated with 251 µM AZT (SIGMA) and 10 µM Nevirapine (SIGMA). 2'3' cGAMP (InvivoGen) was delivered with Lipofectamine 2000 (Invitrogen) transfection (1 µg 2'3' cGAMP:1 µl Lipofectamine 2000) in a final volume of 380 µl. After 24 hours cells were washed with PBS and lysed in Passive Lysis Buffer (Promega). 10 µl of the lysate were used to perform the Luciferase assay. Luciferase activity was measured using Luciferase Assay Reagent (Promega). Luminescence was acquired on a FLUOstar OPTIMA microplate reader (BMG Labtech).

cGAMP Extraction and Bioassay

Cells and supernatants were recovered as described. The lysates were subjected to 5 cycles of freeze thawing. The lysates were then boiled at 95° C., cooled down in ice and centrifuged in a benchtop centrifuge at 16000 g for 20 minutes at 4° C. The supernatant was then recovered and treated with 50U/ml of Benzonase (Sigma) for 45 minutes at 4° C. The suspension was then extracted using Phenol:Chloroform:Isoamyl alcohol (25:24:1, v/v—Sigma) for two rounds, and the recovered aqueous phase was then washed with Chloroform (VWR Chemicals). The remaining aqueous phase was loaded on an Amicon 3KDa cutoff column (Millipore) and centrifuged at 14000 g for 30 minutes. The eluted solution was then subjected to speed vacuum in Savant DNA Speed Vac DNA 110 at 65° C. for 2 hours. The pellet was resuspended in RNAse-DNAse free water (GIBCO) and used on THP-1. 24 hours prior to the assay, 100,000 THP-1 cells were re-suspended in fresh medium with PMA (Sigma) at 30 ng/ml and seeded in 96-well plate flat bottom. PMA was then washed and THP-1 cells were treated with the resuspended samples during permeabilization with a buffer containing 50 mM HEPES (GIBCO), 100 mM KCl, 3 mM $MgCl_2$, 0.1 mM DTT, 85 mM sucrose (Sigma), 1 mM ATP (Sigma), 1 mM GTP (Sigma), 0.2% BSA (Euromedex), and 0.001% Digitonin (Calbiochem) for 30 minutes at 37° C., 5% $CO_2$ atmosphere. At the same time permeabilized THP-1 cells were treated with synthetic 2'3' cGAMP (InvivoGen). The buffer was then washed and fresh medium was added on the cells and incubated overnight. The supernatant was then transferred on HL-116 cells to measure interferon activity as described.

Quantitative Bioassay for IFNs

Supernatants from THP-1 stimulated cells were assayed for IFN activity with the HL116 cell line, which carries a luciferase reporter controlled by the IFN-inducible 6-16 promoter, as previously described (Uze' et al., 1994). In brief, the reporter cells were exposed to cell culture supernatants for 5 hr and assayed for luciferase activities (Promega), which were then translated to IFN activities by using a standard curve generated from a serial dilution of human IFNalpha-2a (ImmunoTools).

Example 4

Results

Figures 15A, 15B:
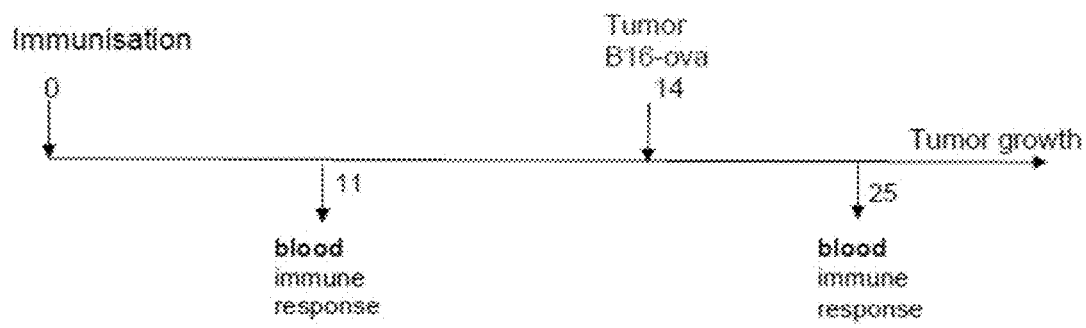
Figure 15C:
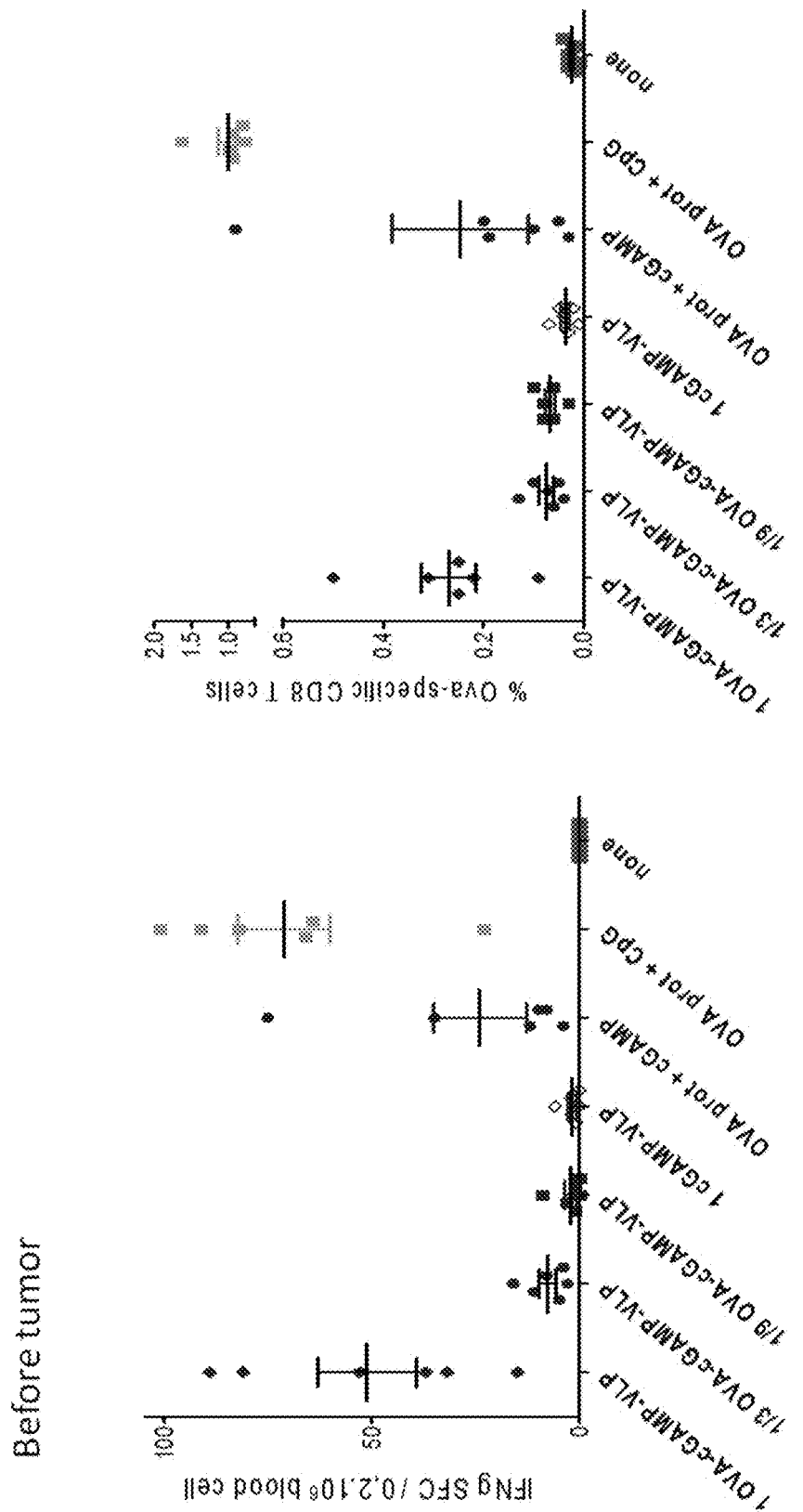
Figure 15D:
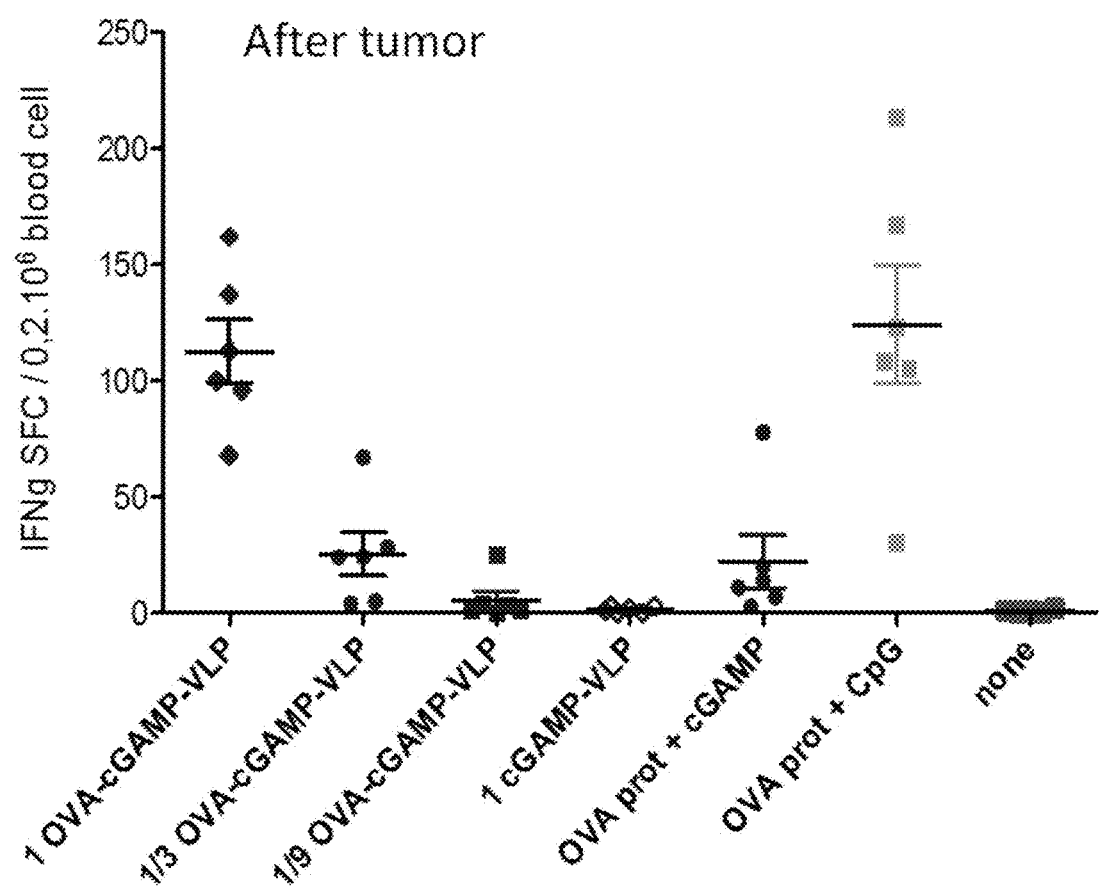
Figure 15E:
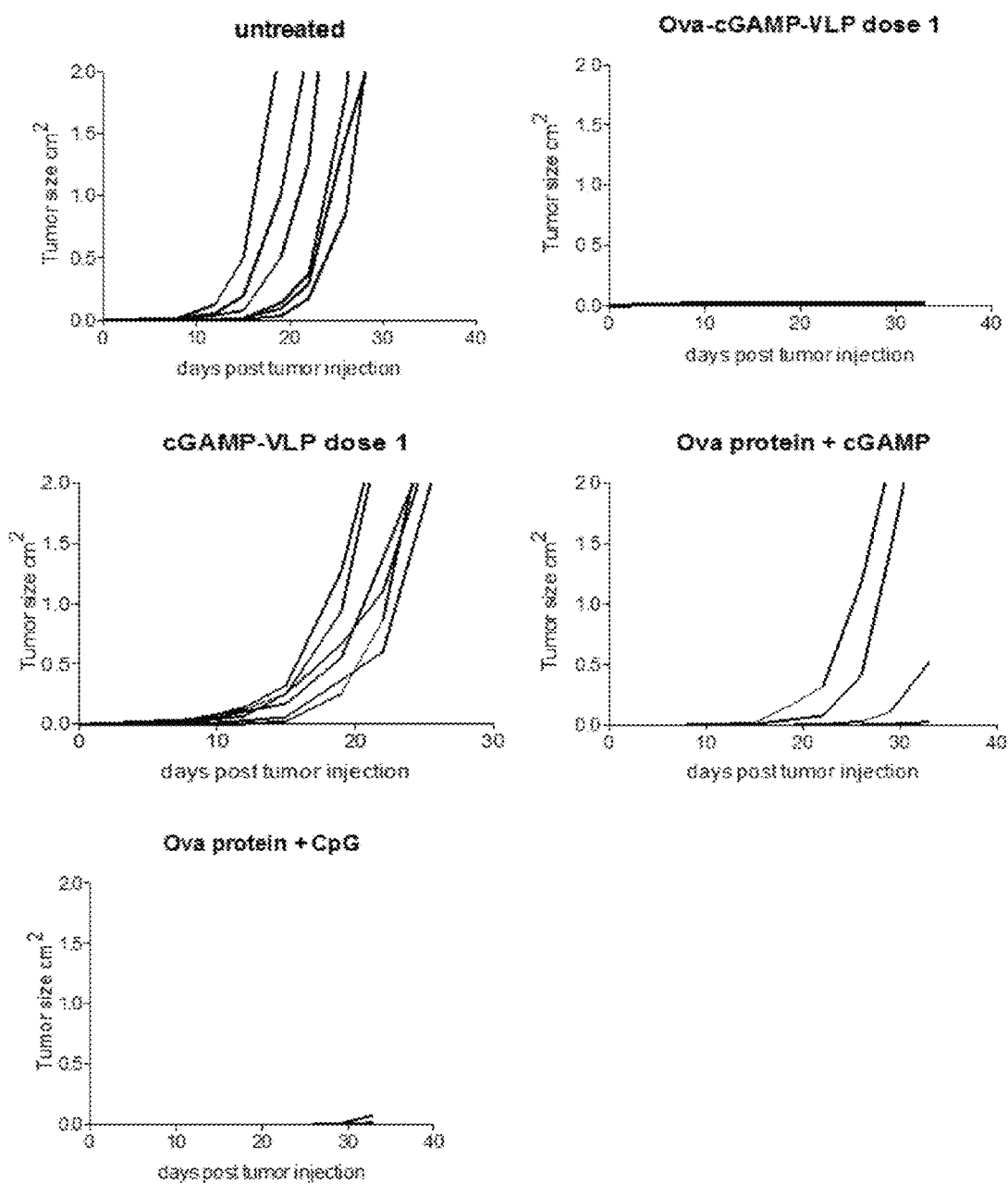

To test the activity of cGAMP-VLPs to control tumor growth in a prophylactic vaccination setting, the inventors treated mice with Ova-cGAMP-VLPs, control cGAMP-VLPs, Ova protein+cGAMP or Ova protein+CpG (FIGS. 15A, B). Day 11 post-immunization, Ova-specific CD8+ T cells were detected with Ova-cGAMP-VLPs but not with control VLPs (FIG. 15C). An Ova-expressing tumor was grafted at day 14. On Day 25, the presence of the Ova-specific CD8+ T cell response was confirmed and increased (FIG. 15D). In untreated mice and mice vaccinated with control cGAMP-VLPs or Ova protein+cGAMP, tumor growth was observed (FIG. 15E). In contrast, Ova-cGAMP-VLP and Ova protein+CpG treated mice were completely protected from tumor growth. Thus, this establishes that Ova-cGAMP-VLPs are functional in vivo as a prophylactic vaccine to induce CD8+ T cell responses and prevent tumor growth.

Figures 15F, 15G:
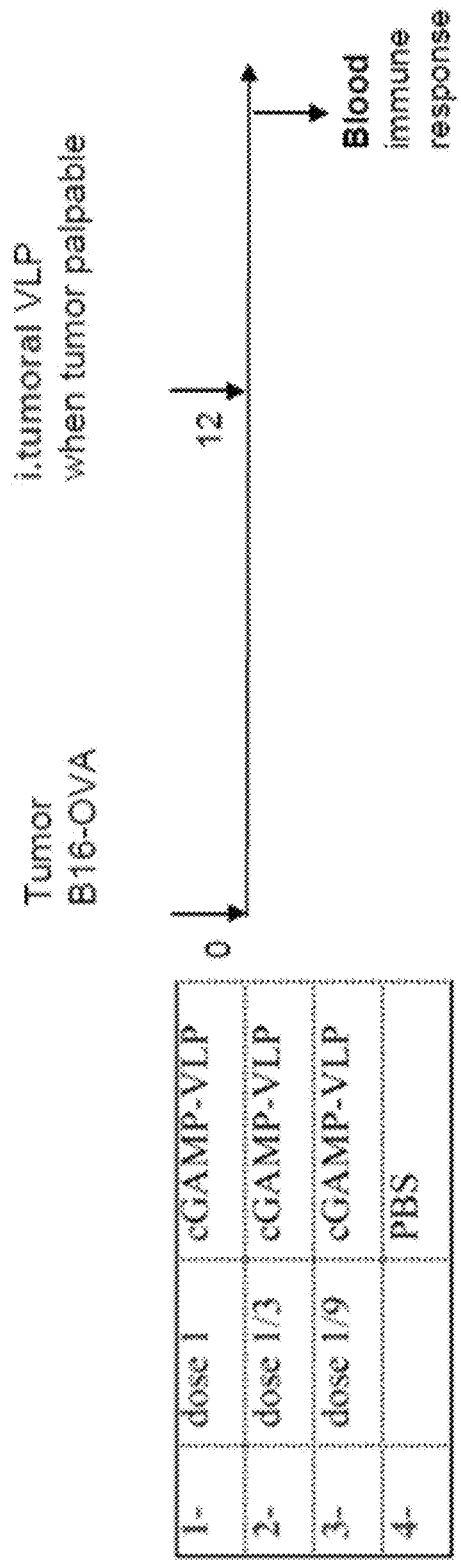
Figure 15H:
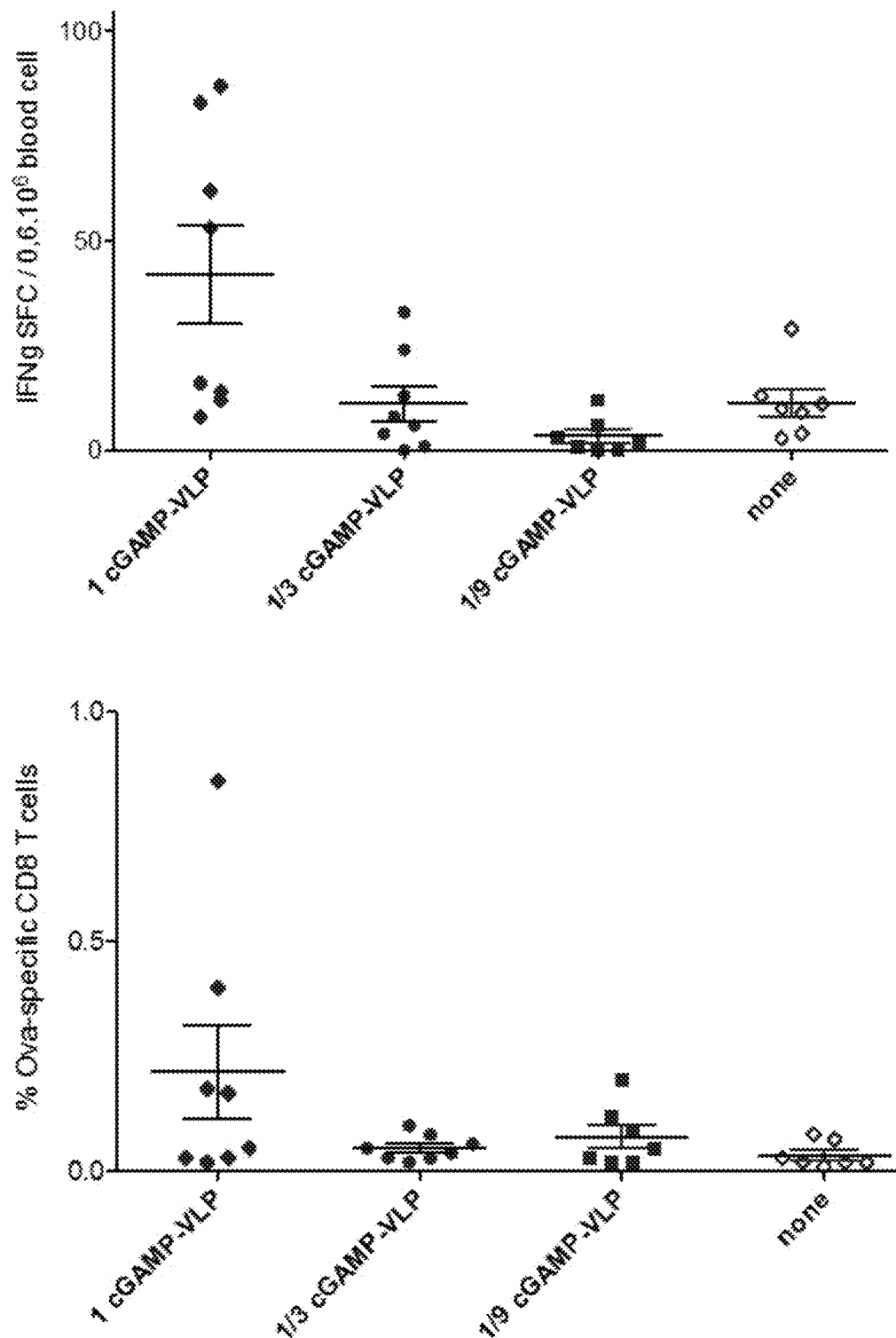

Next, to test the activity of cGAMPs as a therapeutic immunomodulator in the absence of tumor antigens, the inventors grafted an Ova-expressing tumor in mice and at day 12 treated intratumorally with cGAMP-VLPs or control (FIGS. 15F, 15G). In cGAMP-VLPs treated mice, an Ova-specific CD8+ T cell response was detected, but not in control treated mice (FIG. 15H). This establishes that cGAMP-VLPs can provide a therapeutic immunomodulatory signal to induce a tumor-specific CD8+ T cell response.

Methods

Mice and Vaccination

5/6-week-old female C57BL/6J mice were purchased from Charles River France. The care and use of animals used here was strictly applying European and National Regulation for the Protection of Vertebrate Animals used for Experimental and other Scientific Purposes in force (facility license #C75-05-18). It complies also with internationally established principles of replacement, reduction and refinement in accordance with Guide for the Care and Use of Laboratory Animals (NRC 2011). Mice were injected either subcutaneously (s.c.) in the footpads or intratumorally (i.t.).

Quantification of CD8+ T Cell Responses 10 days after injection of VLPs, blood samples were collected by retro-orbital puncture and CD8+ Ova-specific T cell responses were measured using tetramer analysis and quantification of IFN-g producing cells by ELISPOT. Total blood cells were stained with PE-conjugated H-2Kb/SIINFEKL tetramer (Beckman Coulter), anti-CD8 and anti-TCR antibodies (BD Biosciences), followed by red blood cell lysis to quantify OVA-specific $CD8^+$ T cells. Cells were analyzed using a standard LSR-II flow cytometer (BD Biosciences) and the FACS data were analyzed using FlowJo software. The tetramer$^+$ cells were gated on $TCR^+$ $CD8^+$ cells. At the same time, IFNγ-producing OVA-specific $CD4^+$ or $CD8^+$ T cells were measured by ELISPOT on PBMC after red blood cell lysis. Briefly, microplates (Multiscreen HTS IP, Millipore) were coated with anti-murine IFNγ antibody (Diaclone). PBMC ($0.2\times10^6$/well) were cultured overnight in the presence of either control medium or the 257-264 (SIINFEKL) class I-restricted OVA peptide (10 μM) (Polypeptide Group, Strasbourg, France) in complete medium (RPMI-GlutaMAX, 10% fetal calf serum, antibiotics, R-mercaptoethanol). The detection was performed with a biotinylated anti-IFNγ (matched pairs, Diaclone) followed by streptavidin-alkaline phosphatase (Mabtech) and revealed using the appropriate substrate (Bio-Rad). Spots were counted using an ELISPOT Reader System ELR02 (AID, Germany) and results were expressed as the number of cytokine-producing cells per $0.2\times10^6$ PBMC.

Quantification of OVA-Specific Antibody Responses 12 days after immunization, sera were collected by retro-orbital puncture and OVA-specific immunoglobulins were measured by standard ELISA. Briefly, Maxisorp 96-well plates were coated at 4° C. with OVA (10 μg/ml) in carbonate/bicarbonate buffer. After blocking with PBS-5% milk for 2 h, serially diluted sera were added for 2 h at room temperature. After extensive washing, alkaline phosphatase-conjugated anti-mouse IgG, IgG1 or IgG2b (Jackson ImmunoResearch) was added to each well and plates were incubated 1 h at room temperature. After extensive washing, alkaline phosphatase activity was measured adding the CDP-Star® Ready-to-Use substrate (Applied Biosystems). The microplates were read using a Centro LB 960 luminometer (Berthold) and sample sera were compared to a positive standard curve to express the results in arbitrary units (AU).

In Vivo Tumor Assays $0.5\times10^6$ B16F10-OVA cells were administered subcutaneously into the shaved flank of the mice. Tumor growth was measured twice a week using a caliper to determine the tumor size, calculated as (length×width$^2$)/2). Mice were sacrificed when tumor reached 2 cm$^3$.

For tumor prevention experiments, mice were injected with VLPs (Ova-cGAMP-VLPs: estimated 11 ng cGAMP and 10 ng MLV p30 per injection) and tumor cells were injected s.c. 14 days later. For tumor therapeutic setting, tumor cells were injected s.c. and when tumors reached 30-100 mm$^3$ mice were injected i.t. with VLPs (cGAMP-VLPs: estimated 33 ng cGAMP and 43 ng HIV p24 per injection).

EMBODIMENTS OF THE INVENTION

Embodiment 1

A virus-like particle comprising a lipoprotein envelope including a viral fusogenic glycoprotein, wherein said virus-like particle contains cyclic dinucleotides packaged into said virus-like particle.

Embodiment 2

The virus-like particle according to embodiment 1, wherein the virus-like particle further comprises a capsid from retroviridae.

Embodiment 3

The virus-like particle according to any one of embodiments 1-2, wherein the viral fusogenic glycoprotein is a glycoprotein from retroviridae (including lentivirus and retrovirus), herpesviridae, poxviridae, hepadnaviridae, flaviviridae, togaviridae, coronaviridae, hepatitis D virus, orthomyxoviridae, paramyxoviridae, filoviridae, rhabdoviridae, bunyaviridae, or orthopoxiviridae (e.g., variola), preferably from orthomyxovirus, retroviruses, or rhabdovirus.

Embodiment 4

The virus-like particle according to any one of embodiments 1-3, wherein the viral fusogenic glycoprotein is a glycoprotein from HIV (Human Immunodeficiency Virus) including HIV-1 and HIV-2, Influenza including Influenza A (e.g., subtypes H5N1 and H1N1) and Influenza B, thogotovirus, or VSV (Vesicular Stomatitis Virus).

Embodiment 5

The virus-like particle according to any one of embodiments 2-4, wherein the retroviral capsid is from retroviridae, preferably lentivirus and retrovirus.

Embodiment 6

The virus-like particle according to any one of embodiments 2-5, wherein the retroviral capsid is from HIV or MLV (Murine Leukemia Virus).

Embodiment 7

The virus-like particle according to any one of embodiments 1-6, wherein the cyclic dinucleotides are selected from the group consisting of cyclic di-adenosine monophosphate (c-di-AMP), cyclic di-guanosine monophosphate (c-di-GMP), and cyclic guanosine monophosphate-adenosine monophosphate (cGAMP).

Embodiment 8

The virus-like particle according to any one of embodiments 1-7, wherein the cyclic dinucleotides are cGAMP (2'-3'-cyclic GMP-AMP).

Embodiment 9

The virus-like particle according to any one of embodiments 1-8, wherein it further comprises an antigen or any other protein or nucleic acid of interest.

Embodiment 10

The virus-like particle according to any one of embodiments 1-9 as a drug.

Embodiment 11

The virus-like particle according to any one of embodiments 1-9 as a vaccine adjuvant.

Embodiment 12

A pharmaceutical, vaccine or veterinary composition comprising a virus-like particle according to any one of embodiments 1-9 and a pharmaceutically acceptable carrier.

Embodiment 13

The pharmaceutical, vaccine or veterinary composition according to embodiment 12, wherein it further comprises an antigen or a therapeutic active agent.

Embodiment 14

A method for inducing or enhancing an immune response in a subject comprising administering a virus-like particle according to any one of embodiments 1-9 or a composition according to embodiment 12 or 13.

Embodiment 15

A method for preventing or treating an infectious disease or a cancer in a subject comprising administering a virus-like particle according to any one of embodiments 1-9 or a composition according to embodiment 12 or 13.

Embodiment 16

An expression vector or a combination of expression vectors, comprising a sequence encoding a cyclic dinucleotide synthase and either a sequence encoding a viral fusogenic glycoprotein or a sequence encoding a retroviridae capsid protein, or both.

Embodiment 17

The expression vector or combination thereof according to embodiment 16, wherein the cyclic dinucleotide synthase is selected from the group consisting of the diadenylate cyclase, diguanylate cyclase and the cyclic GMP-AMP synthase.

Embodiment 18

The expression vector or combination thereof according to embodiment 16 or 17, wherein the cyclic dinucleotide synthase is cGAS (Cyclic GMP-AMP synthase).

Embodiment 19

The expression vector or combination thereof according to any one of embodiments 16-18, wherein the expression vector comprises both a sequence encoding a viral fusogenic glycoprotein and a sequence encoding a retroviridae capsid protein.

Embodiment 20

The expression vector or combination thereof according to any one of embodiments 16-19, wherein the expression vector further comprises a sequence encoding an antigen or any other protein or nucleic acid of interest.

Embodiment 21

The expression vector or combination thereof according to any one of embodiments 16-20, wherein the expression vector is a plasmid, a baculovirus vector or a viral vector.

Embodiment 22

The expression vector or combination thereof according to embodiment 21, wherein the viral vector is selected from the group consisting of adenoviral vector, adeno-associated virus based vector, and lentiviral vector.

Embodiment 23

The expression vector or combination thereof according to any one of embodiments 16-22 as a drug or a vaccine adjuvant.

Embodiment 24

A pharmaceutical, vaccine or veterinary composition comprising an expression vector or combination thereof according to any one of embodiments 16-22 and a pharmaceutically acceptable carrier.

Embodiment 25

A method for inducing or enhancing an immune response in a subject comprising administering an expression vector according to any one of embodiments 16-22 or a composition according to claim 24.

Embodiment 26

A method for preventing or treating an infectious disease or a cancer in a subject comprising administering an expression vector according to any one according to embodiments 16-22 or a composition according to embodiment 24.

Embodiment 27

A recombinant eukaryotic host cell comprising a sequence encoding a cyclic dinucleotide synthase and a sequence encoding a viral fusogenic glycoprotein or a sequence encoding a retroviridae capsid protein or both.

Embodiment 28

The recombinant eukaryotic host cell according to embodiment 27, wherein the cyclic dinucleotide synthase is selected from the group consisting of the diadenylate cyclase, diguanylate cyclase and the cyclic GMP-AMP synthase.

Embodiment 29

The recombinant eukaryotic host cell according to embodiment 27 or 28, wherein the cyclic dinucleotide synthase is cGAS (Cyclic GMP-AMP synthase).

Embodiment 30

The recombinant eukaryotic host cell according to any one of embodiments 27-29, wherein the recombinant eukaryotic host cell comprises both a sequence encoding a viral fusogenic glycoprotein and a sequence encoding a retroviridae capsid protein.

Embodiment 31

The recombinant eukaryotic host cell according to any one of embodiments 27-30, wherein the recombinant eukaryotic host cell further comprises a sequence encoding an antigen or any other protein or nucleic acid of interest.

Embodiment 32

The recombinant eukaryotic host cell according to any one of embodiments 27-31, wherein one or several sequences selected from the sequence encoding the cyclic dinucleotide synthase, the viral fusogenic glycoprotein and the sequence encoding a retroviridae capsid protein are episomal.

Embodiment 33

The recombinant eukaryotic host cell according to any one of embodiments 27-31, wherein one or several sequences selected from the sequence encoding the cyclic dinucleotide synthase, the viral fusogenic glycoprotein and the sequence encoding retroviridae capsid protein are integrated into the host cell chromosome.

Embodiment 34

The recombinant eukaryotic host cell according to any one of embodiments 27-33 as a drug or a vaccine adjuvant.

Embodiment 35

A method for inducing or enhancing an immune response in a subject comprising administering a recombinant eukaryotic host cell according to any one of embodiments 27-33.

Embodiment 36

A method for preventing or treating an infectious disease or a cancer in a subject comprising administering a recombinant eukaryotic host cell according to any one of embodiments 27-33.

Embodiment 37

A method for preparing a virus-like particle comprising cyclic dinucleotides packaged into said virus-like particle, wherein the method comprises:
- co-expression of a cyclic dinucleotide synthase and a viral fusogenic glycoprotein in a eukaryotic cell in conditions allowing the synthesis of cyclic dinucleotides and the viral fusogenic glycoprotein in said cell; and
- recovery of the virus-like particles produced by said cell.

Embodiment 38

The method according to embodiment 37, wherein the cyclic dinucleotide synthase is selected from the group consisting of the diadenylate cyclase, diguanylate cyclase and the cyclic GMP-AMP synthase.

Embodiment 39

The method according to embodiment 37 or 38, wherein the cyclic dinucleotide synthase is cGAS (Cyclic GMP-AMP synthase).

Embodiment 40

The method according to any one of embodiments 37-39, wherein said cell further expresses a capsid from retroviridae.

Embodiment 41

The method according to any one of embodiments 37-40, wherein the viral fusogenic glycoprotein is a glycoprotein from retroviridae (including lentivirus and retrovirus), herpesviridae, poxviridae, hepadnaviridae, flaviviridae, togaviridae, coronaviridae, hepatitis D virus, orthomyxoviridae, paramyxoviridae, rhabdoviridae, bunyaviridae, filoviridae, and orthopoxiviridae (e.g., variola), preferably from orthomyxovirus, retroviruses, and rhabdovirus.

Embodiment 42

The method according to any one of embodiments 37-41, wherein the viral fusogenic glycoprotein is a glycoprotein from HIV (Human Immunodeficiency Virus) including HIV-1 and HIV-2, Influenza including Influenza A (e.g., subtypes H5N1 and H1N1) and Influenza B, and, thogotovirus, and VSV (Vesicular Stomatitis Virus).

Embodiment 43

The method according to any one of embodiments 37-42, wherein the retroviral capsid is from retroviridae, preferably lentivirus and retrovirus, preferably from HIV or MLV (Murine Leukemia Virus).

We claim:

1. A virus-like particle comprising a lipoprotein envelope comprising a viral fusogenic glycoprotein, wherein said virus-like particle contains cyclic guanosine monophosphate-adenosine monophosphate (cGAMP) packaged into said virus-like particle.

2. The virus-like particle according to claim 1, wherein the virus-like particle further comprises a capsid from retroviridae.

3. The virus-like particle according to claim 2, wherein the retroviridae capsid is from a lentivirus or retrovirus.

4. The virus-like particle according to claim 2, wherein the retroviridae capsid is from HIV or Murine Leukemia Virus (MLV).

5. The virus-like particle according to claim 1, wherein the viral fusogenic glycoprotein is a glycoprotein from retroviridae, herpesviridae, poxviridae, hepadnaviridae, flaviviridae, togavoridae, coronaviridae, hepatitis D virus, orthomyxoviridae, paramyxoviridae, filoviridae, rhabdoviridae, bunyaviridae, or orthopoxiviridae.

6. The virus-like particle according to claim 1, wherein the viral fusogenic glycoprotein is a glycoprotein from Human Immunodeficiency Virus (HIV), HIV-1, HIV-2, Influenza virus, Influenza virus type A, Influenza virus type B, Thogotovirus, or Vesicular Stomatitis Virus (VSV).

7. The virus-like particle according to claim 1, wherein the cyclic dinucleotides are 2'-3'-cyclic GMP-AMP.

8. The virus-like particle according to claim 1, wherein the cyclic dinucleotides are 3'-3'-cyclic GMP-AMP.

9. The virus-like particle according to claim 1, further comprising an antigen or a protein or nucleic acid of interest.

10. The virus-like particle according to claim 1 as a drug or a vaccine adjuvant.

11. A pharmaceutical, vaccine or veterinary composition comprising a virus-like particle according to claim 1 and a pharmaceutically acceptable carrier.

12. The pharmaceutical, vaccine or veterinary composition according to claim 11, further comprising an antigen or a therapeutically active agent.

13. A method for inducing or enhancing an immune response in a subject comprising administering a virus-like particle according to claim 1 or a composition according to claim 11.

14. A method for treating an infectious disease or a cancer in a subject comprising administering a virus-like particle according to claim 1 or a composition according to claim 11.

15. A virus-like particle comprising a lipoprotein envelope comprising a viral fusogenic glycoprotein, wherein said virus-like particle contains cGAMP packaged into said virus-like particle wherein the virus-like particle contains at least 0.015 ng/ml of cGAMP.

16. A pharmaceutical, vaccine or veterinary composition comprising a virus-like particle according to claim 15 and a pharmaceutically acceptable carrier.

17. A method for preparing a virus-like particle comprising cyclic dinucleotides packaged into said virus-like particle, wherein the method comprises:

co-expression of a cyclic GMP-AMP synthase (cGAS) and a viral fusogenic glycoprotein in a eukaryotic cell in conditions allowing the synthesis of cGAMP and the viral fusogenic glycoprotein in said cell; and recovering the virus-like particles produced by said cell, wherein the virus-like particles comprise cGAMP packaged into said virus-like particle.

18. The method according to claim 17, wherein said cell further expresses a capsid from retroviridae.

19. The method according to claim 17, wherein the viral fusogenic glycoprotein is a glycoprotein from retroviridae, herpesviridae, poxviridae, hepadnaviridae, flaviviridae, togavoridae, coronaviridae, hepatitis D virus, orthomyxoviridae, paramyxoviridae, rhabdoviridae, bunyaviridae, filoviridae, and orthopoxiviridae.

20. The method according to claim 17, wherein the viral fusogenic glycoprotein is a glycoprotein from HIV, HIV-1 and HIV-2, Influenza virus, Influenza virus type A, Influenza virus type B, Thogotovirus, or VSV.

21. The method according to claim 17, wherein the retroviral capsid is from a retroviridae.

* * * * *

SEQUENCE LISTING

<160> NUMBER OF SEQ ID NOS: 2

<210> SEQ ID NO 1
<211> LENGTH: 522

<212> TYPE: PRT
<213> ORGANISM: Homo sapiens

<400> SEQUENCE: 1

Met Gln Pro Trp His Gly Lys Ala Met Gln Arg Ala Ser Glu Ala Gly
1               5                   10                  15

Ala Thr Ala Pro Lys Ala Ser Ala Arg Asn Ala Arg Gly Ala Pro Met
            20                  25                  30

Asp Pro Thr Glu Ser Pro Ala Ala Pro Glu Ala Ala Leu Pro Lys Ala
        35                  40                  45

Gly Lys Phe Gly Pro Ala Arg Lys Ser Gly Ser Arg Gln Lys Lys Ser
    50                  55                  60

Ala Pro Asp Thr Gln Glu Arg Pro Pro Val Arg Ala Thr Gly Ala Arg
65                  70                  75                  80

Ala Lys Lys Ala Pro Gln Arg Ala Gln Asp Thr Gln Pro Ser Asp Ala
                85                  90                  95

Thr Ser Ala Pro Gly Ala Glu Gly Leu Glu Pro Pro Ala Ala Arg Glu
            100                 105                 110

Pro Ala Leu Ser Arg Ala Gly Ser Cys Arg Gln Arg Gly Ala Arg Cys
        115                 120                 125

Ser Thr Lys Pro Arg Pro Pro Gly Pro Trp Asp Val Pro Ser Pro
    130                 135                 140

Gly Leu Pro Val Ser Ala Pro Ile Leu Val Arg Arg Asp Ala Ala Pro
145                 150                 155                 160

Gly Ala Ser Lys Leu Arg Ala Val Leu Glu Lys Leu Lys Leu Ser Arg
                165                 170                 175

Asp Asp Ile Ser Thr Ala Ala Gly Met Val Lys Gly Val Val Asp His
            180                 185                 190

Leu Leu Leu Arg Leu Lys Cys Asp Ser Ala Phe Arg Gly Val Gly Leu
        195                 200                 205

Leu Asn Thr Gly Ser Tyr Tyr Glu His Val Lys Ile Ser Ala Pro Asn
    210                 215                 220

Glu Phe Asp Val Met Phe Lys Leu Glu Val Pro Arg Ile Gln Leu Glu
225                 230                 235                 240

Glu Tyr Ser Asn Thr Arg Ala Tyr Tyr Phe Val Lys Phe Lys Arg Asn
                245                 250                 255

Pro Lys Glu Asn Pro Leu Ser Gln Phe Leu Glu Gly Glu Ile Leu Ser
            260                 265                 270

Ala Ser Lys Met Leu Ser Lys Phe Arg Lys Ile Ile Lys Glu Glu Ile
        275                 280                 285

Asn Asp Ile Lys Asp Thr Asp Val Ile Met Lys Arg Lys Arg Gly Gly
    290                 295                 300

Ser Pro Ala Val Thr Leu Leu Ile Ser Glu Lys Ile Ser Val Asp Ile
305                 310                 315                 320

Thr Leu Ala Leu Glu Ser Lys Ser Ser Trp Pro Ala Ser Thr Gln Glu
                325                 330                 335

Gly Leu Arg Ile Gln Asn Trp Leu Ser Ala Lys Val Arg Lys Gln Leu
            340                 345                 350

Arg Leu Lys Pro Phe Tyr Leu Val Pro Lys His Ala Lys Glu Gly Asn
        355                 360                 365

Gly Phe Gln Glu Glu Thr Trp Arg Leu Ser Phe Ser His Ile Glu Lys
    370                 375                 380

Glu Ile Leu Asn Asn His Gly Lys Ser Lys Thr Cys Cys Glu Asn Lys
385                 390                 395                 400

```
Glu Glu Lys Cys Cys Arg Lys Asp Cys Leu Lys Leu Met Lys Tyr Leu
                405                 410                 415

Leu Glu Gln Leu Lys Glu Arg Phe Lys Asp Lys Lys His Leu Asp Lys
            420                 425                 430

Phe Ser Ser Tyr His Val Lys Thr Ala Phe His Val Cys Thr Gln
        435                 440                 445

Asn Pro Gln Asp Ser Gln Trp Asp Arg Lys Asp Leu Gly Leu Cys Phe
    450                 455                 460

Asp Asn Cys Val Thr Tyr Phe Leu Gln Cys Leu Arg Thr Glu Lys Leu
465                 470                 475                 480

Glu Asn Tyr Phe Ile Pro Glu Phe Asn Leu Phe Ser Ser Asn Leu Ile
                485                 490                 495

Asp Lys Arg Ser Lys Glu Phe Leu Thr Lys Gln Ile Glu Tyr Glu Arg
            500                 505                 510

Asn Asn Glu Phe Pro Val Phe Asp Glu Phe
        515                 520

<210> SEQ ID NO 2
<211> LENGTH: 507
<212> TYPE: PRT
<213> ORGANISM: Mus musculus

<400> SEQUENCE: 2

Met Glu Asp Pro Arg Arg Arg Thr Thr Ala Pro Arg Ala Lys Lys Pro
1               5                   10                  15

Ser Ala Lys Arg Ala Pro Thr Gln Pro Ser Arg Thr Arg Ala His Ala
            20                  25                  30

Glu Ser Cys Gly Pro Gln Arg Gly Ala Arg Ser Arg Arg Ala Glu Arg
        35                  40                  45

Asp Gly Asp Thr Thr Glu Lys Pro Arg Ala Pro Gly Pro Arg Val His
    50                  55                  60

Pro Ala Arg Ala Thr Glu Leu Thr Lys Asp Ala Gln Pro Ser Ala Met
65                  70                  75                  80

Asp Ala Ala Gly Ala Thr Ala Arg Pro Ala Val Arg Val Pro Gln Gln
                85                  90                  95

Gln Ala Ile Leu Asp Pro Glu Leu Pro Ala Val Arg Glu Pro Gln Pro
            100                 105                 110

Pro Ala Asp Pro Glu Ala Arg Lys Val Val Arg Gly Pro Ser His Arg
        115                 120                 125

Arg Gly Ala Arg Ser Thr Gly Gln Pro Arg Ala Pro Arg Gly Ser Arg
    130                 135                 140

Lys Glu Pro Asp Lys Leu Lys Lys Val Leu Asp Lys Leu Arg Leu Lys
145                 150                 155                 160

Arg Lys Asp Ile Ser Glu Ala Ala Glu Thr Val Asn Lys Val Val Glu
                165                 170                 175

Arg Leu Leu Arg Arg Met Gln Lys Arg Glu Ser Glu Phe Lys Gly Val
            180                 185                 190

Glu Gln Leu Asn Thr Gly Ser Tyr Tyr Glu His Val Lys Ile Ser Ala
        195                 200                 205

Pro Asn Glu Phe Asp Val Met Phe Lys Leu Glu Val Pro Arg Ile Glu
    210                 215                 220

Leu Gln Glu Tyr Tyr Glu Thr Gly Ala Phe Tyr Leu Val Lys Phe Lys
225                 230                 235                 240

Arg Ile Pro Arg Gly Asn Pro Leu Ser His Phe Leu Glu Gly Glu Val
```

-continued

```
                    245                 250                 255
Leu Ser Ala Thr Lys Met Leu Ser Lys Phe Arg Lys Ile Ile Lys Glu
                260                 265                 270

Glu Val Lys Glu Ile Lys Asp Ile Asp Val Ser Val Glu Lys Glu Lys
            275                 280                 285

Pro Gly Ser Pro Ala Val Thr Leu Leu Ile Arg Asn Pro Glu Glu Ile
        290                 295                 300

Ser Val Asp Ile Ile Leu Ala Leu Glu Ser Lys Gly Ser Trp Pro Ile
305                 310                 315                 320

Ser Thr Lys Glu Gly Leu Pro Ile Gln Gly Trp Leu Gly Thr Lys Val
                325                 330                 335

Arg Thr Asn Leu Arg Arg Glu Pro Phe Tyr Leu Val Pro Lys Asn Ala
                340                 345                 350

Lys Asp Gly Asn Ser Phe Gln Gly Glu Thr Trp Arg Leu Ser Phe Ser
            355                 360                 365

His Thr Glu Lys Tyr Ile Leu Asn Asn His Gly Ile Glu Lys Thr Cys
        370                 375                 380

Cys Glu Ser Ser Gly Ala Lys Cys Cys Arg Lys Glu Cys Leu Lys Leu
385                 390                 395                 400

Met Lys Tyr Leu Leu Glu Gln Leu Lys Lys Glu Phe Gln Glu Leu Asp
                405                 410                 415

Ala Phe Cys Ser Tyr His Val Lys Thr Ala Ile Phe His Met Trp Thr
                420                 425                 430

Gln Asp Pro Gln Asp Ser Gln Trp Asp Pro Arg Asn Leu Ser Ser Cys
            435                 440                 445

Phe Asp Lys Leu Leu Ala Phe Phe Leu Glu Cys Leu Arg Thr Glu Lys
    450                 455                 460

Leu Asp His Tyr Phe Ile Pro Lys Phe Asn Leu Phe Ser Gln Glu Leu
465                 470                 475                 480

Ile Asp Arg Lys Ser Lys Glu Phe Leu Ser Lys Lys Ile Glu Tyr Glu
                485                 490                 495

Arg Asn Asn Gly Phe Pro Ile Phe Asp Lys Leu
                500                 505
```

UNITED STATES PATENT AND TRADEMARK OFFICE
CERTIFICATE OF CORRECTION

PATENT NO. : 10,010,607 B2
APPLICATION NO. : 14/855744
DATED : July 3, 2018
INVENTOR(S) : Nicolas Manel et al.

It is certified that error appears in the above-identified patent and that said Letters Patent is hereby corrected as shown below:

In the Specification

Column 7,
Line 9, "(ADBD)" should read --(ΔDBD)--.

Column 16,
Line 16, "POAA89" should read --P0AA89--.
Line 17, "Q9A515" should read --Q9A5I5--.

Column 25,
Line 7, "IF144" should read --IFI44--.

Column 33,
Line 5, "ADBD" should read --ΔDBD--.

Column 34,
Line 1, "81 g/ml" should read --8μg/ml--.

Column 36,
Line 29, "75 am" should read --75 μm--.
Line 30, "3 am" should read --3 μm--.

Column 37,
Line 40, "81a/ml" should read --8μ/ml--.
Line 59, "81 μg/ml" should read --8μg/ml--.
Line 61, "251 μM" should read --25μM--.

Column 39,
Line 44, "R-mercaptoethanol)" should read --β-mercaptoethanol)--.

Signed and Sealed this
Twentieth Day of August, 2019

Andrei Iancu
*Director of the United States Patent and Trademark Office*